United States Patent
Luna-Flores et al.

(10) Patent No.: US 10,662,446 B2
(45) Date of Patent: May 26, 2020

(54) PROPIONIBACTERIUM STRAINS FOR THE PRODUCTION OF PROPIONIC ACID

(71) Applicant: THE UNIVERSITY OF QUEENSLAND, St Lucia, Queensland (AU)

(72) Inventors: Carlos H. Luna-Flores, Yeronga (AU); Lars K. Nielsen, St Lucia (AU); Esteban Marcellin, Annerley (AU); Christopher C. Stowers, Indianapolis, IN (US); Bianca F. Martins, Sao Paulo (BR); Brad M. Cox, Indianapolis, IN (US)

(73) Assignee: The University of Queensland, Queensland (AU)

( * ) Notice: Subject to any disclaimer, the term of this patent is extended or adjusted under 35 U.S.C. 154(b) by 6 days.

(21) Appl. No.: 15/762,332

(22) PCT Filed: Sep. 29, 2016

(86) PCT No.: PCT/IB2016/001658
§ 371 (c)(1),
(2) Date: Mar. 22, 2018

(87) PCT Pub. No.: WO2017/055932
PCT Pub. Date: Apr. 6, 2017

(65) Prior Publication Data
US 2019/0071697 A1  Mar. 7, 2019

Related U.S. Application Data

(60) Provisional application No. 62/234,900, filed on Sep. 30, 2015.

(51) Int. Cl.
| | |
|---|---|
| *C12N 1/21* | (2006.01) |
| *C12P 7/52* | (2006.01) |
| *C07K 14/195* | (2006.01) |
| *C12N 15/03* | (2006.01) |
| *C12R 1/01* | (2006.01) |
| *C12N 9/00* | (2006.01) |
| *C12N 9/10* | (2006.01) |

(52) U.S. Cl.
CPC .............. *C12P 7/52* (2013.01); *C07K 14/195* (2013.01); *C12N 9/1029* (2013.01); *C12N 9/93* (2013.01); *C12N 15/03* (2013.01); *C12R 1/01* (2013.01); *C12Y 203/01086* (2013.01)

(58) Field of Classification Search
None
See application file for complete search history.

(56) References Cited

FOREIGN PATENT DOCUMENTS

| | | |
|---|---|---|
| WO | WO2014/099707 | 6/2014 |
| WO | WO2015/013334 | 1/2015 |

OTHER PUBLICATIONS

GenBank Accession No. NZ_CP014352, "Propionibacterium acidipropionici strain ATCC 55737, complete genome" (Year: 2016).*
Long et al: "Genome shuffling of Megasphaera elsdenii for improving acid-tolerance and propionate production", African Journal of Microbiology Research vol. 6(18) pp. 4041-4047, May 16, 2012.
Guan, Ningzi, et al., "Genome-shuffling improves acid tolerance of Propionibacterium acidipropionici and propionic acid production", Advances in Chemistry Research, 2012, vol. 15, pp. 143-152.
Stowers, Chris C. et al., "Development of an industrializable fermentation process for propionic acid production" Journal of Industrial Microbiology & Biotechnology, [E-pub], Mar. 14, 2014, vol. 41, No. 5, pp. 837-852.
PCT Search Report and Written Opinion for PCT/IB2016/001658, dated Apr. 25, 2017.
Carlos H Luna-Flores et al: "Improved production of propionic acid using genome shuffling", Biotechnology Journal, vol. 12, No. 2, Feb. 1, 2017 pp. 1-12 (1600120).
Carlos H Luna-Flores et al: "Genome Sequence of Propionibacterium acidipropionici ATCC 55737", Genome Announcements, vol. 4, No. 3, May 19, 2016, pp. 1-2.
Carlos H Luna-Flores et al: "Linking genotype and phenotype in an economically viable propionic acid biosynthesis process", Biotechnology for Biofuels, vol. 11, No. 1, Dec. 1, 2018 pp. 1-14.

* cited by examiner

*Primary Examiner* — Rebecca E Prouty
(74) *Attorney, Agent, or Firm* — Barnes & Thornburg LLP

(57) ABSTRACT

Disclosed herein are new strains of Propionibacterium and methods for the biosynthetic production of propionic acid.

2 Claims, 10 Drawing Sheets
Specification includes a Sequence Listing.

PROPIONIBACTERIUM STRAINS FOR THE PRODUCTION OF PROPIONIC ACID

CROSS-REFERENCE TO RELATED APPLICATIONS

This application is a national stage entry under 35 USC § 371 of PCT International Application Number PCT/IB2016/001658, filed Sep. 29, 2016, which claims priority to U.S. Provisional Patent Application No. 62/234,900, filed on Sep. 30, 2015, the disclosures of which are both incorporated by reference in their entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: One 76 kilobyte ASCII (Text) file named "258544_SeqListing.txt," created on Sep. 26, 2016.

BACKGROUND

Propionic acid (PA) is widely used in the food industry as a food preservative. PA has also found use as a precursor for the synthesis of polymers, including but not limited to polypropylene and vinyl propionate. In addition propanol and other valuable chemicals can be derived from PA. PA has traditionally been derived from fossil fuels until recently when mounting environmental concerns have shifted end users' interest to a sustainable alternative. This search for sustainable alternatives has revived bacterial fermentation as an alternative for the production of C3 chemicals.

*Propionibacterium* sp are pleomorphic rods, gram-positive bacteria that naturally produce PA as their main fermentation product through the Wood-Werckman cycle. Natively, PA is produced along with other organic acids (lactate, succinate, and acetate) resulting in low productivities and modest yields which translate in costly downstream processes. Until recently, metabolic engineering in *P. acidipropionici* had proven to be challenging mainly due to the seven Clustered Regularly Interspaced Short Palindromic Repeats (CRISPRs) which provide resistance against conjugative plasmids and bacteriophages. As disclosed herein genome shuffling (GS) can be used to improve the growth rate and PA production of *P. acidipropionici*.

Originally described in the mid 70's as protoplast fusion, GS has been extensively used in industry. Examples include increased production of tylosin in *Streptomyces fradiae* (Zhang et al., Nature, 2002, 415, 644-646), ethanol in *Saccharomyces cerevisiae* (L. Hou, Appl. Biochem. Biotechnol., 2010, 160, 1084-1093), vitamin B12 in *P. shermanii* (Zhang et al., J. Biotechnol., 2010, 148, 139-143), lactic acid in *Lactobacillus* (Patnaik et al., Nat. Biotechnol., 2002, 20, 707-12), 1,3-propanediol in *Clostridium diolis* (Otte et al., Appl. Environ. Microbiol., 2009, 75, 7610-7616), and PA in *P. acidipropionici* (Guan et al., "Genome-Shuffling Improves Acid Tolerance . . . " in Advances in Chemistry Research, Vol 15, Chapter 8 (2012) Nova Science Publishers, Inc., pp 143-152) amongst others.

To obtain *Propionibacterium* strains with higher propionic acid yields and lower byproducts, a genome shuffling (GS) protocol has been used to transfer genetic material between two strains of *Propionibacterium* resulting in novel strains with the potential for improved propionic acid production. GS combines the advantages of multi-parental crossing facilitated by DNA exchange, where the donor provides a small amount of DNA material leaving the rest of the recipient intact. The end result of GS is genetically unique strains with potentially novel pathways and regulatory mechanisms.

Previous attempts to use GS for enhancing PA production have not delivered strains with the desired phenotypes. This is due in part to the lack of genomic diversity in the known strains used in such procedures. Thus, previous efforts have failed to produce *Propionibacterium* strains that are capable of producing propionic acid in excess of 0.54 g/g using glucose or sucrose fermentations, that also retain multiple byproducts in appreciable quantities (Stowers et al., J. Ind. Microbiol. Biotechnol., 2014, 41, 837-852).

Accordingly, the success of using GS for enhancing PA production is predicated on the ability to select two strains with desirable phenotypes that if combined could result in an advantaged propionic acid production strain. Applicants have selected strains of *Propionibacterium* that they have identified as having high potential for propionic acid production. These selected strains have now been used to produce novel strains of *Propionibacterium* that have improved growth rates, enhanced propionic acid production (e.g., exceeding 0.54 g/g) and optionally, a reduced production of undesired byproducts such as acetic acid and succinic acid.

SUMMARY

In accordance with one embodiment compositions and methods are provided for the biosynthetic production of propionic acid. In accordance with one embodiment, a new strain of *Propionibacterium* is provided that has an improved ability to utilize glucose or sucrose as a carbon and energy source for enhanced yields of propionic acid relative to native *Propionibacterium* and other known derivative strains. In one embodiment a new *Propionibacterium* strain is provided having enhanced propionic acid production. In one embodiment the new strain is produced by the transfer of genetic material between a first and second strain of *Propionibacterium*, optionally by genome shuffling, wherein the first and second strains have different genomes. The strains generated after genomic shuffling are subsequently screened for strains that have an improved ability to utilize glucose/sucrose as a carbon and energy source for enhanced yields of propionic acid relative to the parent strains. In one embodiment the *Propionibacterium* strains used for genomic shuffling are selected from strains: *P. acidipropionici* ATCC 55737, *P. acidipropionici* ATCC 4875, *P. acidipropionici* ATCC 4965, *P. intermedium* ATCC 14072, and *P. jensenii* ATCC 9617. In one embodiment the new *Propionibacterium* strain having enhanced propionic acid production is a *P. acidipropionici* strain.

In accordance with one embodiment a *P. acidipropionici* strain is produced by exchanging genetic material between *P. acidipropionici* ATCC 4875 and *P. acidipropionici* ATCC 55737, optionally through genomic shuffling, wherein the growth rate of the resulting strains and the production of propionic acid is enhanced in the new strain relative to parental strains *P. acidipropionici* ATCC 4875 and *P. acidipropionici* ATCC 55737 and other known *P. acidipropionici* strains. In another embodiment a *P. acidipropionici* strain is produced by exchanging genetic material between *P. acidipropionici* ATCC 4875 and *P. acidipropionici* strain F3E8, deposited with the American Type Culture Collection (ATCC), on Jun. 25, 2015 under ATCC Accession No. PTA-122267, wherein the new generated strain has an increase in total yield (g/g) of propionic acid relative to that produced by *P. acidipropionici* ATCC 55737 when the two strains are cultured under identical conditions.

In accordance with one embodiment a method of producing a new strain of *Propionibacterium* is provided. The method comprises the steps of producing a library of *Propionibacterium* strains by conducting separate genomic shuffling reactions between various combinations of two different known strains; and combining the resulting strains generated from each reaction to form a library of *Propionibacterium* strains having enhanced genomic diversity relative to the parental strains.

In one embodiment a library of *Propionibacterium* strains is created using the strains: *P. acidipropionici* ATCC 4875, *P. acidipropionici* ATCC 4965, *P. intermedium* ATCC 14072, and *P. jensenii* ATCC 9617. In one embodiment, to obtain a library of diverse strains, *P. acidipropionici* ATCC 4875 was used to perform genomic shuffling with the other three *Propionibacterium* strains in three separate genomic shuffling reactions. In one embodiment 1, 2 or 3 rounds of genome shuffling are performed with each set of strains. Strains generated from each of the three sets of genomic shuffling reactions are combined to produce a library of *Propionibacterium* strains.

This library of strains can then be use to conduct a second round of genomic shuffling between the library of strains and selected *Propionibacterium* strains, including for example, *P. acidipropionici* ATCC 4875 or *P. acidipropionici* strain F3E8, deposited with the American Type Culture Collection (ATCC), on Jun. 25, 2015 under ATCC Accession No. PTA-122267, to produce a second set of GS generated strains. The amount of propionic acid produced in the second set of GS generated strains is then measured to identify those new strains having improved yields of propionic acid relative to *P. acidipropionici* ATCC 4875 or *P. acidipropionici* ATCC 55737. In one embodiment the second set of GS generated strains is cultured prior to the step of measuring propionic acid production to identify those strains that have enhanced growth rates relative to *P. acidipropionici* ATCC 4875 or *P. acidipropionici* ATCC 55737. Members of the second set of GS generated strains having enhanced growth rate relative to the parental strains are selected and only the selected strains are analyzed to identify those new strains having improved yields of propionic acid relative to *P. acidipropionici* ATCC 4875 or *P. acidipropionici* ATCC 55737.

In accordance with one embodiment, an isolated *Propionibacterium* strain is provided wherein said strain has a maximum growth rate of greater than 0.18/hr, and optionally at least 0.24/hr as calculated for the exponential phase of cells cultured at 32° C., pH 6.5 in PAM media. In one embodiment a new strain of *Propionibacterium* is provided having a maximum growth rate at least 1.5 times that of *P. acidipropionici* ATCC strain 4875 when the two strains are grown under identical conditions, including for example anaerobically at 32° C., pH 6.5 in media suitable for growth, including for example PAM media. In one embodiment a *P. acidipropionici* strain is provided having a growth rate of about 0.24/hr to about 0.26/hr, as calculated for the exponential phase of cells, including for example cells cultured at 32° C., pH 6.5 in PAM media.

The novel *Propionibacterium* strains of the present disclosure also have improved yields of propionic acid relative to *P. acidipropionici* ATCC 4875 and *P. acidipropionici* ATCC 55737. In one embodiment a novel *Propionibacterium* strain of the present disclosure has an increase of at least 10%, and optionally a 10 to 15%, a 15 to 20%, or a 20 to 25% or a 30 to 40% increase in total yield (g/g) of propionic acid relative to that produced by *P. acidipropionici* ATCC strain 4875 or ATCC strain 55737 when the two strains are cultured under identical conditions (e.g., anaerobically at 32° C., pH 6.5 in PAM media). In one embodiment the novel *Propionibacterium* strain produces a propionic acid yield of about 0.49 to about 0.8 g/g, about 0.5 to about 0.7 g/g, or about 0.5 to about 0.66, or about 0.66 g/g. In one embodiment the novel *P. acidipropionici* strain produces 0.77 to about 0.92 g/L/hr or about 0.84 g/L/hr or about 0.95 g/L/hr of propionic acid under optimal culture conditions, including for example cultured anaerobically at 32° C., pH 6.5 in PAM media. In one embodiment the novel *P. acidipropionici* strain produces about 0.8 to about 1.1 g/L/hr or about 0.95 g/L/hr of propionic acid under optimal culture conditions, including for example cultured anaerobically at 32° C., pH 6.5 in PAM media.

In one embodiment an isolated *Propionibacterium* strain is provided wherein said strain produces a higher yield of propionic acid than *P. acidipropionici* strain ATCC 55737. More particularly, the isolated strain is further characterized as comprising a modified gene, relative to *P. acidipropionici* strain ATCC 55737, selected from the group consisting of the ABC polar amino acid transporter gene, the Cytochrome C biogenesis gene or the ABC multiple sugar transporter gene. In one embodiment the isolated *Propionibacterium* strain encodes an altered gene product for the ABC polar amino acid transporter protein and/or the Cytochrome C biogenesis protein. In one embodiment the isolated strain comprises modified genes for each of the ABC polar amino acid transporter gene, the Cytochrome C biogenesis gene and the ABC multiple sugar transporter gene.

In one embodiment an isolated or purified *Propionibacterium* strain is provided wherein the strain has improved growth rates (e.g., greater than about 0.24/hr) and/or improved propionic acid yields (e.g., about 0.55 g/g or greater) and comprises
  (i) a modified large ribosomal RNA gene (SEQ ID NO 15) comprising a nucleotide substitution at position 1441 relative to the same gene in *P. acidipropionici* ATCC 55737, and positions 1425, 1270, and 1271 relative to the same gene in *P. acidipropionici* ATCC 4875; and/or
  (ii) a modified long chain acyl-CoA synthetase gene (SEQ ID NO: 16) comprising a deletion at position 2269 and nonsense codon after position 1500 relative to the same gene in *P. acidipropionici* ATCC 55737, and positions 264, 1650, and 2295 relative to the same gene in *P. acidipropionici* ATCC 4875. The amino acid changes in the encoding protein are at positions 500 and 757 referencing *P. acidipropionici* ATCC 55737 and positions 88 and 757 relative to the same protein in *P. acidipropionici* ATCC 4875 (see SEQ ID NO: 16; the encoded truncated peptide is provided as SEQ ID NO: 17); and/or
  (iii) a modified cation diffusion facilitator gene (SEQ ID NO: 13) comprising a nucleotide substitution at position 953 relative to the same gene in *P. acidipropionici* ATCC 55737 and positions 18, 19, 56, 211, 334, 340, 406, 451, 484, 574, and 953 relative to the same gene in *P. acidipropionici* ATCC 4875. The amino acid changes of the encoding protein (SEQ ID NO: 14) comprises an amino acid substitution at position 318 relative to the same proteins in *P. acidipropionici* ATCC 55737 and positions 7, 60, 71, 86, 112, 114, 136, 151, 162, 192, and 318 relative to the same protein in *P. acidipropionici* ATCC 4875; and/or (iv) an extra copy of the whole ribosomal RNA gene (SEQ ID NO: 18) relative to both parental strains (*P. acidipropionici* ATCC 55737 and *P. acidipropionici* ATCC 4875); and/or (v) an extra copy of the arginine deiminase regulon (SEQ ID NO: 21) relative to both parental strains (*P. acidipropionici* ATCC 55737 and *P. acidipropionici* ATCC 4875). In one embodiment the extra copy comprises a mutation at position 37 relative to both parental strains (*P. acidipropionici* ATCC 55737 and *P. acidipropionici* ATCC 4875).

In accordance with one embodiment the novel strain, *P. acidipropionici* F3E8 is provided, as deposited with the American Type Culture Collection (ATCC), 10801 University Boulevard, Manassas, Va., 20110-2209 USA, on Jun. 25, 2015 under ATCC Accession No. PTA-122267. The present disclosure also encompasses variants of said deposited strain, wherein the variant has been subjected to further genetic manipulations. Such variants include derivatives of strain F3E8 generated by subjecting the F3E8 strain to genomic shuffling with different strains of *P. acidipropionici*. In accordance with one embodiment the novel strain, *P. acidipropionici* WGS 7 is provided, as deposited with the American Type Culture Collection (ATCC), 10801 University Boulevard, Manassas, Va., 20110-2209 USA, on Sep. 2, 2016 under ATCC Accession No. PTA 123476. Strain, *P. acidipropionici* F3E8 was generated using glucose as the carbon and energy source whereas WGS 7 was generated using sucrose as the carbon and energy source.

In accordance with one embodiment, a method of producing a *Propionibacterium* strain having improved yields of propionic acid production is provided wherein the method comprises subjecting a strain selected from the group consisting of *P. acidipropionici* F3E8, *P. acidipropionici* WGS 7, *P. acidipropionici* ATCC 4875 and *P. acidipropionici* ATCC 55737 to genomic shuffling with a different strain selected from the group consisting of *P. acidipropionici* F3E8, *P. acidipropionici* WGS 7, *P. acidipropionici* ATCC 4875 and *P. acidipropionici* ATCC 55737, and recovering the resulting modified strains that have enhanced growth rates or improved propionic acid yields relative to the parental strains. In one embodiment a method of producing a novel *P. acidipropionici* strain having improved yields of propionic acid production is provided wherein the method comprises subjecting a first and second strain of *P. acidipropionici* to genome shuffling. More particularly, in one embodiment the first strain is selected from the group consisting of *P. acidipropionici* ATCC 4875 and *P. acidipropionici* ATCC 55737 and the second strain is *P. acidipropionici* strain F3E8, deposited with the American Type Culture Collection (ATCC), on Jun. 25, 2015 under ATCC Accession No. PTA-122267. The new strains produced by subjecting the first and second strains of *P. acidipropionici* to genome shuffling are then cultured to identify strains that have enhanced growth rates or propionic acid production relative to *P. acidipropionici* ATCC 4875 or *P. acidipropionici* ATCC 55737. In one embodiment the method comprises the steps of first selecting the resulting new strains having enhance growth rate relative to *P. acidipropionici* ATCC 4875 or *P. acidipropionici* ATCC 55737; and then measuring propionic acid production in the selected strains to identify those new strains having improved yields of propionic acid relative to *P. acidipropionici* ATCC 4875 or *P. acidipropionici* ATCC 55737.

In one embodiment the modified strains have one, two, three, four, or five modifications in a cellular component and/or the gene encoding the cell component, wherein the cell component in one embodiment is selected from the ABC polar amino acid transporter, the Cytochrome C biogenesis, the ABC multiple sugar transporter, the large subunit of ribosomal RNA, the long chain acyl-CoA synthetase, the cation diffusion facilitator, the whole ribosomal RNA operon, and the arginine deminnase regulon. In one embodiment the modified strains have one, two, or three modifications in a cellular component and/or the gene encoding the cell component, wherein the cell component in one embodiment is selected from the large subunit of ribosomal RNA, the long chain acyl-CoA synthetase, and the cation diffusion facilitator.

In one embodiment a method is provided for producing propionic acid. In one embodiment the method comprises the steps of culturing a *P. acidipropionici* strain under conditions suitable for growth of the strain and recovering the propionic acid produced by said strain. In one embodiment the *P. acidipropionici* strain has a maximum growth rate of at least 0.24/hr calculated for the exponential phase of cells cultured at 32° C., pH 6.5 in PAM media. In a further embodiment the *P. acidipropionici* strain produces a propionic acid yield of about 0.49 to about 0.8 g/g, about 7.0 to about 8.0 g/g, about 0.5 to about 0.7 g/g, or about 0.5 to about 0.66, or about 0.66 g/g. In one embodiment the *P. acidipropionici* strain used to produce propionic acid is strain F3E8, deposited with the American Type Culture Collection (ATCC), 10801 University Boulevard, Manassas, Va., 20110-2209 USA, on Jun. 25, 2015, and assigned ATCC Accession No. PTA-122267. The present disclosure also encompasses novel *P. acidipropionici* strains produced by the transfer of genetic material between *P. acidipropionici* ATCC 4875 and *P. acidipropionici* ATCC 55737, including strains produced during genome shuffling of *P. acidipropionici* strain F3E8 with either *P. acidipropionici* ATCC 4875 or *P. acidipropionici* ATCC 55737 and/or genome shuffling of *P. acidipropionici* strain F3E8 and a different *P. acidipropionici* strain. In one embodiment the *P. acidipropionici* strain used to produce propionic acid is strain WGS 7, as deposited with the American Type Culture Collection (ATCC), 10801 University Boulevard, Manassas, Va., 20110-2209 USA, on Sep. 2, 2016 under ATCC Accession No. PTA 123476.

BRIEF DESCRIPTION OF THE DRAWINGS

FIG. 3A is a graph of the inhibition of *P. acidipropionici* ATCC 4875, whereas FIG. 3B provides data for the inhibition of *P. acidipropionici* F3E8.

FIG. 4A: *P. acidipropionici* ATCC 55737, FIG. 4B: *P. acidipropionici* WGS 7 strain obtained from GS. Optical Density: solid diamonds; Propionic Acid: solid squares; Glucose: solid circles; Succinic Acid: open squares; Acetic Acid: open diamonds; Pyruvate: open circles. FIG. 4C is a bar graph showing the specific consumption rate of sucrose (qs), the specific production rate of PA (qp), and the specific growth rate (μ). FIG. 4D is a bar graph demonstrating the specific consumption rates of the free amino acids presented in the PAM media. shaded bars: *P. acidipropionici* ATCC 55737. Open bars: *P. acidipropionici* WGS 7. The data represent the average of two biological replicates for each strain. The specific rates were calculated in the middle exponential phase (15 to 25 hours).

DETAILED DESCRIPTION

Definitions

Figure 1A:
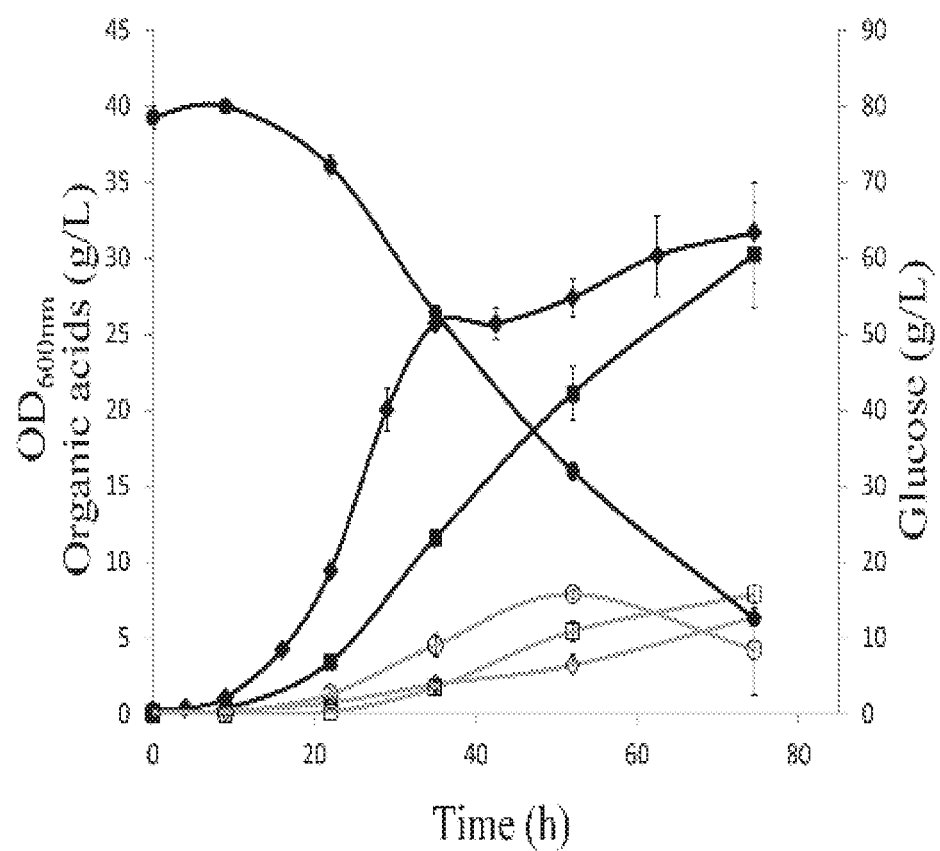
FIGS. 1A-1C are graphs demonstrating the fermentation profile in 2 L bioreactors for *P. acidipropionici* ATCC 4875 (FIG. 1A), *P. acidipropionici* ATCC 55737 (FIG. 1B), and *P. acidipropionici* F3E8 strain (FIG. 1C). Plots display the average of two biological replicates. Optical Density measured at 600 nm: Black line and ◆; Propionic Acid: Black line and ■; Glucose: Black line and •; Succinic Acid: Grey line and □; Acetic Acid: Grey line and ◇; Pyruvate: Grey line and ○.

In describing and claiming the invention, the following terminology will be used in accordance with the definitions set forth below.

The term "about" as used herein means greater or lesser than the value or range of values stated by 10 percent but is not intended to designate any value or range of values to only this broader definition. Each value or range of values preceded by the term "about" is also intended to encompass the embodiment of the stated absolute value or range of values.

As used herein, the term "purified" and like terms define the isolation of bacteria, or a compound in a form that is substantially free of contaminants normally associated with the bacteria, or compound in a native or natural environment. As used herein, the term "purified" does not require absolute purity; rather, it is intended as a relative definition. The term "purified bacteria" is used herein to describe a bacterial population which has been separated from other bacteria and is present as a homogenous population.

The term "isolated" requires that the referenced material be removed from its original environment (e.g., the natural environment if it is naturally occurring).

As used herein an "altered gene product" defines an RNA or amino acid sequence encoded by a modified gene, wherein the RNA or amino acid sequence has a different primary sequence relative to the corresponding gene product produced by the wild type gene/reference gene.

As used herein a 'copy number variation' defines a different number of a specific gene relative to the number of the same gene in the wild type strains. The variation can be a duplication or deletion of a sequence encoding for RNA or an amino acid sequence. The extra copy can be an exact sequence or a modified one relative to the same sequence of the strain.

As used herein an "amino acid modification" encompasses (i) a substitution of an amino acid with a different amino acid, (ii) an addition/insertion of an amino acid, or (iii) a deletion of one or more amino acids.

As used herein an amino acid "substitution" refers to the replacement of one amino acid residue by a different amino acid residue.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met, Leu, Ile, Val, Cys
V. Large, aromatic residues:
Phe, Tyr, Trp.

A "nonconservative amino acid substitution" is defined as an exchange of a first amino acid with a second amino acid wherein the second amino acid is selected from one of the above five groups outside of the group of the first amino acid.

A "promoter" is a DNA sequence that directs the transcription of a polynucleotide. Typically a promoter is located in the 5' region of a polynucleotide to be transcribed, proximal to the transcriptional start site of such polynucleotide.

A "gene" as used herein describes nucleic acid molecules comprising an open reading frame encoding a gene product (i.e., an RNA transcript and/or polypeptide) as well as the associated regulatory regions controlling the expression of the gene product and non-coding transcribed regions (e.g., introns and 5' and 3' untranslated regions).

A "modified gene" as used herein is a gene that has been altered in some manner relative to the corresponding gene found in a reference strain, (e.g. *P. acidipropionici* ATCC strain 4875 or 55737). Alterations may include duplication or deletion of the entire gene, duplication or deletion of portions of the gene, or insertions or substitutions of nucleotides in the gene sequence.

The term "identity" as used herein defines the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) J. Mol. Biol. 215:403-410) are available for determining sequence identity.

A "culture medium" refers to any liquid, semi-solid or solid media that can be used to support the growth of a microorganism used in the methods of the invention. In some embodiments, the microorganism is a bacterium, e.g., *P. acidipropionici*. Media for growing microorganisms are well known, see, e.g., Sambrook et al. and Current Protocols in Molecular Biology, F. M. Ausubel et al., eds., Current Protocols, a joint venture between Greene Publishing Associates, Inc. and John Wiley & Sons, Inc., (1998 Supplement) (Ausubel).

As used herein the term "genome shuffling" or "GS" is a process of transferring genetic material between two bacterial strains to create a new recombined strain comprising elements from the two initial strains.

As used herein the term "growth rate" absent any further qualification, means the maximum specific growth rate (μ max) calculated based on the change in cell density in exponential phase as measured by the change in optical density based on light absorption at 600 nm. Growth rate is expressed in the units of per time or 1/time using the formula $N=N_0 e^{\mu \tau}$ wherein "N" is the cell density measured by the OD600, "N₀" is the original or previous cell density, "t" is time, "e" is a constant (Euler number, e=2.71828), and $\mu$ is the growth rate.

As used herein the term "yield" defines the amount of product of interest produced divided by the amount of total substrate consumed (g/g).

As used herein the term "production rate of propionic acid" represents the total grams of propionic acid produced per liter per hour.

As used herein the term "titer" represents the total grams of product produced per liter of fermentation broth.

The term "fermentation" refers to a metabolic process performed by an organism that converts one substrate to another in which the cell is able to obtain cellular energy, such as when an organism utilizes glucose and converts it to propionic acid.

Embodiments

In accordance with one embodiment compositions and methods are provided for the biosynthetic production of propionic acid. In accordance with one embodiment, a new strain of *Propionibacterium* is provided that has an improved ability to utilize glucose as a carbon and energy source for enhanced yields of propionic acid relative to native *Propionibacterium* and other known derivative strains. In accordance with one embodiment, the novel *Propionibacterium* strain is a *P. acidipropionici* strain.

Novel strains having the requisite improved growth rates and/or propionic acid yields can be produced by conducting genomic shuffling between any suitable *Propionibacterium* strains. In one embodiment, strains with enhanced yields of propionic acid are produced by exchanging genetic material between *P. acidipropionici* ATCC 4875 and *P. acidipropionici* ATCC 55737, optionally through genomic shuffling. The resulting strains can then be further manipulated by subjecting the resulting strains, including for example any of *P. acidipropionici* strains F3E8, F3G8, F3C8, F3H8, F3E9, F3F8, F3F6, F3D9, F3C1, F3B9, WGS.1, WGS.2, WGS.3, WGS.4, WGS.5, WGS.6, WGS 7, WGS.8, WGS.9, WGS.10, WGS.11, WGS.12, and WGS.13 disclosed herein, to further genomic shuffling with different strains of *P. acidipropionici*. In accordance with one embodiment, a new *P. acidipropionici* strain is produced by exchanging genetic material between *P. acidipropionici* strain F3E8 and a different *P. acidipropionici* strain. In one embodiment a new *P. acidipropionici* strain is produced by exchanging genetic material, optionally through genomic shuffling, from a first strain selected from the group consisting of *P. acidipropionici* ATCC 4875 and *P. acidipropionici* ATCC 55737 and a second strain, wherein the second strain is selected from the group consisting of *P. acidipropionici* strain F3E8, deposited with the American Type Culture Collection (ATCC), on Jun. 25, 2015 under ATCC Accession No. PTA-122267 or *P. acidipropionici* strain WGS 7, deposited with the American Type Culture Collection (ATCC), on Sep. 2, 2016 under ATCC Accession No. PTA 123476, wherein the new strain has an increase in total yield (g/g) of propionic acid relative to that produced by *P. acidipropionici* ATCC 55737 when the two strains are cultured under identical conditions. In one embodiment a new *P. acidipropionici* strain is produced by exchanging genetic material, optionally through genomic shuffling, between *P. acidipropionici* strain F3E8 and *P. acidipropionici* strain WGS 7.

In one embodiment the resulting strain will have a maximum growth rate of at least 0.24/hr as calculated for the exponential phase of cells cultured under optimal conditions, including for example anaerobically at 32° C., pH 6.5 in PAM media, and/or a propionic acid yield of about 0.55 g/g or higher. In one embodiment the new strain will produce propionic acid at a yield of about 0.49 to about 0.8 g/g, a about 0.5 to about 0.7 g/g, or about 0.5 to about 0.66, or about 0.66 g/g.

In accordance with one embodiment, the new strain is generated by conducting genomic shuffling between two parental *P. acidipropionici* strains. Briefly, the two parental strains are separately cultured and then collected from the culture by centrifugation and subjected to enzymatic treatment (lysozyme) to generate protoplasts. Equal numbers of protoplasts from each population are mixed together in protoplast formation buffer. Polyethylene glycol and $CaCl_2$ are added to the suspension to induce fusion of the protoplasts, and the fused protoplasts are subsequently centrifuged, washed and resuspended in regeneration medium. Cells are then plated on growth media and cells exhibiting growth rates of at least 0.19/hr are selected for further analysis.

In accordance with one embodiment a method of producing a novel *Propionibacterium* strain having enhanced growth rates or propionic acid production relative to *P. acidipropionici* ATCC 4875 or *P. acidipropionici* ATCC 55737 is provided. The method comprises the steps of exchanging genetic material, optionally through genomic shuffling, between a first and second set of *Propionibacterium* strains. More particularly, the first set of *Propionibacterium* strains is selected from the group consisting of *P. acidipropionici* ATCC 4875, *P. acidipropionici* ATCC 55737 or a strain generated from genomic shuffling between *P. acidipropionici* ATCC 4875 and *P. acidipropionici* ATCC 55737, *P. acidipropionici* ATCC 4965, *P. intermedium* ATCC 14072, or *P. jensenii* ATCC 9617. The second set of *Propionibacterium* strains is *P. acidipropionici* strain F3E8, deposited with the American Type Culture Collection (ATCC), on Jun. 25, 2015 under ATCC Accession No. PTA-122267. The strains generated by the genomic shuffling between the first and second sets of *Propionibacterium* strains are then cultured to identify a novel *Propionibacterium* strain having enhanced growth rates or propionic acid production relative to *P. acidipropionici* ATCC 4875 or *P. acidipropionici* ATCC 55737. In one embodiment, the strains generated by the genomic shuffling between the first and second sets of *Propionibacterium* strains are first cultured to identify those strains exhibiting an enhance growth rate relative to *P. acidipropionici* ATCC 4875 or *P. acidipropionici* ATCC 55737. Those strains that exhibit a relative enhanced growth rate are then selected and the selected strains are then separately cultured to identify which of the selected strains have improved yields of propionic acid relative to *P. acidipropionici* ATCC 4875 or *P. acidipropionici* ATCC 55737. In accordance with one embodiment the first set of strains is generated from genomic shuffling between *P. acidipropionici* ATCC 4875 and *P. acidipropionici* ATCC 55737. In one embodiment the first set of strains is generated from genomic shuffling between *P. acidipropionici* ATCC 4875 and *P. acidipropionici* ATCC 14072. In one embodiment the first set of strains is generated from genomic shuffling between *P. acidipropionici* ATCC 4875 and *P. jensenii* ATCC 9617. In one embodiment the first set of strains represents a library of strains produced by the combination of two or more strains generated by separate genomic shuffling reactions. In one embodiment, the first set of strains in the disclosed method of producing a novel *Propionibacterium* strain having enhanced growth rates or propionic acid production relative to *P. acidipropionici*

ATCC 4875 or *P. acidipropionici* ATCC 55737 comprises a mixture of strains from 2, 3 or 4 of the following separate genomic shuffling reactions:

i) genomic shuffling between *P. acidipropionici* ATCC 4875 and *P. acidipropionici* ATCC 55737;

ii) genomic shuffling between *P. acidipropionici* ATCC 4875 and *P. acidipropionici* ATCC 4965;

iii) genomic shuffling between *P. acidipropionici* ATCC 4875 and *P. intermedium* ATCC 14072; and iv) genomic shuffling between *P. acidipropionici* ATCC 4875 and *P. jensenii* ATCC 9617. In one embodiment, the first set of strains represents a combination of strains generated from i) and ii); or ii) and iii); or iii) and iv); or ii) and iv) or ii), iii) and iv); or i), ii), iii) and iv).

In accordance with one embodiment a method of producing a novel *P. acidipropionici* strain having improved yields of propionic acid production, said method comprises the steps of subjecting a first and second strain of *P. acidipropionici* to genome shuffling, wherein said first strain is selected from the group consisting of *P. acidipropionici* ATCC 4875 and *P. acidipropionici* ATCC 55737 and said second strain is *P. acidipropionici* strain F3E8, deposited with the American Type Culture Collection (ATCC), on Jun. 25, 2015 under ATCC Accession No. PTA-122267, to produce new strains;

optionally culturing said new strains to identify strains that have enhanced growth rates relative to *P. acidipropionici* ATCC 4875 or *P. acidipropionici* ATCC 55737 and selecting the resulting new strains having enhance growth rate; and measuring propionic acid production in said new strains to identify strains having improved yields of propionic acid relative to *P. acidipropionici* ATCC 4875 or *P. acidipropionici* ATCC 55737.

The present disclosure also encompasses any of the novel *P. acidipropionici* strains produced in accordance with the methods disclosed herein.

In accordance with one embodiment an isolated or purified novel *Propionibacterium* strain is provided wherein the novel strain exhibits a faster growth rate and/or enhanced yields of propionic acid relative to *P. acidipropionici* strain F3E8, *P. acidipropionici* ATCC 4875 and/or *P. acidipropionici* ATCC 55737. In one embodiment the novel strains of the present disclosure have a maximum growth rate at least 1.5 times that of *P. acidipropionici* ATCC strain 4875 and/or an increase of 15 to 20% in total yield (g/g) relative to that of *P. acidipropionici* ATCC strain 4875, when the two strains are grown under identical conditions, including for example anaerobically at 32° C., pH 6.5 in PAM media. In one embodiment the *Propionibacterium* strain of the present disclosure has a growth rate of about 0.24/hr to about 0.26/hr, as calculated for the exponential phase of cells cultured at 32° C., pH 6.5 in PAM media. In one embodiment the *Propionibacterium* strain is a *P. acidipropionici* strain.

In one embodiment a *P. acidipropionici* strain of the present disclosure has an increase of at least 10%, and optionally a 10 to 15%, 15 to 20%, or a 20 to 25% in yield (g/g) of propionic acid relative to that produced by *P. acidipropionici* ATCC strain 4875 when the two strains are cultured under identical conditions (e.g., anaerobically at 32° C., pH 6.5 in PAM media). In one embodiment the novel *P. acidipropionici* strain produces propionic acid with a yield of about 0.49 to about 0.7 g/g, about 0.5 to about 0.7 g/g, or about 0.5 to about 0.66, or about 0.66 g/g. In one embodiment the novel *P. acidipropionici* strain produces at least about 0.77 to about 0.92 g/L/hr or about 0.84 g/L/hr of propionic acid under optimal culture conditions, including for example anaerobically at 32° C., pH 6.5 in PAM media. In one embodiment a *P. acidipropionici* strain of the present disclosure has an increase of at least 10%, and optionally a 10 to 15%, 15 to 20%, or a 20 to 25% in yield (g/g) of propionic acid relative to that produced by *P. acidipropionici* strain ATCC 55737 when the two strains are cultured under identical conditions (e.g., anaerobically at 32° C., pH 6.5 in PAM media).

In one embodiment the *P. acidipropionici* strain is an isolated or purified *P. acidipropionici* strain wherein said strain has an increase of 15 to 20% in yield (g/g) of propionic acid relative to that produced by *P. acidipropionici* ATCC strain 4875, and optionally has a maximum growth rate at least 1.5 times that of *P. acidipropionici* ATCC strain 4875 when both strains are cultured under identical conditions, optionally anaerobically at 32° C., pH 6.5 in an acceptable media such as PAM. In one embodiment the *P. acidipropionici* strain is an isolated or purified *P. acidipropionici* strain wherein the strain has a propionic acid yield of about 0.49 to about 0.7 g/g, about 0.6 to about 0.8 g/g, about 0.5 to about 0.7 g/g, or about 0.5 to about 0.66, or about 0.66 g/g, or about 0.75 g/g, and optionally has a maximum growth rate at least 1.5 times that of *P. acidipropionici* ATCC strain 4875 when both strains are cultured under identical conditions, optionally anaerobically at 32° C., pH 6.5 in an acceptable media such as PAM. In one embodiment a new *P. acidipropionici* strain is provided where the strain is an isolated or purified *P. acidipropionici* strain having a propionic acid yield that is 20, 30 or 40% higher than the propionic acid yield of *P. acidipropionici* strain ATCC 55737 when both strains are grown under identical conditions, optionally, anaerobically at 32° C., pH 6.5 in an acceptable media such as PAM. In one embodiment the *P. acidipropionici* strain is an isolated or purified *P. acidipropionici* strain wherein the strain has a propionic acid yield of about 0.49 to about 0.8 g/g, about 0.5 to about 0.7 g/g, or about 0.5 to about 0.66, or about 0.55 or 0.66 g/g, and optionally has a maximum growth rate of about 0.24/hr to about 0.26/hr, as calculated for the exponential phase of cells cultured at 32° C., pH 6.5 in PAM media. In one embodiment the cultured *P. acidipropionici* strain is an isolated or purified *P. acidipropionici* strain wherein the strain produces about 0.84 g/L/hr to about 0.95 g/L/hr of propionic acid, and optionally has a maximum growth rate of at least 0.24/hr OD600 as calculated for the exponential phase of cells cultured at 32° C., pH 6.5 in an acceptable media such as PAM. In one embodiment the cultured *P. acidipropionici* strain is an isolated or purified *P. acidipropionici* strain wherein the strain produces at least about 0.77 to about 0.95 g/L/hr or about 0.84 g/L/hr of propionic acid under optimal culture conditions and optionally has a growth rate of about 0.24/hr to about 0.26/hr, as calculated for the exponential phase of cells cultured at 32° C., pH 6.5 in PAM media.

In accordance with one embodiment, any of the above described *Propionibacterium* strains are further characterized by comprising one or more modified genes relative to *P. acidipropionici* ATCC 4875 and ATCC 55737 as per Tables 1 and 7. In one embodiment the *Propionibacterium* strain comprises a modified gene, relative to strain *P. acidipropionici* ATCC 4875 and ATCC 55737, encoding for the large subunit ribosome, the long chain acyl-CoA synthetase, or the cation diffusion facilitator (Table 1). In one embodiment the *Propionibacterium* strain comprises a modified gene, relative to strain *P. acidipropionici* strain ATCC 55737, selected from the group consisting of the ABC polar amino acid transporter gene, the Cytochrome C biogenesis gene and the ABC multiple sugar transporter gene (Table 7). In one embodiment the modified gene comprises 1, 2, 3, 4, 5, 6, 7, 8, 9, or 10 modifications relative to the corresponding gene found in strain *P. acidipropionici* ATCC 55737 or ATCC 4875, wherein each modification represents a single nucleotide insertion, deletion or substitution. In one embodiment a *Propionibacterium* strain is provided that comprises modified genes, relative to *P. acidipropionici* ATCC 55737 or ATCC 4875, for each of the large subunit ribosome, the long chain acyl-CoA synthetase, and the cation diffusion facilitator.

In accordance with one embodiment an isolated *Propionibacterium* strain is provided, optionally a *P. acidipropionici* strain, wherein said strain has a maximum growth rate of at least 0.24/hr as calculated for the exponential phase of cells cultured anaerobically at 32° C., pH 6.5 in PAM media, and said strain comprises a modified gene, relative to strain *P. acidipropionici* ATCC 55737 or ATCC 4875, that encodes an altered gene product for the ABC polar amino acid transporter, the Cytochrome C biogenesis protein, the large subunit ribosomal RNA, the long chain acyl-CoA synthetase, or the cation diffusion facilitator.

In accordance with one embodiment an isolated *Propionibacterium* strain is provided, optionally a *P. acidipropionici* strain, having an improved propionic acid yield relative to *P. acidipropionici* ATCC strain 4875 and ATCC 55737, wherein the strain comprises a modified gene, relative to strain *P. acidipropionici* ATCC 4875 and ATCC 55737 for the ABC polar amino acid transporter gene, the Cytochrome C biogenesis gene, the ABC multiple sugar transporter gene, the large subunit ribosome, the long chain acyl-CoA synthetase, or the cation diffusion facilitator. In one embodiment the *Propionibacterium* strain comprising the modified large subunit ribosome, the long chain acyl-CoA synthetase, or the cation diffusion facilitator has an increase of at least 15 to 20% in total yield (g/g) of propionic acid relative to that produced by *P. acidipropionici* ATCC 4875 when the two strains are cultured under identical conditions, and in one embodiment producing a propionic acid yield of at least 0.55 or 0.66 g/g. In one embodiment the strain comprises a modified large subunit ribosome, long chain acyl-CoA synthetase, and cation diffusion facilitator genes. In one embodiment the modified gene encodes an altered gene product.

In accordance with one embodiment of the present disclosure isolated *Propionibacterium* strains were initially selected that produced enhanced yields of propionic acid. After analyzing ten selected strains, three variant genes were conserved in all ten selected strains (Table 1). The variations were:

i) in the cation diffusion facilitator,
ii) in the large subunit ribosomal RNA (23S),
iii) in the long chain fatty acyl-CoA synthetase.

The positions of the variants are specified in Table 1.

TABLE 1

Positions of the conserved gene variants found in the 10 new strains taking as reference *P. acidipropionici* ATCC 4875 or *P. acidipropionici* ATCC 55737. All 10 strains had the conserved mutations in their genome.

| Gene | Variant | Change (Comparing new strains to ATCC 4875) (Nucleic Acid) | Change (Comparing new strains to ATCC 55737) (Nucleic Acid) |
|---|---|---|---|
| Cation diffusion facilitator | SNP | 19: G > A, 178: T > G, 211: G > A, 256: A > G, 334: G > A, 340: C > G, 406: A > C, 451: C > A, 484: T > C, 574: A > G, 953: G > A | 953: G > A |
| Large subunit ribosomal RNA | SNP | 1270: G > A, 1271: T > C, 1425: G > T | 1441: A > G |
| Long chain fatty acyl-CoA synthetase | INDEL or SNP | 264: G > C, 1650: C > G, 2295: G > A | 1500: DEL > ATGA, 2269: DEL > A |

| Gene | Variant | Change (Comparing new strains to ATCC 4875) (Protein) | Change (Comparing new strains to ATCC 55737) (Protein) |
|---|---|---|---|
| Cation diffusion facilitator | SNP | 7: V > I, 60: S > A, 71: D > N, 86: I > V, 112: V > I, 114: P > A, 136: N > H, 151: P > T, 162: S > P, 192: T > A, 318: C > Y | 318: C > Y |
| Long chain fatty acyl-CoA synthetase | SNP | 88: M > I, 757: T > X | 500: S > X, 757: T > X |

*New strains: the 10 strains resulted from genome shuffling
ATCC4875: *P. acidipropionici* ATCC 4875
ATCC55737: *P. acidipropionici* ATCC 55737
SNP: Single nucleotide polymorphism
INDEL: Insertion or deletion
X: Indicates the amino acid cannot be defined

| Legend of amino acids | | | |
|---|---|---|---|
| Amino Acid | SLC | DNA codons | Relationships |
| Isoleucine | I | ATT, ATC, ATA | N, Ali |
| Leucine | L | CTT, CTC, CTA, CTG, TTA, TTG | N, Ali |
| Valine | V | GTT, GTC, GTA, GTG | N, Ali |
| Phenylalanine | F | TTT, TTC | N, Aro |
| Methionine | M | ATG | N |
| Cysteine | C | TGT, TGC | PU |
| Alanine | A | GCT, GCC, GCA, GCG | N, Ali |
| Glycine | G | GGT, GGC, GGA, GGG | PU |
| Proline | P | CCT, CCC, CCA, CCG | N |
| Threonine | T | ACT, ACC, ACA, ACG | PU |
| Serine | S | TCT, TCC, TCA, TCG, AGT, AGC | PU |
| Tyrosine | Y | TAT, TAC | Aro |
| Tryptophan | W | TGG | N |
| Glutamine | Q | CAA, CAG | PU, Ami |
| Asparagine | N | AAT, AAC | PU, Ami |
| Histidine | H | CAT, CAC | POS |
| Glutamic acid | E | GAA, GAG | NEG, A |
| Aspartic acid | D | GAT, GAC | NEG, A |
| Lysine | K | AAA, AAG | POS, B |
| Arginine | R | CGT, CGC, CGA, CGG, AGA, AGG | POS, B |
| Stop codons | Stop | TAA, TAG, TGA | |

SLC: Single-letter data-base codes; A: Acidic; B: Basic; Ali: Aliphatic; Ami: Amine; Aro: Aromatic; N: Nonpolar; PU: Polar uncharged; NEG: negatively charged; POS: Positively charged.

In one embodiment an isolated *Propionibacterium* strain is provided, optionally a *P. acidipropionici* strain, that comprises a modified large subunit ribosome gene that encodes a large subunit ribosomal RNA (SEQ ID NO: 15) wherein the gene is altered in its primary sequence relative to the same gene in *P. acidipropionici* ATCC 55737 or ATCC 4875. In one embodiment the large subunit ribosomal gene of the presently disclosed *Propionibacterium* strain is altered by 1, 2, or 3 nucleotide substitutions. In accordance with one embodiment the large subunit ribosomal (23S) gene of the present *Propionibacterium* strain differs from the large subunit ribosomal gene of *P. acidipropionici* ATCC 4875 by 1, 2, or 3 nucleic acid substitutions at positions 1270, 1271 and 1425, and more particularly in one embodiment the nucleotide substitutions are G1270A, T1271C and G1425T. In one embodiment the large subunit ribosomal (23S) gene comprises a sequence having 99% sequence identity relative to the same gene in *P. acidipropionici* ATCC 55737 with a substitution at position 1425, and more particularly in one embodiment the nucleotide substitution is A1441G.

In one embodiment an isolated *Propionibacterium* strain is provided, optionally a *P. acidipropionici* strain, wherein the strain comprises a modified long chain acyl-CoA synthetase gene relative to *P. acidipropionici* ATCC 55737 or ATCC 4875. In one embodiment the modification to the long chain acyl-CoA synthetase gene prevents the expression of a functional long chain acyl-CoA synthetase. In one embodiment the gene comprises a nucleotide insertion or deletion that causes a frameshift mutation. In one embodiment the insertion or deletion introduces a stop codon into the reading frame of the transcribed mRNA resulting in the production of a truncated peptide. In one embodiment the gene encoding the long chain acyl-CoA synthetase comprises a non-sense codon after nucleotide position 1500 and deletion or insertion at position 2269 relative to the same gene in *P. acidipropionici* ATCC 55737 and positions 264, 1271, and 2295 to ATCC 4875. In one embodiment the encoded long chain acyl-CoA synthetase is truncated near amino acid position 500 of the native protein and position 757 relative to *P. acidipropionici* ATCC 55737 and amino acid substitution at position 88 and non-sense amino acid substitution at position 757 relative to same amino acid sequence in *P. acidipropioici* ATCC 4875 In one embodiment the modified long chain acyl-CoA synthetase gene comprises the sequence of SEQ ID NO: 16 or a sequence that encodes the truncated peptide of SEQ ID NO: 17.

In one embodiment an isolated *Propionibacterium* strain is provided, optionally a *P. acidipropionici* strain, wherein the strain comprises a modified cation diffusion facilitator gene. In accordance with one embodiment the cation diffusion facilitator gene (SEQ ID NO: 13) of the present *Propionibacterium* strain differs from the cation diffusion facilitator gene in *P. acidipropionici* ATCC 4875 by 1, 2, 3, 4, 5, 6, 7, 8, 9, 10, 11 or more nucleic acid substitutions at positions 19,178, 256, 211, 334, 340, 406, 451, 484, 574, and 953. The particular substitutions are G19A, T178G, G211A, A256G, G334A, C340G, A406C, C451A, T484C, A574G, and G953A. In one embodiment the modified cation diffusion facilitator gene comprises a sequence having 99.5% or 99% sequence identity relative to the same gene in *P. acidipropionici* ATCC 55737 and optionally having an adenosine at position 953. In one embodiment the modified gene encodes an altered gene product, wherein the encoded polypeptide comprises one or more amino acid substitutions relative to the cation diffusion facilitator protein encoded by *P. acidipropionici* ATCC 4875. In accordance with one embodiment the cation diffusion facilitator protein (SEQ ID: 14) of the present *Propionibacterium* strain differs from the cation diffusion facilitator protein encoded in *P. acidipropionici* ATCC 4875 by 1, 2, 3, 4, 5, 6, 7, 8, 9, 10, 11 or more amino acid substitutions at positions 7, 60, 71, 86, 112, 114, 136, 151, 162, 192, and 318 with amino acid residues I, A, N, V, I, A, H, T, P, A, and Y respectively. In one embodiment the altered cation diffusion facilitator protein differs from the cation diffusion facilitator protein encoded by *P. acidipropionici* ATCC 55737 by 1, 2, or 3 non-conservative amino acid substitutions. In one embodiment the altered gene product of the cation diffusion facilitator of the present strain comprises an amino acid substitution at amino acid position 318 relative to the cation diffusion facilitator protein encoded by *P. acidipropionici* ATCC 4875, and more particularly the amino acid substitution is a non-conservative amino acid substitution. In one embodiment the isolated *Propionibacterium* strain of the present disclosure encodes a cation diffusion facilitator protein wherein the native C at amino acid position 318 is substituted with F, Y, and W. In one embodiment the isolated *Propionibacterium* strain of the present disclosure encodes a cation diffusion facilitator protein wherein the native C at amino acid position 318 is substituted with Y. In one embodiment the modified cation diffusion facilitator protein gene comprises the sequence of SEQ ID NO: 13 or a gene that encodes a peptide of SEQ ID NO: 14. SEQ ID NO: 13 differs in sequence from the cation diffusion facilitator protein gene of *P. acidipropionici* ATCC 4875, at 11 different nucleotides (at positions 19, 178, 211, 256, 334, 340, 406, 451, 484, 574, and 953). In one embodiment the encoded cation diffusion facilitator protein comprises the sequence of SEQ ID NO: 14, or a polypeptide that differs from the same protein sequence in *P. acidipropionici* ATCC 4875 or ATCC 55737 by 1, 2, 3, or more amino acid substitutions at positions referred in Table 1.

In one embodiment the new strain has an extra copy of the whole ribosomal RNA and an extra copy of the arginine deiminase regulon (ArgR). The extra copy of the ArgR has a mutation in position 37 of the gene (DEL of GC). The mutation is present in one of the two active domains of the protein. The mutation causes a frameshift in the gene. This gene has been associated with the regulation of the arginine deiminase pathway (involved in acid tolerance mechanism). The mutation reported here has a positive effect contributing to the improvement of the new strain *P. acidipropionici* F3E8.

In one embodiment an isolated *Propionibacterium* strain is provided, optionally a *P. acidipropionici* strain, wherein the strain comprises (i) a modified large ribosomal RNA comprising a nucleotide substitution of the large ribosomal gene at position 1441 relative to the same gene in *P. acidipropionici* ATCC 55737 and position 1270, 1271, and 1425 relative to the same gene in *P. acidipropionici* ATCC 4875; and/or (ii) a modified long chain acyl-CoA synthetase gene comprising a nonsense codon after nucleotide position 1500 and position 2269 relative to the same gene in *P. acidipropionici* ATCC 55737 and positions 264, 1650, and 2295 relative to the same gene in *P. acidipropionici* ATCC 4875; and/or (iii) a modified cation diffusion facilitator gene encoding a gene product comprising an amino acid substitution at amino acid position 318 relative to the encoded protein in *P. acidipropionici* ATCC 55737 and positions relative to *P. acidipropionici* ATCC 4875 according to Table 1; and/or (iv) a copy number variation (e.g., an extra copy) of the whole RNA operon (SEQ ID NO: 18) relative to *P. acidipropionici* ATCC 4875 or ATCC 55737.

(v) a copy number variation (e.g., an extra copy) of the arginine deiminase regulon (SEQ ID NO: 19) with a deletion at position 37 (SEQ ID NO: 21) relative to *P. acidipropionici* ATCC 4875 or ATCC 55737.

In one embodiment an isolated *Propionibacterium* strain is provided, optionally a *P. acidipropionici* strain, comprising a gene sequence modified relative to a gene sequence selected from the group consisting of SEQ ID NO: 1, SEQ ID NO: 3 and SEQ ID NO: 4, or a sequence that shares 85%, 90%, 95% or 99% sequence identity with SEQ ID NO: 1, SEQ ID NO: 3 and SEQ ID NO: 4 but less than 100% sequence identity.

In one embodiment an isolated *Propionibacterium* strain is provided, optionally a *P. acidipropionici* strain, wherein the strain comprises (i) a modified large ribosomal RNA comprising the sequence of SEQ ID NO: 15, or a sequence having 95% or 99% sequence identity with same sequences in *P. acidipropionici* ATCC 4875 or ATCC 55737; and/or (ii) a modified long chain acyl-CoA synthetase comprising the sequence of SEQ ID NO: 17, or a polypeptide that differs from SEQ ID NO: 17 by 1, 2 or 3 amino acid substitutions; and/or (iii) a modified cation diffusion facilitator comprising the sequence of SEQ ID NO: 14, or a polypeptide that differs from SEQ ID NO: 14 by 1, 2 or 3 amino acid substitutions; and/or (iv) a copy number variation (e.g., an extra copy) of the whole RNA operon (SEQ ID NO: 17) relative to *P. acidipropionici* ATCC 4875 or ATCC 55737; and/or (v) a copy number variation (e.g., an extra) copy of the arginine deiminase regulon (SEQ ID NO: 20) with a deletion at position 37 relative to *P. acidipropionici* ATCC 4875 or ATCC 55737 that causes a frame shift. The deletion is located in one of the two domains.

In one embodiment, an isolated *Propionibacterium* strain is provided, optionally a *P. acidipropionici* strain, comprising a large subunit ribosome gene sequence of SEQ ID NO: 15, a long chain acyl-CoA synthetase gene sequence of SEQ ID NO: 16, and a cation diffusion facilitator gene sequence of SEQ ID NO: 13. In one embodiment, an isolated *P. acidipropionici* strain is provided comprising gene sequences encoding a large subunit ribosome RNA comprising SEQ ID NO: 15, a long chain acyl-CoA synthetase comprising SEQ ID NO: 17, and a cation diffusion facilitator comprising SEQ ID NO: 2.

In one embodiment an isolated *Propionibacterium* strain is provided, optionally a *P. acidipropionici* strain, wherein said strain comprises one or more duplication of proteins responsible for regulation of the arginine deiminase pathway, optionally in combination with one or more modified genes, relative to strain *P. acidipropionici* ATCC 4875, encoding for the large subunit ribosome, the long chain acyl-CoA synthetase, or the cation diffusion facilitator as disclosed above. In one embodiment the strains include any of the variations listed in Table 1. These include for example modifications to transcriptional regulators, transport, and genes linked to acid tolerance mechanisms. For example, additional *Propionibacterium* strains of the present disclosure in some embodiments include mutations in the transcriptional regulator MerR gene, the transcriptional regulator of the DeoR family, and/or the sigma 54 specific transcriptional regulator of the Fis family. Examples of mutations related to transport include a mutation in the Na+/H+ antiporter, the ABC transporter binding protein, the ABC-type nitrate/sulfonate/bicarbonate transport system, the arsenic efflux pump protein and the oligopeptide transport ATP-binding protein. In some embodiments, the *Propionibacterium* strains of the present disclosure include mutations in genes related to acid tolerance mechanisms such as a mutation in the malto-oligotreahalose trehalohydrolase and mutations in phosphogluconate dehydrogenase decarboxylating gene. Other mutations included dihydrolipoamide succinyltransferase component E2 of 2-oxoglutarate dehydrogenase complex/2-oxoglutarate dehydrogenase E1 component and D-3-phosphoglycerate dehydrogenase and mutations in the catalase/peroxidase gene.

In accordance with one embodiment a novel *P. acidipropionici* strain is provided selected from the group consisting of strains F3E8, F3G8, F3C8, F3H8, F3E9, F3F8, F3F6, F3D9, F3C1, F3B9, WGS.1, WGS.2, WGS.3, WGS.4, WGS.5, WGS.6, WGS 7, WGS.8, WGS.9, WGS.10, WGS.11, WGS.12, and WGS.13. In one embodiment the novel *P. acidipropionici* strain is selected from the group consisting of strains F3E8, F3G8, F3C8, F3H8, F3E9, F3F8, F3F6, F3D9, F3C1, and F3B9. In one embodiment the novel *P. acidipropionici* strain is selected from the group consisting of strains F3E8 and F3F6. In accordance with one embodiment a novel *P. acidipropionici* strain is provided selected from the group consisting of strains WGS.1, WGS.2, WGS.3, WGS.4, WGS.5, WGS.6, WGS 7, WGS.8, WGS.9, WGS.10, WGS.11, WGS.12, and WGS.13.

In accordance with one embodiment the novel strain is *P. acidipropionici* strain F3E8, deposited with the American Type Culture Collection (ATCC), 10801 University Boulevard, Manassas, Va., 20110-2209 USA on Jun. 25, 2015, and assigned ATCC Accession No. 122267. In accordance with one embodiment the novel strain is *P. acidipropionici* strain WGS 7, deposited with the American Type Culture Collection (ATCC), on Sep. 2, 2016 under ATCC Accession No. PTA 123476. Access to these deposits will be available during the pendency of the application to the Commissioner of Patents and Trademarks and persons determined by the Commissioner to be entitled thereto upon request. The deposits will be maintained in the ATCC Depository, which is a public depository, for a period of 30 years, or 5 years after the most recent request, or for the enforceable life of the patent, whichever is longer, and will be replaced if it becomes nonviable during that period. Applicant does not waive any infringement of their rights granted under this patent.

The present disclosure also encompasses derivatives of *P. acidipropionici* strains F3E8, F3C8, F3118, F3E9, F3F8, F3F6, F3D9, F3C1, F3B9, WGS.1, WGS.2, WGS.3, WGS.4, WGS.5, WGS.6, WGS 7, WGS.8, WGS.9, WGS.10, WGS.11, WGS.12, and WGS.13, formed by genomic shuffling with other known *P. acidipropionici* strains or wherein one or more genes of the parent strains have been modified to produce the derivative. In one embodiment the strains F3E8, F3C8, F3H8, F3E9, F3F8, F3F6, F3D9, F3C1 and F3B9 are subjected to one or more rounds of genetic shuffling with a different strain of *P. acidipropionici*. In one embodiment a derivative is formed by conducting genomic shuffling of one strain selected from the group consisting of strains F3E8, F3C8, F3H8, F3E9, F3F8, F3F6, F3D9, F3C1, F3B9, WGS.1, WGS.2, WGS.3, WGS.4, WGS.5, WGS.6, WGS 7, WGS.8, WGS.9, WGS.10, WGS.11, WGS.12, and WGS.13 and a second strain selected from either *P. acidipropionici* ATCC 4875 or *P. acidipropionici* ATCC 55737. In another embodiment a derivative is formed by conducting genomic shuffling between one strain selected from the group consisting of strains F3E8, F3C8, F3H8, F3E9, F3F8, F3F6, F3D9, F3C1, F3B9, WGS.1, WGS.2, WGS.3, WGS.4, WGS.5, WGS.6, WGS 7, WGS.8, WGS.9, WGS.10, WGS.11, WGS.12, and WGS.13 and a different strain selected from the group consisting of strains F3E8, F3C8, F3H8, F3E9, F3F8, F3F6, F3D9, F3C1, F3B9, WGS.1, WGS.2, WGS.3, WGS.4, WGS.5, WGS.6, WGS 7, WGS.8, WGS.9, WGS.10, WGS.11, WGS.12, and WGS.13. In one embodiment the derivative is formed by conducting genomic shuffling between one strain selected from the group consisting of strains F3E8, F3C8, F3118, F3E9, F3F8, F3F6, F3D9, F3C1 and F3B9 and a second different *P. acidipropionici* strain (i.e., not ATCC 4875, ATCC 55737, F3E8, F3C8, F3H8, F3E9, F3F8, F3F6, F3D9, F3C1 or F3B9). In one embodiment the derivative is formed by conducting genomic shuffling between strain F3E8 and a second different *P. acidipropionici* strain.

In accordance with one embodiment strains F3E8, F3G8, F3C8, F3H8, F3E9, F3F8, F3F6, F3D9, F3C1 and F3B9 are further modified to reduce the production of byproducts such as acetate and succinate. The production of these byproducts not only lowers the yield of the main fermentation product but also causes difficulty in product purification.

In accordance with one embodiment, a method for the commercial production of propionic acid or one of its derivatives such as propanol or propylene is provided comprising batch fermentation utilizing the novel *Propionibacterium acidipropionici* disclosed herein. In accordance with one embodiment, the primary substrates for the fermentation are sucrose and/or glucose. In one embodiment the primary nitrogen source will be gaseous ammonia that is supplemented with an amino acids/protein cocktail from plant derived flour (soy flour, cotton seed flour, corn steep flour, etc.). However, other nitrogen sources are known to those skilled in the art and are suitable for use in the disclosed methods.

In one embodiment the method for producing propionic acid or one of its derivatives such as propanol or propylene is provided. The method comprises the steps of culturing a *P. acidipropionici* strain as disclosed herein under conditions suitable for growth of the strain and recovering the propionic acid produced by said strain. In one embodiment the cultured *P. acidipropionici* strain is an isolated or purified *P. acidipropionici* strain wherein said strain has a maximum growth rate of at least 0.24/hr as calculated for the exponential phase of cells cultured at 32° C., pH 6.5 in an acceptable media such as PAM. In one embodiment the cultured *P. acidipropionici* strain is an isolated or purified *P. acidipropionici* strain wherein the strain has a maximum growth rate at least 1.5 times that of *P. acidipropionici* ATCC strain 4875. In one embodiment the cultured *P. acidipropionici* strain is an isolated or purified *P. acidipropionici* strain wherein said strain has an increase of 15 to 20% in total yield (g/g) of propionic acid relative to that produced by *P. acidipropionici* ATCC strain 4875, and optionally has a maximum growth rate at least 1.5 times that of *P. acidipropionici* ATCC strain 4875 when both strains are cultured under identical anaerobic conditions, optionally at 32° C., pH 6.5 in an acceptable media such as PAM. In one embodiment the cultured *P. acidipropionici* strain is an isolated or purified *P. acidipropionici* strain wherein the strain has a propionic acid yield of about 0.55 or 0.66 g/g, and optionally has a maximum growth rate at least 1.5 times that of *P. acidipropionici* ATCC strain 4875 when both strains are cultured under identical anaerobic conditions, optionally at 32° C., pH 6.5 in an acceptable media such as PAM. In one embodiment the cultured *P. acidipropionici* strain is an isolated or purified *P. acidipropionici* strain wherein the strain produces about 0.84 g/L/hr of propionic acid, and optionally has a maximum growth rate of at least 0.24/hr as calculated for the exponential phase of cells cultured at 32° C., pH 6.5 in an acceptable media such as PAM.

In one embodiment the cultured *Propionibacterium* strain, optionally a *P. acidipropionici* strain, comprises
  (i) a modified large ribosomal RNA comprising a nucleotide substitution of the large ribosomal gene at positions according to Table 1;
  (ii) a modified long chain acyl-CoA synthetase gene comprising a nonsense codon according to Table 1; and
  (iii) a modified cation diffusion facilitator gene encoding a gene product comprising an amino acid substitution at amino acid position 318 relative to the same gene in *P. acidipropionici* ATCC 55737 and positions as shown in Table 1 relative to *P. acidipropionici* ATCC 4875. In one embodiment the cultured *Propionibacterium* strain, optionally a *P. acidipropionici* strain, comprises a modified gene sequence relative to a gene sequence selected from the group consisting of SEQ ID NO: 1, SEQ ID NO: 3 and SEQ ID NO: 4, or a sequence that shares 85%, 90%, 95% or 99% sequence identity with SEQ ID NO: 1, SEQ ID NO: 3 and SEQ ID NO: 4 but less than 100% sequence identity. In one embodiment the cultured *P. acidipropionici* strain comprises modified gene sequences relative to each of the gene sequences SEQ ID NO: 1, SEQ ID NO: 3 and SEQ ID NO: 4, or a sequence that shares 85%, 90%, 95% or 99% sequence identity with SEQ ID NO: 1, SEQ ID NO: 3 and SEQ ID NO: 4, but less than 100% sequence identity;
  (iv) a copy number variation (e.g., an extra copy) of the whole RNA operon (SEQ ID NO: 18) relative to *P. acidipropionici* ATCC 4875 or ATCC 55737; and/or
  (v) a copy number variation (e.g., an extra copy) of the arginine deiminase regulon (SEQ ID NO: 20) with a deletion at position 37 relative to *P. acidipropionici* ATCC 4875 or ATCC 55737 that causes a frame shift. The deletion is located in one of the two domains.

In one embodiment the cultured *P. acidipropionici* strain is an isolated or purified *P. acidipropionici* strain selected from the group consisting of strains F3E8, F3C8, F3H8, F3E9, F3F8, F3F6, F3D9, F3C1, F3B9, WGS.1, WGS.2, WGS.3, WGS.4, WGS.5, WGS.6, WGS 7, WGS.8, WGS.9, WGS.10, WGS.11, WGS.12, and WGS.13 or from strains F3E8, F3G8, F3C8, F3H8, F3E9, F3F6, F3D, and F3C1, or from strains WGS 7, F3E8 and F3F6. In one embodiment the cultured *P. acidipropionici* strain is isolated or purified *P. acidipropionici* strain F3E8, deposited under ATCC Accession No. 122267. In accordance with one embodiment the novel strain is *P. acidipropionici* strain WGS 7, deposited with the American Type Culture Collection (ATCC), on Sep. 2, 2016 under ATCC Accession No. PTA 123476.

EXAMPLE 1

Use of Genome Shuffling (GS) to Prepare New Strains of *Propionibacterium acidipropionici*

*Propionibacterium* sp are pleomorphic rods, gram-positive bacteria that naturally produce PA as their main fermentation product through the Wood-Werckman cycle. Natively, PA is produced along with other organic acids (lactate, succinate, and acetate) resulting in low productivities and modest yields which translate in costly downstream processes. Until recently, metabolic engineering in *P. acidipropionici* had proven challenging mainly due to the seven Clustered Regularly Interspaced Short Palindromic Repeats (CRISPRs) which provide resistance against conjugative plasmids and bacteriophages. Therefore genome shuffling (GS) was used to improve the growth rate and PA production of *P. acidipropionici*, obtaining a strain that can achieve improved yields and higher growth rates.

In addition, to understand genomic changes leading to the improved phenotype, next generation sequencing (NGS) was used to characterize genotypic changes. Using ClonalFrame (Didelot and D. Falush, Genetics, 2007, 175, 1251-66), changes in the genome are shown to correspond to regions of high recombination probability, thus, reinforcing the mechanism of gene conversion during GS. GS in bacteria has mainly been linked to gene conversion (asymmetric contributions) where the donor provide a small amount of DNA material leaving the rest of the recipient intact.

Material and Methods

Bacteria. *P. acidipropionici* ATCC 4875 and *P. acidipropionici* ATCC 55737 were selected from a collection of 17 strains (Stowers et al., J. Ind. Microbiol. Biotechnol., 2014, 41, 837-852) for their fast growth and ability to achieve high PA yields. The strains were kept at −80° C. using glycerol (20%) as cryoprotector.

Media. The culture media (PAM) for pre-inoculum preparation consisted of yeast extract (10 g/L), trypticase soy (5 g/L), $K_2HPO_4$ (0.05 g/L), $MnSO_4$ (0.05 g/L), and glucose (40 g/L). Agar (15 g/L) was added only to prepare PAM plates. Glucose (100 g/L) was used as the carbon source. Media components and the carbon source were sterilized separately for 20 min at 121° C.

Protoplast formation buffer (PFB). This buffer consisted of sodium succinate (40.5 g/L), sucrose (42.75 g/L), and $MgCl_2$ (1.9 g/L) dissolved in one litre of Tris-HCl 0.05 mol/L at pH 7.1.

Regeneration buffer (RB). This buffer consisted of yeast extract (10 g/L), trypticase soy (5 g/L), $KH_2PO_4$ (1.5 g/L), $K_2HPO_4$ (2.5 g/L), and Bovine Serum Albumin (BSA) (5 g/L) adjusted to pH 7.

Analytical methods. The optical density of the culture was measured at 600 nm using a Biochrom Libra S12 UV/Vis Spectrophotometer. Organic acids, carbohydrates, and alcohol were quantified by ion-exclusion chromatography using an Agilent 1200 HPLC system and an Agilent Hiplex H column (300×7.7 mm, PL1170-6830) with a guard column (SecurityGuard Carbo-H, Phenomenex PN: AJO-4490).

Sugars and alcohols were monitored using a refractive index detector (Agilent RID, G1362A) set on positive polarity and optical unit temperature of 40° C., while organic acids were monitored at 210 nm (Agilent MWD, G1365B). 30 uL of sample was injected onto the column using an auto-sampler (Agilent HiP-ALS, G1367B) and column temperature kept at 65° C. using a thermostatted column compartment (Agilent TCC, G1316A). Analytes were eluted isocratically with 4 mM $H_2SO_4$ at 0.6 mL/min for 26 min. Chromatograms were integrated using ChemStation (Rev B.03.02[341]).

Inoculum preparation. Under sterile conditions, bacteria activation was carried out in a 1.5 mL Eppendorf tube with 1 mL of PAM media inoculated with 0.8% (v/v) of a glycerol stock. This culture was allowed to grow for 24 hours at 32° C. The cultures were transferred to a 15 mL Falcon tube containing 14 mL of PAM media and allowed to grow for an additional 24 hours. 5% (v/v) of this culture was used to inoculate 250 mL serum bottles containing 100 mL of PAM media and allowed to grow for an additional 24 hours. Cells from the serum bottles in mid-exponential phase were used to inoculate the fermenters at an initial OD600 nm of 0.3.

Protoplast preparation and regeneration. Protoplasts were prepared as described in Guan et al. (Guan et al., J. Biotechnol., 2013, 167, 56-63) with minor modifications. Cells were grown for 24 hours in PAM media supplemented with 40 g/L of glucose and 1% of glycine. Cells were then conditioned in PAM media containing 1% of glycine and 120 g/L of glucose for an extra 24 hours. After at least ten generations, cells were washed two times using PBS and fixed to an OD600 nm=0.2 in a lysozyme solution containing 15 mg/mL-600,000 U/mL-lysozyme solution in PFB. Cell walls were digested for two hours at 120 rpm and 40° C. Protoplasts were detected using a light microscope using the 100× oil immersion objective and counted using a haemocytometer. When appropriate, protoplasts were regenerated in RB (pH=7 for 48 h at 32° C.).

Genome shuffling (GS). The protocol from Guan et al (Guan et al., J. Biotechnol., 2013, 167, 56-63) was used with some modifications. Protoplasts were treated with UV light for 0.5 min or heated at 60° C. for 2 h. Cells were mixed, centrifuged and re-suspended in 500 μL of PFB. Then 500 uL of PEG 6000 (80%) with 20 mmol/L $CaCl_2$ was added. Fusion conditions were conducted at pH 7.4, 32° C. for 30 min. After fusion, 5 mL of PFB was added, and the suspension was centrifuged at 2500 rpm for 5 min. Protoplasts were washed two times with 5 mL of PFB and re-suspended in 1 mL of RB.

Screening. On a first stage, PAM media plates were used to screen for strains with improved growth rate. PAM plates were incubated in an anaerobic chamber at 32° C. and monitored for 24 hours every 6 hours. The first colonies on the plate were labeled and selected for the next round of GS. After three rounds of GS, isolated colonies were randomly selected for screening in 96-well plates containing 100 μL of PAM media. Growth was monitored using a micro-plate reader Omega FLUOstar® adapted to maintain anaerobic conditions through a constant injection of nitrogen. The best performing strains were scaled up to 250 mL serum bottles with a working volume of 100 mL under $N_2$. Serum bottles were incubated using an orbital shaker incubator (Infors HT multitron standard) with an agitation rate of 100 rpm and a working temperature of 32° C. for 96 hours.

Instrumented fermenters. Fermentations were performed using 2 L Applikon fermenters with a working volume of 1 L. Fermenters were equipped with probes and controllers for pH, dissolved oxygen, temperature, and agitation. The agitation rate was controlled with two Rushton impellers at 300 rpm. The pH was controlled at 6.5 using 10 M NaOH. The temperature of the culture was maintained at 32° C. using an electric jacket. Prior to inoculation, the fermenters were sparged with $N_2$ for at least 15 minutes. A constant $N_2$ flow was kept for the entire fermentation at a flow rate of 0.3 L/min.

Fermentation calculations. Maximum specific growth rate ($\mu_{max}$) was calculated in exponential phase. For consistency, volumetric productivity (Pv) was calculated for the same time interval (ranging from 22.5 to 52 hours). Yield (Yps) was calculated using the total PA produced over the total substrate consumed. Finally, ratios PA: Acetic Acid and PA:Succinic Acid were calculated using total organic acid production.

DNA-sequencing and de novo assembly. Genomic DNA of the different *Propionibacterium* strains were extracted using PureLink® genomic DNA mini kit (Invitrogen Cat. No. K1820-01) and quantified using Nanodrop 1000 (Thermo Scientific) and Qubit® dsDNA BR assay kit (Life Technologies Cat. No. Q32850). Quality of the DNA was determined by running a 1% agarose gel with DNA gel stain SYBR safe (Life Technologies Cat. No. S33102). The gel was visualized in a ChemiDoc MP system (Bio-Rad). The Illumina platform was used to sequence the genomes of 11 strains (n=1 parental strain *P. acidipropionici* ATCC 55737 and n=10 strains from GS). Sequencing was performed using TrueSeq® Illimina 300 PE. Library were prepared using Illumina TrueSeq® DNA HT sample preparation kit (illumina Cat. No. FC-121-2003). The assembly of the reads was performed using the SPAdes genome assembly algorithm (Bankevich et al., Comput. Biol., 2012, 19, 455-477. To close the genomes, two strains (the parental strain *P. acidipropionici* ATCC 55737 and the recombinant *P. acidipropionici* F3E8) were sequenced using PacBio RS II technology. The PacBio® library preparation was performed using the protocol for 20 Kb selected with the BluePippin™ system. The sequencing chemistry was the most recent released P6-C4 by PacBio and loaded by magnetic beads. The genome assembly was performed with the SMRT® portal.

Bioinformatics tools. RAST server was used to annotate the different assembled genomes (Aziz et al., BMC Genomics, 2008, 9, 75). Mauve software was used to perform a multiple whole genome alignments. Mauve was also used to move the contigs of the strains from GS taking as a reference the closed genome *P. acidipropionici* F3E8 (Darling et al., Genome Res., 2004, 14, 1394-403). GRIL was used to find rearrangements in the Mauve alignment (Darling et al., Bioinformatics, 2003, 20, 122-124). Genome-to-genome distance calculator (GGDC 2.0) was used to calculate the genome distance between two genomes (Auch et al., Genomic Sci., 2010, 2, 142-148). Bowtie2 and SAMtools or SMRT® portal were used to align the reads and call the variants of the sequenced genomes. SnpEff was used to annotate the variations and SnpSift to filter them (Cingolani et al., Front. Genet., 2012, 3, 35. IGV viewer was used to visualizing the variations. ClonalFrame, was used to determine the number of homologous recombination events in the recombinants. Bio-Python programming language was used to develop a script to perform a Blast gene-gene differential and score system comparison between two genomes (Altschul et al., J. Mol. Biol., 1990, 215, 403-10).

Results

Screening of Superior Strains.

Figure 1B:
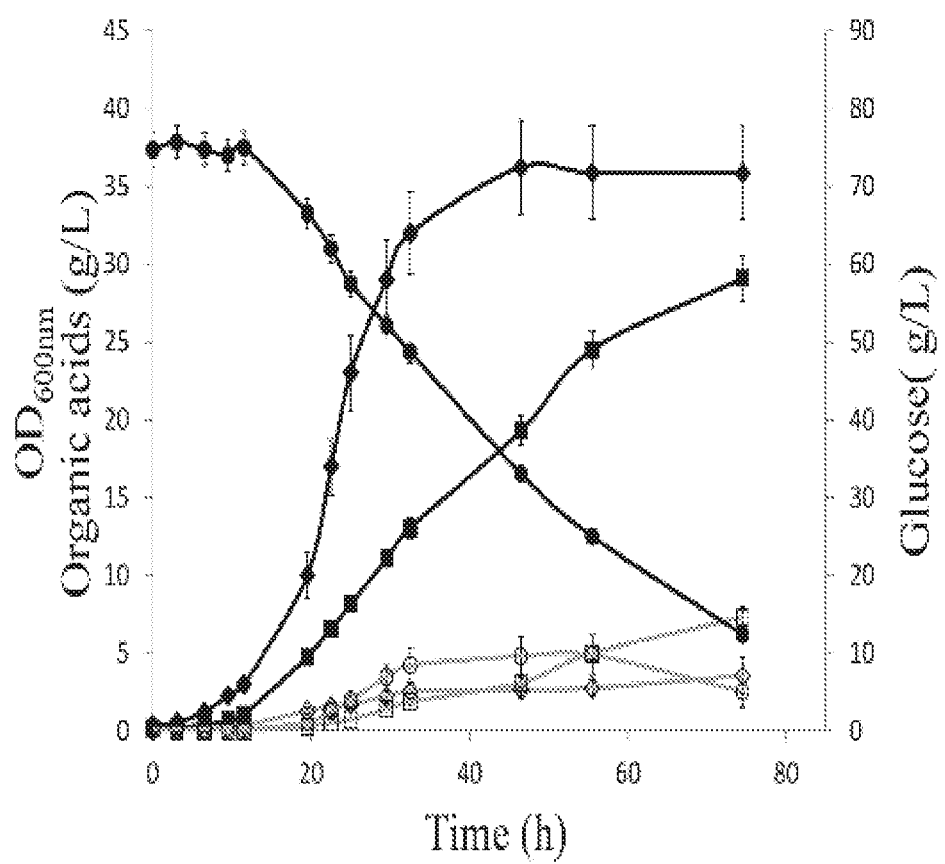
Figure 1C:
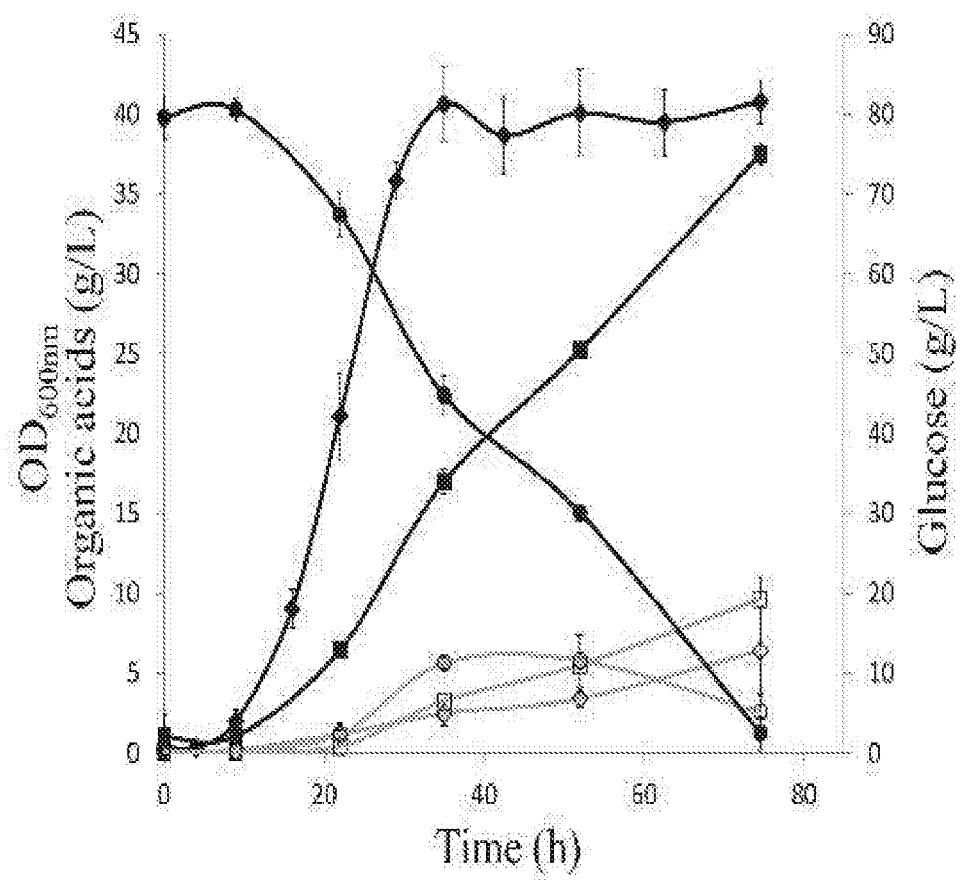

To increase PA production using GS, *P. acidipropionici* ATCC 4875 and *P. acidipropionici* ATCC 55737 were selected as the initial strains. After GS, colonies were selected using high-throughput micro kinetics to select strains with higher growth rate. The growth rate of the new colonies was compared to the growth rate of the parental strains (grown on the same plate). From each plate, the 10 fastest growing colonies were grown in serum bottles. One of the fastest growing strains (referred hereafter as F3E8) out of the lot of 10 strains was characterized on bioreactors (FIG. 1C). The new strain displayed a growth rate of 0.26 $h^{-1}$ compared to the growth rate of the parental strains of 0.15 $h^{-1}$ and 0.18 $h^{-1}$ (Table 2) which is in accordance with the growth rate observed in serum bottles (Table 3).

TABLE 2

Kinetic parameters of the 2 L instrumented fermentations to test the stability of the parental strains *Propionibacterium acidipropionici* ATCC 4875 and *Propionibacterium acidipropionici* ATCC 55737, and the new strain from GS *Propionibacterium acidipropionici* F3E8. PA:SA is the PA titer divided by the SA titer at the end of the fermentation. PA:AA is the PA titer divided by the AA titer at the end of the fermentation.

| Strain | Yps (g/g) | PA:SA (g/g) | PA:AA (g/g) | *$P_v$ (g/L.h) | μ (1/h) |
|---|---|---|---|---|---|
| *P. acidipropionici* ATCC 4875 | 0.45 ± 0.01 | 3.87 ± 0.76 | 4.77 ± 0.89 | 0.61 ± 0.01 | 0.15 ± 0.001 |
| *P. acidipropionici* ATCC 55737 | 0.43 ± 0.02 | 3.44 ± 0.0.3 | 7.83 ± 0.1 | 0.64 ± 0.01 | 0.18 ± 0.02 |
| *P. acidipropionici* F3E8 | 0.55 ± 0.02 | 3.51 ± 0.39 | 5.76 ± 1.33 | 0.84 ± 0.02 | 0.26 ± 0.01 |

*Range of time: 22.5-52 h

TABLE 3

Genomic and kinetic features of the propionibacteria strains

| Strain | Genome size (Mb) | Project | No. of Contigs | % GC | CDS | Maximum Specific growth rate ($h^{-1}$) |
|---|---|---|---|---|---|---|
| *P. acidipropionici* ATCC 4875[1] | 3.66 | ● | 1 | 68.8 | 3362 | 0.15 ± 0.004 |
| *P. acidipropionici* ATCC 55737[2] | 3.71 | ● | 1 | 68.7 | 3406 | 0.18 ± 0.003 |
| *P. acidipropionici* F3E8[3] | 3.63 | ● | 1 | 68.7 | 3350 | 0.26 ± 0.001 |
| *P. acidipropionici* F3G8[3] | 3.58 | ◐ | 357 | 68.6 | 3301 | 0.24 ± 0.007 |
| *P. acidipropionici* F3C8[3] | 3.61 | ◐ | 333 | 68.6 | 3347 | 0.25 ± 0.007 |
| *P. acidipropionici* F3H8[3] | 3.57 | ◐ | 381 | 68.7 | 3296 | 0.25 ± 0.014 |
| *P. acidipropionici* F3E9[3] | 3.61 | ◐ | 218 | 68.6 | 3327 | 0.25 ± 0.007 |
| *P. acidipropionici* F3F8[3] | 3.61 | ◐ | 255 | 68.7 | 3329 | 0.24 ± 0.007 |
| *P. acidipropionici* F3F6[3] | 3.59 | ◐ | 212 | 68.7 | 3312 | 0.26 ± 0.014 |
| *P. acidipropionici* F3D9[3] | 3.58 | ◐ | 180 | 68.7 | 3302 | 0.25 ± 0.007 |
| *P. acidipropionici* F3C1[3] | 3.59 | ◐ | 400 | 68.7 | 3305 | 0.25 ± 0.007 |
| *P. acidipropionici* F3B9[3] | 3.62 | ◐ | 447 | 68.7 | 3325 | 0.24 ± 0.003 |

[1]Genome sequence downloaded from the NCBI web page (NC_019395.1).
[2]Strain in-house sequenced, assembled, and annotated.
[3]Recombinants obtained from genome shuffling between *P. acidipropionici* ATCC 4875 and *P. acidipropionici* ATCC 55737. The specific growth rate data are the average of two biological replicates in serum bottles.
● Genome closed
◐ Genome not closed.

At the end of the fermentation, F3E8 had produced 40 g/L of PA compared to the parental strains which produced 30 g/L (72 hours of fermentation) (FIG. 1A-1C) resulting in a global improvement of 25% in PA production. In terms of volumetric productivity, the new strain displayed an improvement of 27% relative to the best parental strain. In terms of yield (Yps) the new strain had a yield of 0.55 g/g compared to the 0.44 g/g yield for the best parent representing an increase of 20% in yield.

Discussion

Genome shuffling has been extensively used in industry to increase bacterial phenotypes. As reported herein, two distinct strains that displayed strong genomic differences were used as parental strains for genome shuffling (GS). Comparative analysis of strains produced by GS showed that recombination only happens between highly conserved genes of these two strains. After three rounds of GS using *P. acidipropionici* ATCC 4875 and *P. acidipropionici* ATCC 55737, 10 mutants with increased growth rate and PA production were obtained.

EXAMPLE 2

Serum Bottle *P. acidipropionici* F3E8 Fermentations
Material and Methods

Bacteria. *P. acidipropionici* F3E8 obtained from genome shuffling disclosed in Example 1 was used to perform the kinetic evaluations in serum bottles. The strain was taken from glycerol (20%, v/v) stock kept at −80° C.

Media. The culture media (PAM) for pre-inoculum preparation consisted of yeast extract (10 g/L), trypticase soy (5 g/L), $K_2HPO_4$ (0.05 g/L), $MnSO_4$ (0.05 g/L), and glucose (40 g/L). Media components and the carbon source were sterilized separately for 20 min at 121° C. in an autoclave.

Serum bottles. 250 mL serum bottles with 100 mL of working volume with PAM media were used. The carbon source and media were sterilized inside the serum bottles separately and mixed under sterile conditions. After autoclaving, the head space of the serum bottles was washed with sterile nitrogen. The serum bottles were incubated in an orbital incubator at 32° C. and 90 rpm for 96 h.

Inoculum preparation. 1.5 mL Eppendorf tubes containing 1 mL of PAM media were inoculated with 0.8% (v/v) of a F3E8 glycerol stock under sterile conditions to perform the first step of the cultivation. This culture was allowed to grow for 24 hours at 32° C. The cultures were then transferred to a 15 mL Falcon tube containing 14 mL of PAM media and allowed to grow for an additional 24 hours. 5% (v/v) of this culture was used to inoculate 250 mL serum bottles containing 100 mL of PAM media and allowed to grow for an additional 24 hours. Cells from the serum bottles in mid-exponential phase were used to inoculate other serum bottles to an OD600 nm of 0.3.

Analytical methods. The optical density of the culture was measured at 600 nm using a Biochrom Libra S12 UV/Vis Spectrophotometer. Organic acids and carbohydrates were quantified by ion-exclusion chromatography using an Agilent 1200 HPLC system and an Agilent Hiplex H column (300×7.7 mm, PL1170-6830) with a guard column (SecurityGuard Carbo-H, Phenomenex PN: AJO-4490).

Figure 2:
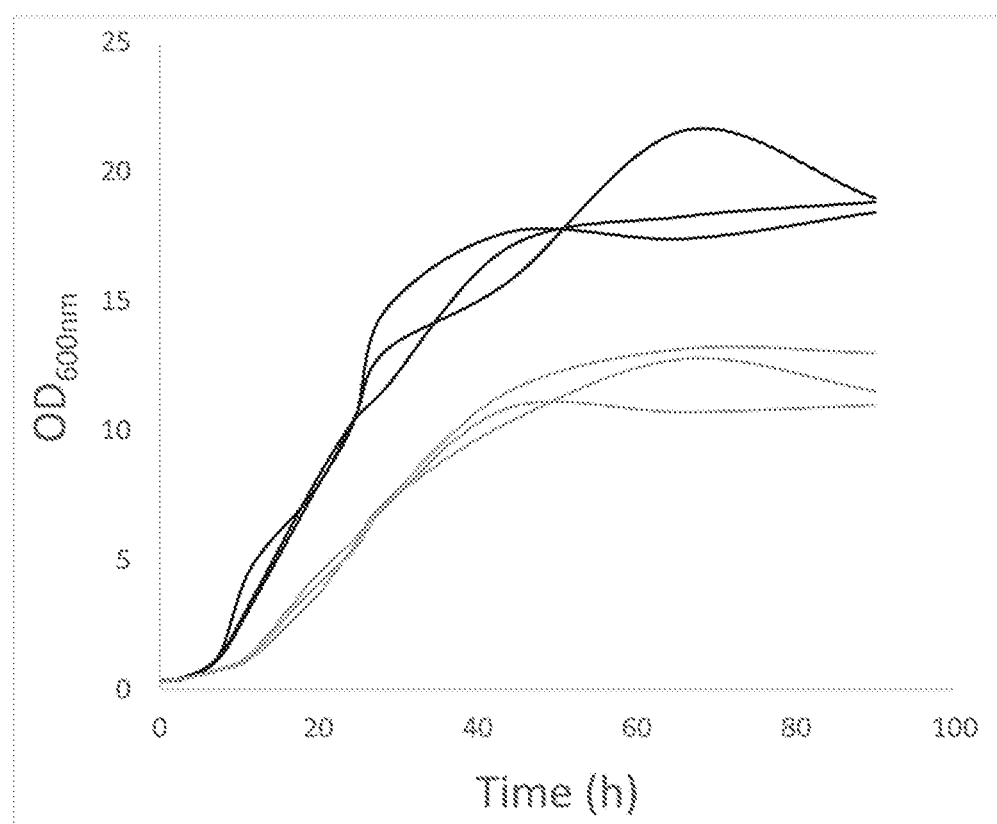
FIG. 2 is a graph demonstrating the fermentation growth profile of *P. acidipropionici* F3E8 in serum bottles (three biological replicates).

Results. FIG. 2 shows the growth profile of *P. acidipropionici* F3E8 and Table 4 shows the corresponding fermentation performance parameters. As can be seen, the maximum specific growth rate was around 0.26 h and the final PA production was around of 10.35 g/L. The PA conversion (Yps yield) was around 0.66 g/g. As byproducts, there were detected around 0.23 g/L of succinic acid (SA) and 1.29 g/L of acetic acid (AA).

trations were established by double dilution with the stock PA solution at 100 g/L. The micro-plates were incubated in a micro-plate reader OMEGA Fluostar adapted to maintain anaerobic conditions. The micro-plate was incubated at 32° C. for 72 h. Finally, the maximum specific growth rates were calculated using GrowthRates program (Hall et al., Mol. Biol. Evol., 2014, 31, 232-238).

Figure 3A:
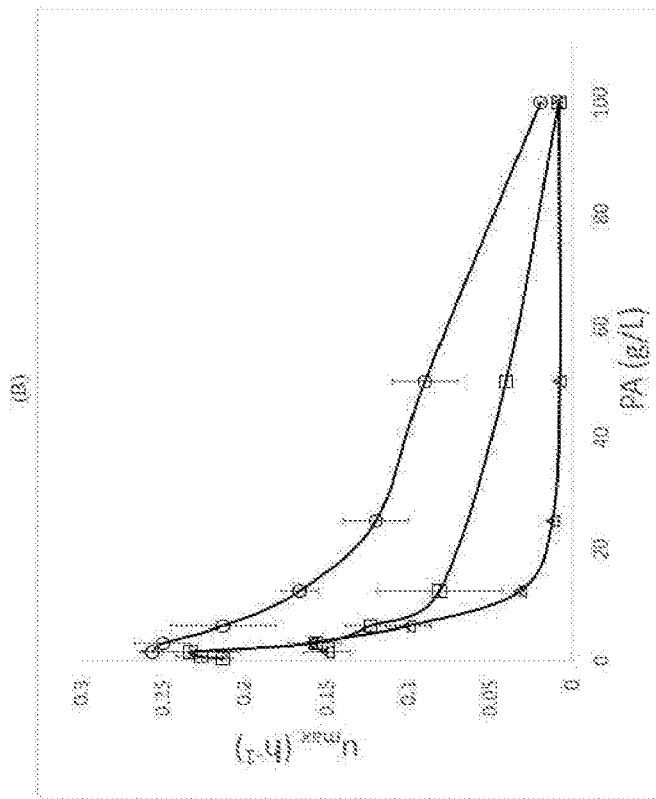
FIGS. 3A & 3B are graphs demonstrating the kinetics of PA inhibition at different pHs (○: pH 6.5. □: pH 5.5. Δ: pH 4.5).
Figure 3B:
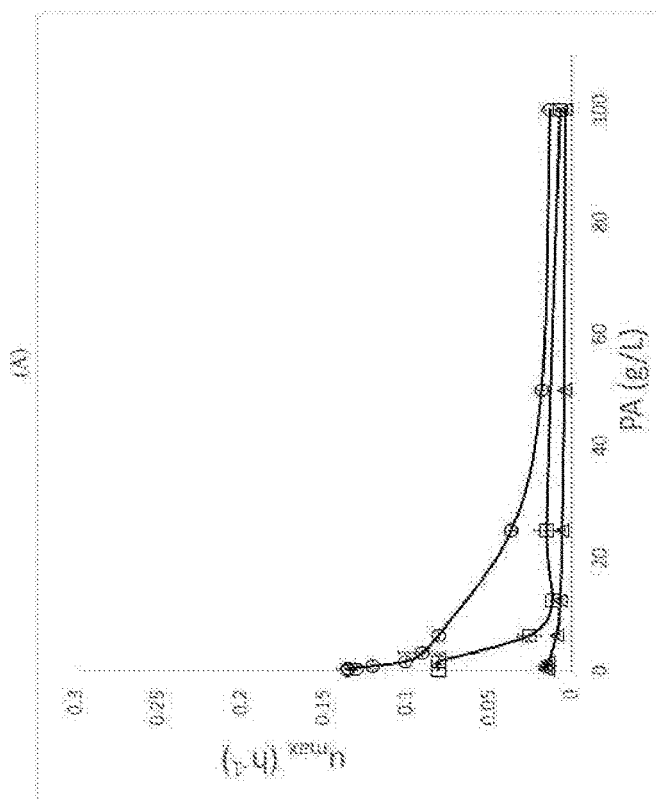

Results. FIGS. 3A-3B show the specific growth rate profile at different acidic conditions for the strains. As can be seen in the charts, the growth rate was inhibited in both strains as the PA concentration was increased. Nevertheless, the inhibition pattern was more severe for the strain *P. acidipropionici* ATCC 4875 (FIG. 3A) than for the mutant strain *P. acidipropionici* F3E8 (FIG. 3B). The minimum inhibitory condition (MIC) for *P. acidipropionici* F3E8 was

TABLE 4

Parameters of the serum bottle kinetics to test growth rate and production of the mutant from genome shuffling *P. acidipropionici* F3E8.

| Strain | PA (g/L) | SA (g) | AA (g) | Yps (g/g) | μ (1/h) |
| --- | --- | --- | --- | --- | --- |
| *P. acidipropionici* F3E8 | 10.35 ± 0.070 | 0.23 ± 0.005 | 1.29 ± 0.044 | 0.66 ± 0.0023 | 0.26 ± 0.005 |

Discussion. The results indicate that the efficiency of *P. acidipropionici* F3E8 to convert PA from glucose is above 0.6 g/g.

EXAMPLE 4 pH and Propionic Acid Tolerance in *P. acidipropionici* ATCC 4875 and *P. acidipropionici* F3E8

To compare acid tolerance between *P. acidipropionici* ATCC 4875 and *P. acidipropionici* F3E8, the cells were grown in a 96-well plates at different pH values (6.5, 5.5, and 4.5) and different propionic acid (PA) concentrations (100, 50, 25, 12.5, 6.25, 3.125, 1.56, 0.78, and 0). The growth was constantly monitored in a micro-plate reader for three days.

Material and Methods

Bacteria. *P. acidipropionici* ATCC 4875 and *P. acidipropionici* F3E8 were used. The strains were kept at −80° C. using glycerol (20%, v/v) as cryoprotector.

Media. The culture media (PAM) for pre-inoculum preparation consisted of yeast extract (10 g/L), trypticase soy (5 g/L), $K_2HPO_4$ (0.05 g/L), $MnSO_4$ (0.05 g/L), and glucose (40 g/L). Media components and the carbon source were sterilized separately for 20 min at 121° C. in an autoclave. The pH was adjusted using 5 M HCl and sodium propionate was used to prepare a stock of 100 g/L of PA.

Inoculum preparation. 1.5 mL Eppendorf tubes containing 1 mL of PAM media were inoculated with 0.8% (v/v) of an F3E8 glycerol stock under sterile conditions to perform the first step of the cultivation. This culture was allowed to grow for 24 hours at 32° C. The cultures were transferred to a 15 mL Falcon tube containing 14 mL of PAM media and allowed to grow for an additional 24 hours. Cells in mid-exponential phase were used to inoculate the micro-plates to an OD600 nm from 0.2 to 0.3.

Micro kinetics. 96 well-plates were used to test the growth rate of the strain at different acidic conditions. The working volume of each well was 100 uL. The kinetics were studied in duplicate. Three pHs (6.5, 5.5, and 4.5) were tested at different PA acid concentrations (100, 50, 25, 12.5, 6.25, 3.125, 1.56, 0.78, and 0). First, respective rows were filled with 100 uL of PAM at the different pHs. The PA concenpH 4.5 and PA 25 g/L meanwhile the MIC for *P. acidipropionici* ATCC 4875 was pH 6.5 and 50 g/L.

EXAMPLE 5

Propionibacteria Sequencing, De Novo Assembly, and Annotation.

The genome of *P. acidipropionici* ATCC 4875 has previously been sequenced and annotated (Parizzi et al., BMC Genomics, 2012, 13, 562). *P. acidipropionici* ATCC 55737 and 10 GS strains were sequenced using TruSeq Illimina 300 base pair paired end sequencing. To close the genome, the recombinant *P. acidipropionici* F3E8 and the parental *P. acidipropionici* ATCC 55737 were also sequenced using PacBio RS II. RAST and the SEED viewer were used for genome annotation (Aziz et al., BMC Genomics, 2008, 9, 75; Overbeek et al., Nucleic Acids Res., 2005, 33, 5691-5702).

*P. acidipropionici* ATCC 55737 has a genome of 3.71 Mb, a GC content of 68.7%, 3406 CDS (42% in a subsystem), and 65 RNAs. The new strain from GS named *P. acidipropionici* F3E8 has a size of 3.63 Mb, 68.7% of GC content, 3350 CDS (43% in a subsystem), and 73 RNAs. The other nine strains from GS have similar genome features as the strain *P. acidipropionici* F3E8 (Table 3). As can be seen, the genome size of the strains from GS is similar to the parental strain *P. acidipropionici* ATCC 4875. Surprisingly, the number of RNAs in the recombinants is 11% higher than the parentals strains.

Genome Association Between *P. acidipropionici* ATCC 4875 and *P. acidipropionici* ATCC 55737.

In order to elucidate the relationship between phenotype and genotype, a systematic genomic comparison between *P. acidipropionici* ATCC 4875 and *P. acdipropionici* ATCC 55737 was performed. These two strains display distinct specific growth rates. First, a gene-gene comparison to determine gene presence, absence, and similarity was performed. This comparison suggests that *P. acidipropionici* ATCC 4875 has 345 unique genes and *P. acidipropionici* ATCC 55737 has 423 unique genes (E. value <0.0001). All the genes involved in PA production were conserved within 98%. (E-value <0.0001). PA is produced through the Wood- Werckman cycle which involves ten genes: methylmalonyl-CoA carboxyl-transferase (two subunits), malate dehydrogenase, fumarate hydratase, succinate dehydrogenase (two subunits), propionyl-CoA: succinate CoA-transferase, methyl-malonyl-CoA epimerase and methylmalonyl-CoA mutase (two subunits).

Major changes between the two strains were observed for the subsystem "prophages". Prophages are mobile elements which help bacteria cope with adverse environmental conditions such as sub-lethal concentration of antibiotics or with—standing osmotic, oxidative, and acid stresses. An increased number of prophages has previously been reported to have an effect on growth and biofilm formation. *P. acidipropionici* ATCC 55737 presents 30 prophages-associated proteins with a total size of 33,000 bp, whereas *P. acidipropionici* ATCC 4875 has only 17 prophages-associated proteins with a total size of 20,143 bp; Out of those, 11 are shared between the two strains.

Genome Comparisons

In an effort to compare the new strains obtained through GS, we aligned the genomes of the new strains using Mauve; *P. acidipropionici* ATCC 4875 was selected as the reference. The analyses showed 38 LCBs, of which four are inversions and 11 are rearrangements. The alignment shows increased similarity to the parental *P. acidipropionici* ATCC 55737 compared to *P. acidipropionici* ATCC 4875. To calculate similarities, the genomic distance was used to calculate differences between the recombinant strains and the parents using GGDC 2.0.[24] This comparison suggest that the recombinants have a genomic distance of 0.1090±0.0013 using as a reference *P. acidipropionici* ATCC 4875 and 0.0156±0.0019 using *P. acidipropionici* ATCC 55737 as a reference.

Variant Analysis

Bowtie2 and SAMtools, or SMRT® were used to align reads and to call for variants between the new strains and the parents. SNPeff was used to annotate variations. The variant analyses were performed against *P. acidipropionici* ATCC 55737. Significant variations are presented in Table 1. Many of the mutations, while not in the same genes, were part of the same functional group of genes which included most notably transcriptional regulators, transport, and genes linked to acid tolerance mechanisms. For example, the strain *P. acidipropionici* F3B9 had a mutation in the transcriptional regulator MerR gene, whereas the strain *P. acidipropionici* F3D9 had two mutations in regulatory genes: one in the transcriptional regulator of the DeoR family, and the other in the sigma 54 specific transcriptional regulators of the Fis family. Several mutations related to transport were also found. For instance, the recombinant *P. acidipropionici* F3G9 had a mutation in the $Na^+/H^+$ antiporter, whereas the strain *P. acidipropionici* F3E8 had a mutation in one ABC transporter binding protein and the strain *P. acidipropionici* F3G8 had one mutation in the ABC-type nitrate/sulfonate/bicarbonate transport system and another one in the arsenic efflux pump protein; finally *P. acidipropionici* F3C8 had a mutation in the oligopeptide transport ATP-binding protein. Mutations in genes related to acid tolerance mechanisms included a mutation in the malto-oligotreahalose trehalohydrolase in the strain *P. acidipropionici* F3B9 and two mutations in phophogluconate dehydrogenase decarboxylating gene in the *P. acidipropionici* F3F6. Other mutations included dihydrolipoamide succinyltransferase component E2 of 2-oxoglutarate dehydrogenase complex/2-oxoglutarate dehydrogenase E1 component and D-3-phosphoglycerate dehydrogenase and mutations in the catalase/peroxidase gene.

Out of all the individual variations, only three were conserved in all 10 strains. The first SNP was identified in the large subunit ribosomal RNA, the second one in the cation diffusion facilitator protein and the last one in the long chain fatty acyl-CoA synthetase. Having a closed genome using PacBio sequencing also allowed identifying for repeats elements in strain F3E8. An extra copy of the whole ribosomal RNA operon and one extra copy of the repressor of the arginine regulon were found in F3E8 compared to the parental strain.

Analyses of Recombination Mechanism Leading to Genomic Variations

ClonalFrame is a Bayesian phylogenetic method which performs inference under evolutionary models accounting for the effect of homologous recombination (X. Didelot and D. Falush, Genetics, 2007, 175, 1251-66). To determine regions in the genome of high probability of homologous recombination ClonalFrame was used. First, variable regions between the recombinants and the parents were removed from individual Mauve alignments using the stripSubsetLCBs. This script is distributed by Mauve as a minor program to complement the principal one (Mauve). The core regions were submitted to 10,000 ClonalFrame iterations in which the first half were discarded as a burn-in (data used at the beginning of probabilistic determinations to establish stationary iterations). We detected 305±42 recombination events across the recombinant genomes which corresponded to regions where variants were found. In addition, we observed that the variations in the recombinants are located in very well conserved genes between the parental strains suggesting that recombination events are responsible for the variants found in the new strains.

Discussion

To understand the relationship between genotype and phenotype of the new strains generated by genome shuffling, DNA sequencing was performed for the 10 strains with the largest improvements in growth rate and PA production.

A comparison between the two parental strains revealed the presence of 30 prophages as the most significant difference between the two strains. Other studies have previously reported that the presence of cryptic prophages in bacteria can provide, among other important phenotypes, an increase in growth rate. The GS strains had 29 genes associated to prophages with 47% of them shared with the parental strain *P. acidipropionici* ATCC 4875. To explain the increase in growth relative to the parents, variants and multi copy variation analyses were performed. Three mutations were shared in all strains.

The first mutation is in the large subunit ribosomal RNA. The mutated ribosomal RNA was aligned against all the strains used in this study. Similar mutations have been previously reported in other GS studies. Resistance to avilamycin in *Streptomyces viridochmogenes* was linked to a mutation in the ribosome protein S12. The second shared mutation was found in the long chain acyl-CoA synthetase. This enzyme is a member of the ligase family that activates the breakdown of complex fatty acids. This enzyme plays a role in the physiological regulation of various cellular functions via the production of long chain acyl-CoA esters, which affect protein transport, enzyme activation, protein acylation, cell signalling, and transcriptional regulation. We speculate that the enzyme has a role in the effective use of the CoA in the Wood-Werkman cycle. The third shared mutation was in the cation diffusion facilitator. This protein is considered to be the efflux pumps that remove ions from cells using a proton antiport to drive substrate translocation across the membrane. This enzyme is likely playing an importance role in cell homeostasis.

In addition to shared mutations, we found changes in genes associated with regulation, acid tolerance, and transport. For example, the histone H1-like protein HC2 has mutations in five locations in five recombinants. Similar results have been reported previously using GS in *S. fradiae*, where mutations in a regulatory gene were found in three mutants. During that investigation, authors also observed conservation of a mutation of a relevant gene to achieve the improved phenotype.

Pacbio sequencing allowed for closing the genome of the F3E8 strain, which in turn allowed for the detection of gene duplications which may be contributing to the improved phenotype. An extra copy of a ribosomal RNA operon was found. Changes in ribosomal RNA have been associated previously with carboxylic acids tolerance through a signal recognition particle modification. The presence of new ribosomal machinery in the improved cell would allow for a new translational program which could result in a new gene expression program. This would be analogous to strains obtained using global transcriptional machinery engineering or ribosome engineering where whole gene expression alteration results in improved phenotypes. Similarly, an extra copy of a gene encoding for a protein responsible for regulation of the arginine deiminase pathway was also found. This pathway has been linked to acid tolerance in *P. acidipropionici*. The arginine deiminase pathway transports arginine inside the cell, transforms arginine into citrulline and ammonia to yield ornithine and carbamyl phosphate. Finally, the carbamate kinase reversibly transforms the carbamyl phosphate and ADP into ATP, $CO_2$, and ammonia. This system is not only useful to produce energy but also produces ammonia to alkalinize the media. Using the assembled recombinant and parents genomes, we detected around 300 recombination events across the recombinant genomes which strongly correlate with the position of the variants identified in the new strains. Variations were found in well conserved genes between the two parental strains. No variants were found in unique genes of the parental strains providing further evidence of the mechanism of recombination in GS.

EXAMPLE 6

Use of Subsequent Rounds of Genome Shuffling to Further Improve *Propionibacterium acidipropionici* Strains In order to further enhance growth rate, pH tolerance, propionic acid productivity and yield, a further round of genome shuffling was conducted using the highest performing strain, F3E8, from the original round of genome shuffling. Four additional *Propionibacterium* strains were included in the genome shuffling to ensure genetic diversity: *P. acidipropionici* ATCC 4875, *P. acidipropionici* ATCC 4965, *P. intermedium* ATCC 14072, *P. jensenii* ATCC 9617.

Material and Methods

Bacteria. To access genomic diversity, four propionibacteria wild type strains and one mutant were used for genome shuffling. From a collection of 17 wild type strains (Stowers et al., J. Ind. Microbiol. Biotechnol., 2014, 41, 837-852), the following four strains were selected: *P. acidipropionici* ATCC 4875, *P. acidipropionici* ATCC 4965, *P. intermedium* ATCC 14072, *P. jensenii* ATCC 9617. We also used the derivative strain, *P. acidipropionici* F3E8, described in the present disclosure. The strains were kept at −80° C. using glycerol (20%) as cryoprotector.

Media. The culture media for pre-inoculum preparation was PAM as described in Example 2. Agar (15 g/L) was added to prepare PAM plates. Sucrose (80 g/L) was added to perform fermentations in instrumented fermenters. Media components and the carbon source (i.e. sucrose) were sterilized separately for 20 min at 121° C. Chemical defined medium (CDM) was used to test effects of exogenous metabolite additions. The base CDM media consisted in (mg/L): sucrose (20000), $FeSO_4.7H_2O$ (10), Fe$(NO_3)_2.9H_2O$ (1), $K_2HPO_4$ (100), $KH_2PO_4$ (500), $MgSO_4.7H_2O$ (500), $MnSO_4$ (10), $CaCl_2.6H_2O$ (10), $NaH_2PO_4.H_2O$ (1597.5), $CoCl_2.6H_2O$ (10), $Na_2HPO_4$ (3675), arginine (2000), asparagine (2000), cysteine (200), glutamine (200), histidine (200), leucine (200), methionine (200), phenylalanine (200), proline (200), serine (200), tryptophan (200), tyrosine (200), biotin (0.2), riboflavin (2), thiamine hydrochloride (1), vitamin B12 (0.2), and pantothenic acid (2).

pH gradient plate. The PA/pH gradient plate was prepared using PAM agar supplemented with 5 g/L of PA salt at either low pH (3) or near to neutral pH (6.5). To create the gradient, a square plate (100×100 mm) was raised 0.5 cm on the side and the agar enriched with PA at pH 6.5 was poured into the plate. Once this layer was solidified, the plate was placed horizontally and the second layer of agar supplemented with PA at pH 3 was poured. Finally, the plate was left overnight at room temperature to allow the formation of the PA/pH gradient. The pH gradient was confirmed using pH indicator strips.

Measurement of internal pH (pHi). The protocol to measure the internal pH was adapted from (Guan et al., J. Biotechnol., 2013, 167, 56-63). The fluorescence method with 2', 7'-bis-(2-carboxyethyl)-5(and 6)-carboxyfluorescein acetoxymethyl ester (BCECF AM) was used to determine the pHi. Cells (OD600=2 for a working volume of 2 mL) were centrifuged (12,000 rpm, 1 min) and washed with 50 mM HEPES-K buffer (pH 8). The pellet was re-suspended in 2 mL of the same HEPES-K buffer and incubated with 1 uL of 1 uM BCECF AM for 20 min at 32° C. After, the cells were washed with 50 mM potassium phosphate buffer (pH 7). The pellet was re-suspended in the HEPES-K buffer, and half of the suspension was filtered. Fluorescence intensities were measured with a fluorescence spectrophotometer with an excitation spectrum of both 490 nm (pH sensitive) and 440 nm (pH insensitive). The emission was at 535 nm. The ratio of the emission intensity of both the suspension (S) and filtrate (F) at 490 and 440 was determined: $R=(S_{490}-S_{440})/(F_{490}-F_{440})$. This ratio and a calibration curve were used to calculate the pHi of all subsequent samples.

The calibration curve was determined for each strain as follows. Valinomycin and nigericin (Sigma) were added to each strain to a final concentration of 50 uM to maintain equilibration of pHi with extracellular pH (pHex). The cultures were then incubated at 32° C. for 20 min. Cells (A600 for a working volume of 2 mL) were centrifuged, washed and re-suspended in 2 mL of a buffer at pH 4, 5, 6, 7, or 8 (50 mM citrate buffer, pH 4 and 5; 50 mM phosphate buffer, pH 6, 7 and 8). After, 1 uL of 1 uM BCECF AM was added and incubated for 20 min at 32° C. Once incubated, the cells were washed and re-suspended using the respective buffer. Finally, half of the suspension was filtered and both the fluorescence determination and ratio calculation were performed as described above.

Analytical methods. Optical density of the culture was measured at 600 nm using a Biochrom Libra S12 UV/Vis Spectrophotometer. Organic acids, carbohydrates, and alcohols were quantified by ion-exclusion chromatography using an Agilent 1200 HPLC system and an Agilent Hiplex H column (300×7.7 mm, PL1170-6830) with a guard column (SecurityGuard Carbo-H, Phenomenex PN: AJO-4490). Sugars and alcohols were monitored using a refractive index detector (Agilent RID, G1362A) set on positive polarity and optical unit temperature of 40° C., while organic acids were monitored at 210 nm (Agilent MWD, G1365B). 30 uL of sample was injected into the column using an auto-sampler (Agilent HiP-ALS, G1367B) while the column temperature kept at 65° C. using a thermostatted column compartment (Agilent TCC, G1316A). Analytes were eluted isocratically with 4 mM $H_2SO_4$ at 0.6 mL/min for 26 min. Chromatograms were integrated using ChemStation (Rev B.03.02 [341]).

Amino acids were quantified as described by (Chacko et al., Mol. Microbiol., 2014, 93(4), 797-813). In brief, samples were diluted 1:1 with internal standards and derivatized amino acids were analysed by RP-HPLC. Derivatization was performed in a high-performance autosampler (Agilent HiP-ALS SL, G1367C). 0.5 uL of sample containing 250 uM of internal standards, sarcosine and 2-aminobutanoic acid, was added into 2.5 uL of borate buffer (0.4 N, pH 10.2, Agilent PN: 5061-3339), mixed and incubated for 20 s at 4° C. 1 uL of OPA reagent (10 mg o-pthalaldehyde/mL in 3-mercaptopropionic acid, Agilent PN: 5061-3335) was then added to initially derivatize primary amino acids. The reaction was mixed and incubated for 20 s at 4° C. Then 0.4 uL of FMOC reagent (2.5 mg 9-fluorenylmethyl chloroformate/mL in acetonitrile, Agilent PN:5061-3337) was added, mixed and incubated for 20 s at 4° C. to derivatize other amino acids. 45.6 uL of buffer A (40 mM $Na_2HPO_4$, 0.02% $NaN_3$, pH 7.8) was added to lower the pH of the reaction prior to injecting the 50 uL reaction mixture onto an Agilent Zorbax Extend C-18 column (3.5 urn, 4.6×150 mm, Agilent PN: 763953-902) with a guard column (SecurityGuard Gemini C18, Phenomenex PN: AJO-7597). The column temperature was kept at 37° C. in a thermostatted column compartment (Agilent TCC, G1316B). Chromatography was performed using an Agilent 1200-SL HPLC system, equipped with an active seal wash and a degasser (Agilent Degasser, G1379B). The HPLC gradient was 2-45% B from 0-18 min, 50-60% B from 18.1-20 min, 100% B from 20.1-24 min, and 2% B from 24.1-27 min—using a binary pump (Agilent Bin Pump SL, G1312B). Buffer B was 45% acetonitrile, 45% methanol, and 10% water. Flow rate was 2 mL/min. Derivatised amino acids were monitored using a fluorescence detector (Agilent FLD, G1321A). OPA-derivatised amino acids were detected at 340, and $450_{em}$ nm from 1-18 min, and FMOC-derivatised amino acids at $266_{ex}$ and $305_{em}$ nm from 18-27 min. Quantifications were based on standard curves derived from serial dilutions of amino acid standard (Sigma, AAS18-10ML) and amino acid supplement (Agilent, 5062-2478) kits. Chromatograms were integrated using ChemStation (Rev B.03.02[341]).

Intracellular metabolites extraction. Cells sampled at mid-exponential phase of instrumented fermenters were used for intracellular metabolomics analyses. Metabolite extraction was performed with 50% acetonitrile (ACN). Briefly, a cell volume corresponding to 1-20 optical density units (ODs) were harvested and centrifuged at 20,172 G for 2 min at room temperature. The supernatant was then discarded, and the pellet resuspended in 50% ACN. This solution was vortexed for 10 seconds every 2 min for three times and centrifuged for 3 min at 4° C. at 20,172 G. After, the supernatant was placed into a tube and frozen at −80° C. before being freeze-dried. Finally, the powder was resuspended in 0.5 mL of MilliQ water. Intracellular metabolites of the central carbon metabolism were analyzed by LC-MS and intracellular amino acids by HPLC (method described above). Metabolite concentrations were standardized using dry cell weight values. The factor to convert OD600 to dry cell weight (g/L) was 0.25 for *P. acidipropionici* ATCC 55737 and 0.29 for *P. acidipropionici* WGS 7.

Inoculum preparation. Under sterile conditions, the bacteria activation was carried out in a 1.5 mL Eppendorf tube with 1 mL of PAM media inoculated with 0.8% (v/v) of a glycerol stock. This culture was allowed to grow for 24 hours at 32° C. The cultures were transferred into a 15 mL Falcon tube containing 14 mL of PAM media and allowed to grow for an additional 24 hours at 32° C. 5% (vol/vol) of this culture was used to inoculate 250 mL serum bottles containing 100 mL of PAM media and allowed to grow for an additional 24 hours. Cells from the serum bottles in mid-exponential phase were used to inoculate the fermenters at an initial optical density of 0.3 measured at 600 nm.

Protoplast formation, fusion, and regeneration. Protoplast formation buffer (PFB) was made from (g/L): sodium succinate (40.5), sucrose (42.75), and $MgCl_2$, (1.9). PFB was dissolved in one litre of Tris-HCl 0.05 mol/L at pH 7.1 (Guan et al., "Genome-Shuffling Improves Acid Tolerance . . . " in Advances in Chemistry Research, Vol 15, Chapter 8 (2012) Nova Science Publishers, Inc., pp 143-152). Regeneration buffer (RB) was made from (g/L): yeast extract (10), trypticase soy (5), $KH_2PO_4$ (1.5), $K_2HPO_4$ (2.5), and BSA (5). pH was adjusted to 7 (Guan et al., "Genome-Shuffling Improves Acid Tolerance . . . " in Advances in Chemistry Research, Vol 15, Chapter 8 (2012) Nova Science Publishers, Inc., pp 143-152). Protoplasts were prepared as described in (Guan et al., "Genome-Shuffling Improves Acid Tolerance . . . " in Advances in Chemistry Research, Vol 15, Chapter 8 (2012) Nova Science Publishers, Inc., pp 143-152) with some modifications as subsequently described. Cells were grown for 24 hours in PAM media supplemented with 40 g/L of sucrose and 1% of glycine. Cells were then conditioned in PAM media containing 1% of glycine and 120 g/L of sucrose for an extra 24 hours. After at least ten generations, cells were washed twice using PBS and fixed to an OD600 nm=0.2 in a lysozyme solution containing 15 mg/mL (600,000 U/mL) in PFB. Cell walls were digested in a 125 mL flask for two hours in a shaker incubator at 120 rpm and 40° C. Protoplasts were detected in a light microscope using the 100× oil immersion objective and counted using a haemocytometer. When appropriate, protoplasts were regenerated in RB (pH=7 for 48 h at 32° C.). For the protoplast fusion, the protocol from Guan et al., "Genome-Shuffling Improves Acid Tolerance . . . " in Advances in Chemistry Research, Vol 15, Chapter 8 (2012) Nova Science Publishers, Inc., pp 143-152) was used with minor modifications. Protoplasts were treated with UV light for 1 min or heated at 60° C. for 2 h. Cells were mixed, centrifuged and re-suspended in 500 μL of PFB. Then 500 μL of PEG 6000 (80%) with 20 mmol/L $CaCl_2$ was added. Fusion conditions were pH 7.1, time 30 min, and temperature 32° C. After fusion, 5 mL of PFB was added, and the sample was centrifuged at 3500 rpm for 5 min. Protoplasts were washed two times with 5 mL of PFB and re-suspended in 1 mL of RB.

Obtaining recombinants with high PA yields. Strain diversity was created using the wild type strains: *P. acidipropionici* ATCC 4875, *P. acidipropionici* ATCC 4965, *P. intermedium* ATCC 14072, and *P. jensenii* ATCC 9617. To obtain this library, *P. acidipropionici* ATCC 4875 was used to perform GS with the other three wild type *Propionibacterium* strains separately. In total, three rounds of genome shuffling were performed with each set of strains. Cells for subsequent GS rounds were selected from the acidic side of pH/PA gradient plates. Next, another three rounds of GS were performed with the obtained library of *Propionibacterium* strains, the parental strains (*P. acidipropionici* ATCC 4875, *P. acidipropionici* ATCC 4965, *P. intermedium* ATCC 14072, *P. jensenii* ATCC 9617) and the previously created mutant *P. acidipropionici* F3E8. Finally, the new recombinants were isolated by serial dilutions in PAM media agar plates. Individual recombinants were randomly selected and screened in a 96 well plate containing 100 µL of PAM media at pH 5 and 25 g/L of PA. Growth was monitored using a micro-plate reader (FLUOStar Omega, BMG Labtech, Mornington, Victoria, Australia) adapted to maintain anaerobic conditions through a constant injection of nitrogen.

The selection strategy was based on an acid tolerance improvement which was determined by an acidic ratio comparison between the new strains and the wild type—the individual ratios were calculated dividing the specific growth rate under acidic conditions over specific growth rate under non-acidic conditions. The best performing strains were scaled up to 250 mL serum bottles with a working volume of 100 mL.

Serum bottles were incubated using an orbital shaker incubator (Multitron, Infors-HT, Bottmingen, Switzerland) at an agitation rate of 100 rpm (2.5 cm orbit) and a working temperature at 32° C. for 96 hours.

Instrumented fermenters. Fermentations were performed using 2 L Applikon fermenters with a working volume of 1 L. Fermenters were equipped with probes and controllers for pH, dissolved oxygen, temperature, and agitation. The agitation rate was controlled with two Rushton impellers at 300 rpm. The pH was controlled at 6.5 using 10 M NaOH. The temperature of the culture was maintained at 32° C. using an electric jacket. Prior to inoculation, the fermenters were sparged with $N_2$ for at least 15 minutes. A constant $N_2$ flow was kept for the duration of the fermentation at a flow rate of 0.3 L/min. Samples for metabolomics analyses were taken in the middle exponential phase.

Growth characterization. Specific growth rate (µ) was calculated at the middle exponential phase using the logarithm method. Specific growth rate calculations of kinetics in 96 well plates were performed using the program GrowthRates (Hall et al., Mol. Biol. Evol., 2014, 31, 232-238. For consistency, volumetric productivity (Pv) was calculated for the same time interval (ranging from 15 to 30 hours). Yield (Yps) was calculated using the total PA produced over the total substrate consumed. PA: Acetic Acid and PA: Succinic Acid ratios were calculated using total organic acid production. The specific consumption rate of sucrose (qs) and the specific production rate of PA (qp) were calculated at the middle exponential phase multiplying specific growth rate by the linear correlations of sugar or PA with biomass.

Results

Obtaining Strains with High PA Yields

Propionibacterium strains were generated and screened using the Genome Shuffling methodology described in the Materials and Methods. After the screening, 13 strains with an apparent improvement in the acid tolerance were obtained. To confirm the results, select strains were screened in serum bottle fermentations. As can be seen in Table 5, the new strains showed diversity in growth rate and PA yield. The recombinants presented an increase in the average final PA titer of 38%, an average improvement in the PA yield of 41% and a higher average growth density of 27%. Also, the average final pH was 0.05-0.15 pH units lower than what was observed during studies with the wild type strain. One of the strains, WGS 7, achieved a propionic acid yield of 0.75+/−0.05 g/g, the highest reported to date. To validate the results of serum bottles fermentations, we selected the recombinant with the highest yield (*P. acidipropionici* WGS 7) for further study in 2 L fermenters.

TABLE 5

Parameters of the fermentations in serum bottles for strains generated using Genome Shuffling.

| Strain | Final OD600nm | Final pH | PA (g/L) | PA:AA (g/g) | Yps (g/g) |
| --- | --- | --- | --- | --- | --- |
| *P. acidipropionici* WGS.1[1] | 19.13 ± 0.44 | 3.82 ± 0.01 | 8.39 ± 0.26 | 5.58 ± 0.25 | 0.59 ± 0.01 |
| *P. acidipropionici* WGS.2[1] | 18.07 ± 0.92 | 3.77 ± 0.01 | 9.64 ± 0.12 | 6.85 ± 0.02 | 0.63 ± 0.02 |
| *P. acidipropionici* WGS.3[1] | 19.65 ± 0.21 | 3.81 ± 0.01 | 8.67 ± 0.05 | 6.25 ± 0.21 | 0.58 ± 0.02 |
| *P. acidipropionici* WGS.4[1] | 19.78 ± 0.99 | 3.82 ± 0.00 | 8.29 ± 0.17 | 4.88 ± 0.14 | 0.64 ± 0.02 |
| *P. acidipropionici* WGS.5[1] | 19.67 ± 0.18 | 3.82 ± 0.02 | 9.37 ± 0.88 | 6.30 ± 0.91 | 0.70 ± 0.10 |
| *P. acidipropionici* WGS.6[1] | 19.03 ± 0.52 | 3.82 ± 0.01 | 8.80 ± 1.08 | 5.35 ± 1.04 | 0.65 ± 0.03 |
| *P. acidipropionici* WGS 7[1] | 19.06 ± 0.20 | 3.81 ± 0.00 | 8.67 ± 0.27 | 5.66 ± 0.56 | 0.75 ± 0.05 |
| *P. acidipropionici* WGS.8[1] | 20.27 ± 0.78 | 3.83 ± 0.01 | 8.82 ± 0.02 | 5.96 ± 0.56 | 0.60 ± 0.09 |
| *P. acidipropionici* WGS.9[1] | 19.47 ± 0.27 | 3.83 ± 0.01 | 8.57 ± 0.11 | 6.01 ± 0.06 | 0.55 ± 0.00 |
| *P. acidipropionici* WGS.10[1] | 20.46 ± 0.37 | 3.85 ± 0.01 | 8.20 ± 0.05 | 5.27 ± 0.07 | 0.53 ± 0.02 |
| *P. acidipropionici* WGS.11[1] | 19.69 ± 0.58 | 3.83 ± 0.01 | 8.81 ± 0.98 | 5.89 ± 0.46 | 0.57 ± 0.08 |
| *P. acidipropionici* WGS.12[1] | 19.29 ± 1.23 | 3.83 ± 0.00 | 8.64 ± 0.49 | 6.30 ± 1.21 | 0.57 ± 0.05 |
| *P. acidipropionici* WGS.13[1] | 18.14 ± 0.40 | 3.87 ± 0.01 | 8.13 ± 0.26 | 6.43 ± 0.96 | 0.53 ± 0.02 |
| *P. acidipropionici* F3E8[2] | 16.04 ± 0.20 | 3.92 ± 0.01 | 6.95 ± 0.18 | 5.26 ± 0.29 | 0.53 ± 0.02 |

[1] New strains from Genome Shuffling.
[2] Reference strain.
PA: Propionic acid.
PA:AA: Propionic acid/Acetic acid ratio.
Yps: propionic acid conversion per sugar consumed on a gram basis.
The data represent the average of two biological replicates.
The fermentation time was 96 h.

TABLE 6

Kinetic parameters of 2 L fermentations of the parental strains P. acidipropionici ATCC 55737,
P. acidipropionici F3E8, and the new strain from GS P. acidipropionici WGS 7.

| Strain | Yps (g/g) | PA:SA (g/g) | PA:AA (g/g) | *$P_v$ (g/L · h) | ΔpH | Final PA (g/L) |
|---|---|---|---|---|---|---|
| P. acidipropionici ATCC 55737 | 0.45 ± 0.028 | 6.28 ± 0.940 | 2.95 ± 0.35 | 0.530 ± 0.212 | 0.43 ± 0.035 | 26.28 ± 1.880 |
| P. acidipropionici WGS 7 | 0.62 ± 0.014 | 6.19 ± 0.233 | 5.45 ± 0.410 | 0.955 ± 0.148 | 1.27 ± 0.099 | 44.21 ± 0.933 |

*Range of time: 15-30 h
ΔpH: pHi − pHext (pHi: internal pH; pHext: external pH)

As can be seen in Table 6 and FIG. 4A-4D, the new strain (P. acidipropionici WGS 7) presented a remarkable improvement in its ability to produce PA. The yield was increased by 37%, the PA:AA ratio around 85%, and the volumetric productivity around 80%. In addition, the internal ΔpH (pHi-pHext) in the middle exponential phase of the fermentations; as can be seen in Table 6, was found to be ΔpH (pHi-pHext) 1.27 in WGS 7 and 0.43 in the wild type (ATCC 55737). It can also be seen from FIG. 4D that the amino acid consumption rates were notably different between WGS 7 and ATCC 55737.

EXAMPLE 7

Genomic and Metabolomic Characterization of the WGS 7 Mutant Obtained from Genome Shuffling In order to better understand the causes for improved performance of the WGS 7 strain, a series of genomic, metabolomics and transcriptiomic analysis were performed to characterize the strain relative to parental strains.

Material and Methods

RNA Extraction, Sequencing, and Analyses

Cells sampled at mid-exponential phase from instrumented fermenters were used for RNA extraction. 50 ODs were harvested and centrifuged at 4000 g for 10 min at room temperature. The supernatant was removed, and 5 mL of RNAlater® reagent was added to the pellet. After 8-24 h of incubation at 4° C., the RNAlater® was removed by centrifugation and the pellet stored at −80° C. for further use. RNeasy® Mini Kit (Qiagen) was used to extract the RNA and the RNA Clean and Concentrator-25 Kit (Zymo) to clean it. Next, the RNA was enriched depleting the ribosomal RNA with the Ribbo-Zero Magnetic Kit (illumina). The samples were cleaned and concentrated with the RNA Clean and Concentrator-5 Kit (Zymo). The quality of the RNA was evaluated by a Bioanalyzer (Agilent 2100). Finally, the samples were sequenced using the illumina platform 100 bp PE. Tophat, Cufflinks, and CuffDiff were used to align the RNAseq reads against the reference genome P. acidipropionici ATCC 55737 (Flores et al., Genome Announc, 2016, 4 (3), 00248-16), normalize and annotate the transcripts, and evaluate differential expression, respectively (Trapnell et al., Nat. Protoc., 2012, 7(3), 562-78).

DNA-Sequencing, De Novo Assembly and Annotation.

Genomic DNA of the different Propionibacterium strains were extracted using PureLink genomic DNA mini kit (Invitrogen Cat. No. K1820-01) and quantified using Nanodrop 1000 (Thermo Scientific) and Qubit dsDNA BR assay kit (Life Technologies Cat. No. Q32850). The quality of the DNA was determined by running a 1% agarose gel with DNA gel stain SYBR™ safe (Life Technologies Cat. No. S33102). The gel was visualized in a ChemiDoc MP system (Bio-Rad). PacBio was used to obtain the complete genome of new recombinant strain. The PacBio library preparation was performed using the protocol for 20 Kb selected with the BluePippin system. The library was prepared using the P6-C4 chemistry from Pacbio and was loaded using magnetic beads. The genome assembly was performed with the SMRT portal. This portal was also used to align the reads and call the variants of the sequenced genomes. Finally, the RAST and SEED viewer servers were used to respectively annotate and visualize the assembled genome (Aziz et al., BMC Genomics, 2008, 9, 75; et al., Methods Mol. Biol., 2013, 985, 17-45).

Results

P. acidipropionici WGS 7 Sequencing, De-Novo Assembly, Annotation, and Variant Detection The WGS 7 genome was annotated using the RAST server (Aziz et al., BMC Genomics, 2008, 9, 75). The genome was found to have a size of 3.61 Mb with 3333 CDS and 65 RNAs. After mapping the WGS 7 genome against the wild type strain P. acidipropionici ATCC 55737, 17 SNPs and 7 indels were identified as shown in Table 7. The annotation of these variants rendered 10 hypothetical proteins and 14 proteins inside of a subsystem (Table 7). Three mutations that seem likely to impact propionic acid production are SNP C2293187T in the ABC polar amino acid transporter gene, SNP C1487806T in the Cytochrome C biogenesis gene and SNP G1917729A in the promoter of the ABC multiple sugar transporter gene.

TABLE 7

Variants and copy number variation found in strain P. acidipropionici
WGS 7 relative to P. acidipropionici ATCC 55737.

| Genome coordinate* | Type | Reference | Alternate | Gene function | Remark |
|---|---|---|---|---|---|
| 294317 | SNP | CC | TT | ATP-dependent DNA helicase SCO5184 | — |
| 371247 | INDEL | A | delA | Hypothetical protein | — |
| 567004 | INDEL | G | delG | 2-dehydropantoate 2-reductase | — |
| 1105158 | INDEL | C | delC | Hypothetical protein | — |
| 1344547 | SNP | G | A | Cobalt-zinc-cadmium resistance protein | — |
| 1487806 | SNP | C | T | Cytochrome c-type biogenesis protein CcdA (DsbD analog) | — |

TABLE 7-continued

Variants and copy number variation found in strain *P. acidipropionici* WGS 7 relative to *P. acidipropionici* ATCC 55737.

| Genome coordinate* | Type | Reference | Alternate | Gene function | Remark |
|---|---|---|---|---|---|
| 1605833 | INDEL | G | delG | Putative integral membrane protein | Intergenic |
| 1685121 | SNP | C | T | Hypothetical protein | — |
| 1799226 | INDEL | — | insG | Conserved membrane protein, putative permease | — |
| 1913841 | SNP | G | T | Hypothetical protein | — |
| 1917729 | SNP | G | A | Multiple sugar ABC transporter, substrate-binding protein | Promoter |
| 2190342 | SNP | C | T | Myo-inositol 2-dehydrogenase | — |
| 2293187 | SNP | C | T | Amino acid ABC transporter, ATP-binding protein | — |
| 2312506 | INDEL | — | insCCAC | Hypothetical protein | Intergenic |
| 2360492 | SNP | C | T | UDP-glucose 4-epimerase | — |
| 2440725 | SNP | G | C | Hypothetical protein | — |
| 2440740 | SNP | G | A | Hypothetical protein | — |
| 2440971 | SNP | A | C | Hypothetical protein | — |
| 2505914 | INDEL | G | delG | Ribose ABC transport system, ATP-binding protein RbsA | — |
| 3092919 | SNP | C | G | Chromosome segregation ATPases | — |
| 3167868 | SNP | C | G | Hypothetical protein | — |
| 3184231 | SNP | T | G | Hypothetical protein | Intergenic |
| 3279129 | SNP | G | A | Hypothetical protein | — |
| 3335969 | SNP | A | G | LSU rRNA | — |

SNP: single nucleotide polymorphism;
INDEL: insertion or deletion;
del: deletion;
ins: insertion;
*Genome coordinate in *P. acidipropionici* ATCC 55737.

Extracellular Metabolites

Figure 4A:
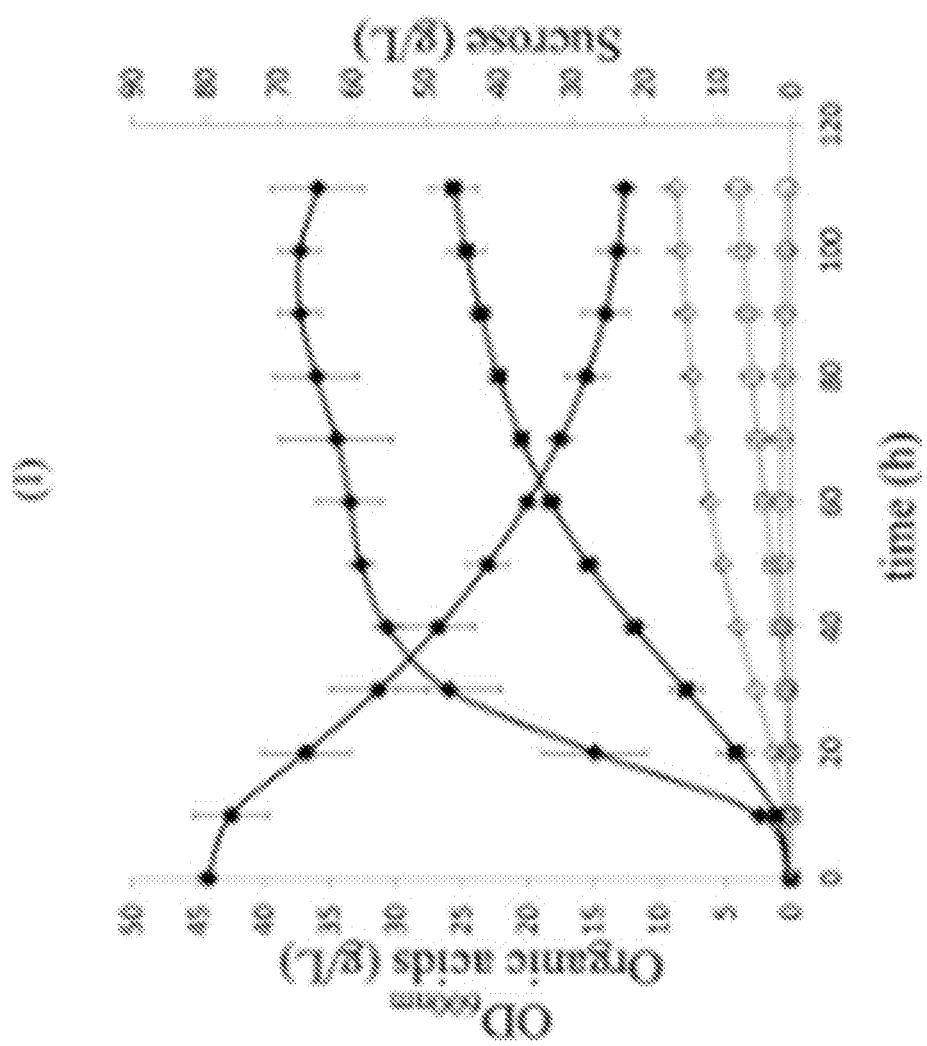
FIGS. 4A-4D show fermentation profiles in 2 L bioreactors and their external metabolite specific rates.
Figure 4B:
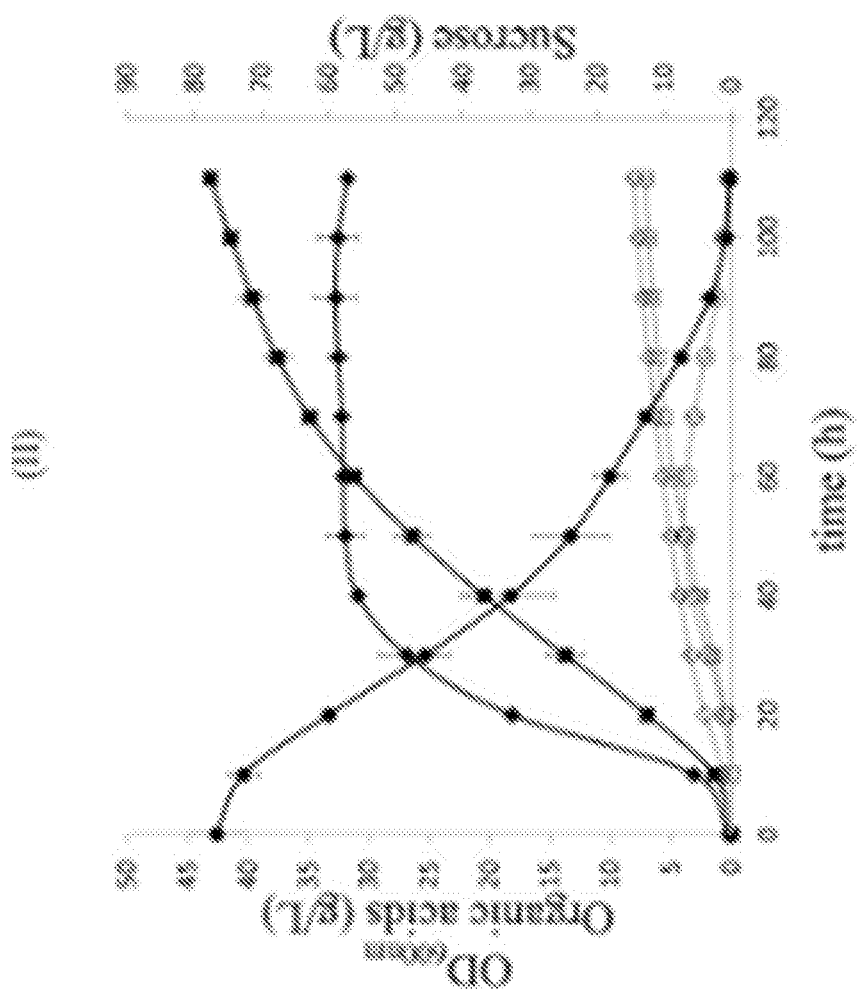
Figure 4C:
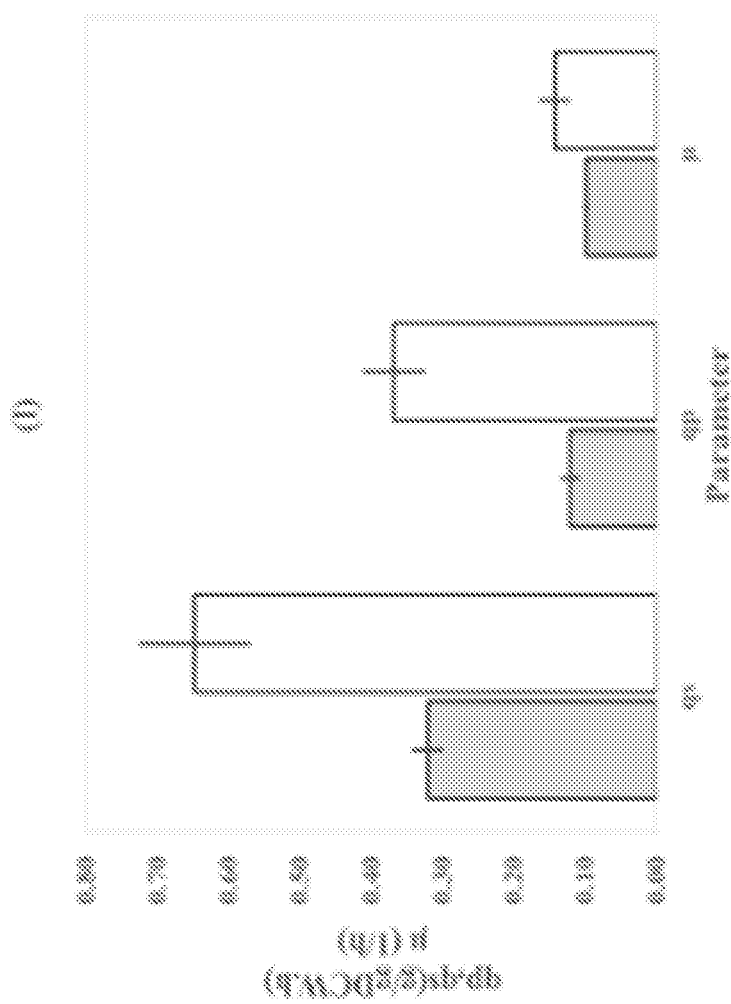
Figure 4D:
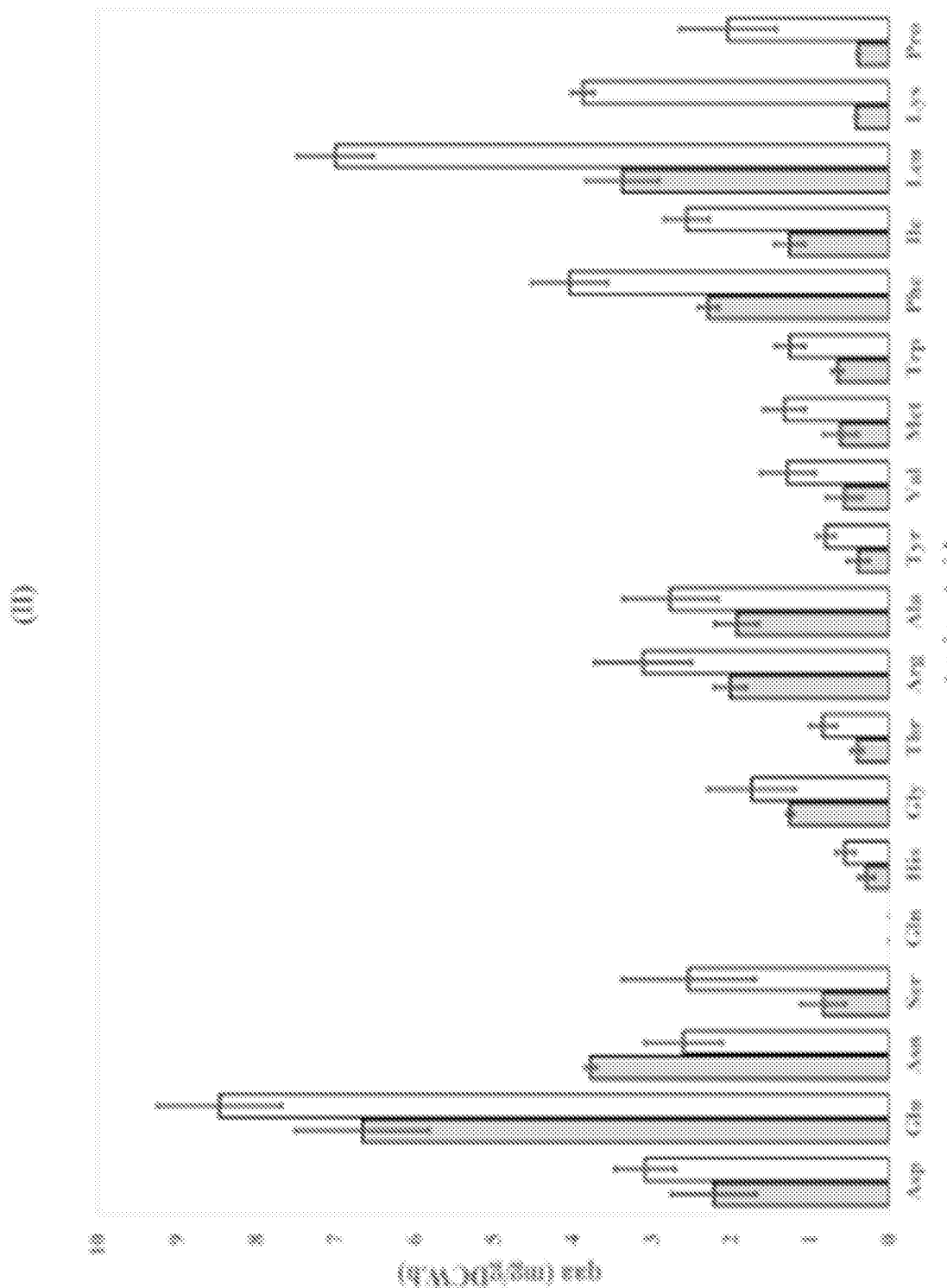

Extracellular metabolites were measured across 2 L fermentations with the WGS 7 and ATCC 55737 (FIGS. 4A & 4B). Specific growth rate, the specific consumption rate of sucrose, the specific consumption rate of free amino acids, and specific production rate of PA were calculated at the mid-exponential phase. As can be seen in FIG. 4C, WGS 7 demonstrated a 96% increase in the specific consumption rate of sucrose and a 216% increase in the specific production rate of PA relative to ATCC 55737. Interestingly, the WGS 7 depleted the sucrose in the culture media, whereas ATCC 55737 consumed only 69% of the total sugar. This observation supports the hypothesis that the SNP G1917729A, which was identified in the promoter of the putative ABC multiple sugar transporter gene, upregulated its expression and improved sucrose consumption. Changes in the specific consumption rates of the free amino acids were also detected. As can be seen in FIG. 4D, WGS 7 had an increase in the specific consumption rate of the following amino acids: serine, arginine, tyrosine, valine, methionine, tryptophan, proline, phenylalanine, isoleucine, leucine, and lysine.

Differential RNAseq Analyses

Differential expression between wild type strain *P. acidipropionici* ATCC 55737 and shuffled strain *P. acidipropionici* WGS 7 was evaluated. The analysis identified 2406 transcribed genes, of which 76 were expressed significantly (q<0.05) different—13 downregulated and 63 upregulated.

Of the genes that were significantly differentially expressed, the new strain presented upregulation of eight ABC sugar transporters. Among these transporters, the ABC sugar transporter XLOC_000592 had the G1917729A mutation, which is located in the promoter of the gene. The shuffled strain also presented significant upregulation of three ABC amino acid transporters and three ABC oligopeptides transporters. Inside these category of genes, the ABC amino acid transporter XLOC_000834 presented the mutation C2293187T (see Table 7). Regarding electron transport genes, upregulation of the nitric oxide reductase XLOC_002350 (cytochrome c) was identified, which is likely related to the SNP C1487806T in the cytochrome c biogenesis gene. Interestingly, the methylglyoxal pathway was also found overexpressed in the new strain. This pathway aids to degrade the methylglyoxal compound through the formation of L-lactate and D-lactate, which are finally converted to pyruvate (Weber et al., Microbiology+, 2005, 151(3), 707-716). In addition, significant upregulation of three genes involved in the pentose and glucoronate interconversions were identified: altronate dehydratase (uxaA), altronate oxidoreductase (uxaB), and unronate isomerase (uxaC). The oxidative reactions of the pentose phosphate pathway were found to be overexpressed. The reactions associated with acetate interconversion were also more highly expressed in WGS 7 than in ATCC 5573. The intermediary compound of acetate dissimilation or assimilation, namely acetyl-CoA, is used to enter the TCA cycle through the citrate synthase (gltA) reaction. The transcription of this gene was also found overexpressed in WGS 7. This suggests that TCA cycle was more active in the shuffled strain than in WGS 7.

Experiments on CDM to Test Individual Effects of Metabolites

Figure 5:
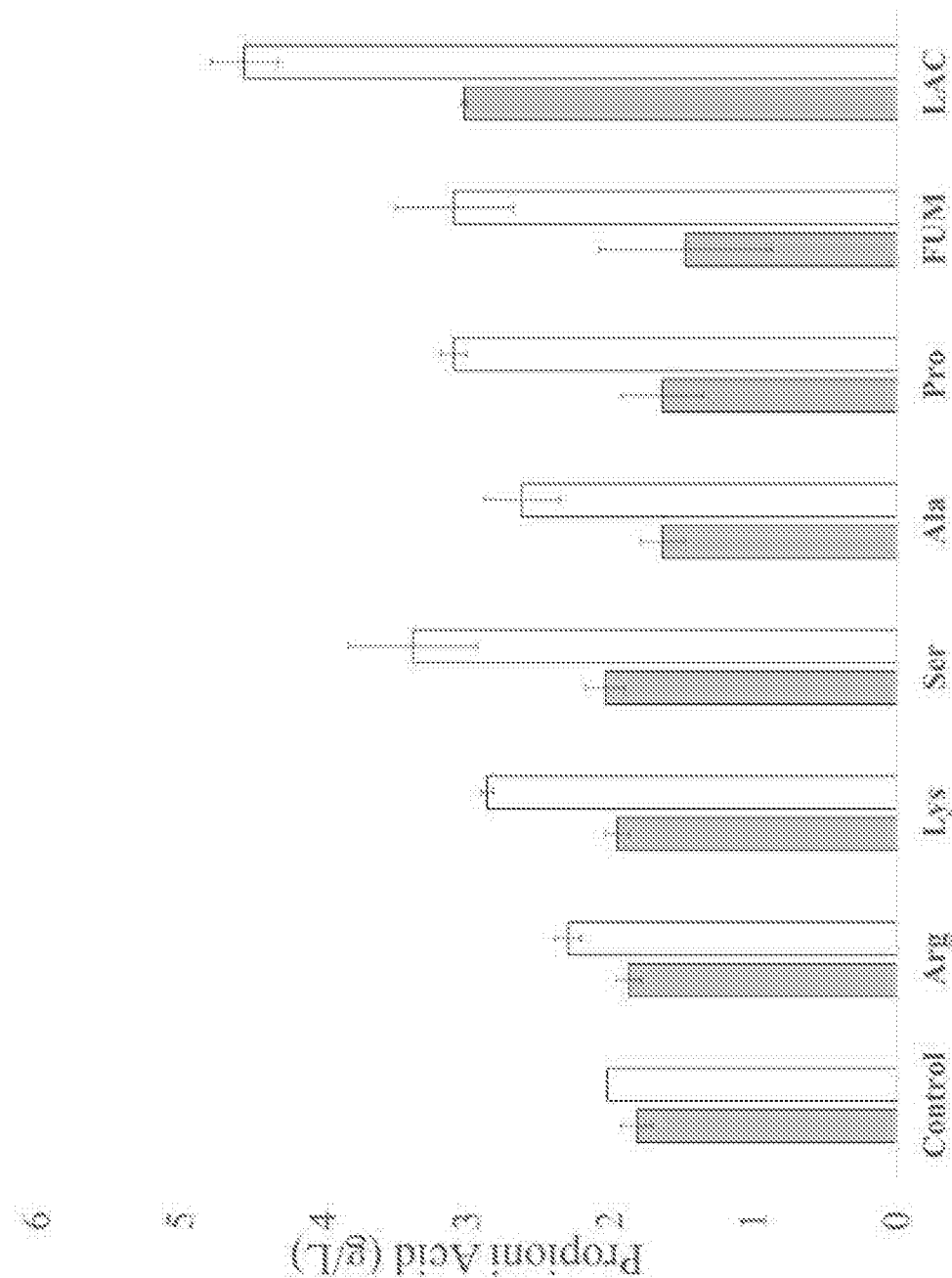
FIG. 5 shows the effects of exogenous addition of 50 mM of lactate (LAC), 10 mM of fumarate (FUM), 10 mM of arginine (Arg), 10 mM of lysine (Lys) or 10 mM of proline (Pro) in *P. acidipropionici* ATCC 55737 (shaded bars) and *P. acidipropionici* WGS 7 (open bars). Fermentations were performed by duplicate serum bottle fermentations containing CDM media.

Based on the genomic variant and metabolomic profiles analyses, experiments were conducted to test the effect of individual metabolites in the production of PA. The experiments were performed in serum bottles using CDM. As can be seen in FIG. 5, *P. acidipropionici* WGS 7 increased PA production by approximately 112%, 50%, 38%, 38%, and 25% when lactate, fumarate, proline, lysine, or arginine were supplemented to the CDM, respectively. On the contrary, the wild type strain *P. acidipropionici* ATCC 55737 increased the PA production by 66% only when lactate was added to the CDM media. This data is consistent with the genome sequencing data, which revealed a SNP (C2293187T) in a gene (XLOC_000834) annotated as a putative ABC transporter of polar amino acids. This seems to have resulted in increased consumption of several polar amino acids. RNAseq data confirms this assertion, as indicated by the upregulation of XLOC_000834. Further, it can be seen in FIG. 5 that the feeding of certain amino acids can substantially improve the PA titer of strain WGS 7, far more than the improvement observed with ATCC 55737. Adding serine at 10 mM improved WGS 7 titer by 75% and adding alanine at 10 mM improved titer by 25%.

As mentioned previously, the genomics analysis of WGS 7 revealed SNP C1487806T located within the cytochrome c biogenesis gene. Correspondingly, the RNAseq analysis showed significant upregulation of the nitric oxide reductase—XLOC_000683—(cytochrome c) (q<0.05, log 2 1.30 fold), suggesting that the C1487806T mutation in the cytochrome c biogenesis is likely playing an important role in the generation of the c-type cytochromes. This mutation could also be indirectly aiding to neutralize acidic environments inside the cells, as the final nitrate degradation product is ammonia. In addition, it is reported that lactate requires an electron acceptor to be oxidized and produce pyruvate through the reaction lactate dehydrogenase. Some authors suggest that cytochrome c can act as natural electron transport in the lactate-pyruvate reaction (Ogata et al., J. Biochem., 1981, 89(5), 1423-1431; Yoshimura et al., Biochim Biophys Acta, 1977, 492, 331-339). Thus, the upregulated XLOC_000683 gene could be improving the electron transport in the lactate-pyruvate reaction. To test this hypothesis, CDM serum bottle fermentations enriched with 50 mM of exogenous lactate were conducted. Interestingly, as can be seen in FIG. 5, WGS 7 produced 63% more PA than ATCC 55737 by the addition of lactate. This suggests that the mutation C1487806T is having an important role in the electron transport chain in P. acidipropionici WGS 7. An electron transport system in P. acidipropionici is also responsible for the reduction of fumarate in the Wood Werkman Cycle (Parizzi et al., BMC Genomics, 2012, 13, 562). Flavin, in the form of flavin adenine dinucleotide (FAD), has been identified in the fumarate reductase enzyme (Ingledew et al., Microbiol. Rev., 1984, 48(3), 222-71). Regarding this system, we found significant upregulation of the flavin reductase gene (XLOC_001914) in our transcriptome data (q<0.05, log 2 1.31). This suggests that the step fumarate-succinate is contributing to the increase in PA production, as it has been associated with ATP generation (Ingledew et al., Microbiol. Rev., 1984, 48(3), 222-71). To evaluate our hypothesis, we added exogenous fumarate (10 mM) on CDM media and grew both strains in serum bottles. As can be seen in FIG. 5, the new strain had a PA titer that was two-fold higher than the wild type strain. The fact that the latter strain did not present any benefit for the exogenous addition of fumarate strengthens our hypothesis of a probable improvement in the electron transport chain in the fumarate-succinate reaction (FIG. 5). It seems likely that modifications in the electron transport chain are also affecting the metabolite pools in the TCA cycle. The new strain only presented an increase of 1.13 folds of citrate and 1.65 folds of succinate; intracellular malate did not present any change. Contrary to our results, Guan et al. (Guan et al., Metabolomics, 2015, 11(5), 1106-1116) found more than two levels of magnitude of intracellular citrate, succinate, fumarate, or malate in their mutant strain P. acidipropionici WSH1105 than in wild type P. acidipropionici CGMCC 1.2230. In that study, to test the individual effect of fumarate, 0-50 mM of this metabolite was added to buffered PAM media; the addition of 30 mM of fumarate increased PA production 10.52% (Guan et al., Metabolomics, 2015, 11(5), 1106-1116).

What is claimed is:

1. An isolated strain of *P. acidipropionici* (strain WGS 7), wherein said strain is deposited with the American Type Culture Collection (ATCC), on Sep. 2, 2016 under ATCC Accession No. PTA 123476.

2. A method for producing propionic acid, said method comprising the steps of culturing a *P. acidipropionici* strain of claim 1 under conditions suitable for growth of the strain;

recovering the propionic acid produced by said strain.

* * * * *

SEQUENCE LISTING

```
<160> NUMBER OF SEQ ID NOS: 22

<210> SEQ ID NO 1
<211> LENGTH: 978
<212> TYPE: DNA
<213> ORGANISM: Propionibacterium acidi-propionici

<400> SEQUENCE: 1
tcagacgtcc agatcctcat aggaccgggg gtcctcgatc ggttccaggt ggcccatcac    60
ccgcagatcg ggccacttgt cgaggagttc gtcgatgagg tcctccatga cgtcgtggcc   120
gtgctgaacg gtccactcac cggggaccag catgtggaac tccaggaacc gccgatagcc   180
ggcctcccgg gtgcggatgg cgtggaaggc aacccgctcg ctgctgtgct ggtccaggaa   240
ctcccggatg gcggcgttgt cggccttcgg cagggagacg tccatcagcc ctgcgcccga   300
ctggccgatg agtcgggccc cggtgacgag gatattcagg cccaccgcga aggccacgat   360
cgggtccagt cgctgccagc cggtgagcca caccaggccg actcccacga ccacgccgat   420
cgaggtgacg acgtcggtcc acaggtgccg accgtcggcc agcagggtca tcgagcgacg   480
acgccggccg ttgcgcatga ggaccgcggc caccgagccg ttgatgaccg aggcgaccgc   540
cgagaccacc aggcccagtc ccagattctc caggccctgg gggtgcagga agcggtcgac   600
ggccgagacc aggatgacgg ccgccgcgac gaagatcatg atgccctcga ccgccgcgga   660
gaagtactcg gccttcgagt gcccgaactg gtggttcttg tccggcggct tgatggacac   720
cttgagggcc accagggcga cgatcgcggc caccaggttc accaccgact cggcggcgtc   780
cgagagcagg cccaccgatc cggtgagaag ccacgctccg gtcttgagga ggatggtggc   840
```

```
gatcgccgcc gcgatcgaca gccaggcgaa acggctcagg tcctccggag gttcgtggcg    900
cggggccgag ttggctgtcg ggggatccg ggggctgctc accgcgccaa ttatgccagc    960
gtccgggcga tcggccac                                                  978
```

<210> SEQ ID NO 2
<211> LENGTH: 326
<212> TYPE: PRT
<213> ORGANISM: Propionibacterium acidi-propionici

<400> SEQUENCE: 2

```
Ser Asp Val Gln Ile Leu Ile Gly Pro Gly Val Leu Asp Arg Phe Gln
1               5                   10                  15

Val Ala His His Pro Gln Ile Gly Pro Leu Val Glu Glu Phe Val Asp
            20                  25                  30

Glu Val Leu His Asp Val Val Ala Val Leu Asn Gly Pro Leu Thr Gly
        35                  40                  45

Asp Gln His Val Glu Leu Gln Glu Pro Pro Ile Ala Gly Leu Pro Gly
    50                  55                  60

Ala Asp Gly Val Glu Gly Asn Pro Leu Ala Ala Val Leu Val Gln Glu
65                  70                  75                  80

Leu Pro Asp Gly Gly Val Val Gly Leu Arg Gln Gly Asp Val His Gln
                85                  90                  95

Pro Cys Ala Arg Leu Ala Asp Glu Ser Gly Pro Gly Asp Glu Asp Ile
            100                 105                 110

Gln Ala His Arg Glu Gly His Asp Arg Val Gln Ser Leu Pro Ala Gly
        115                 120                 125

Glu Pro His Gln Ala Asp Ser His Asp His Ala Asp Arg Gly Asp Asp
    130                 135                 140

Val Gly Pro Gln Val Pro Thr Val Gly Gln Gln Gly His Arg Ala Thr
145                 150                 155                 160

Thr Pro Ala Val Ala His Glu Asp Arg Gly His Arg Ala Val Asp Asp
                165                 170                 175

Arg Gly Asp Arg Arg Asp His Gln Ala Gln Ser Gln Ile Leu Gln Ala
            180                 185                 190

Leu Gly Val Gln Glu Ala Val Asp Gly Arg Asp Gln Asp Asp Gly Arg
        195                 200                 205

Arg Asp Glu Asp His Asp Ala Leu Asp Arg Arg Gly Glu Val Leu Gly
    210                 215                 220

Leu Arg Val Pro Glu Leu Val Val Leu Val Arg Arg Leu Asp Gly His
225                 230                 235                 240

Leu Glu Gly His Gln Gly Asp Asp Arg Gly His Gln Val His His Arg
                245                 250                 255

Leu Gly Gly Val Arg Glu Gln Ala His Arg Ser Gly Glu Lys Pro Arg
            260                 265                 270

Ser Gly Leu Glu Glu Asp Gly Gly Asp Arg Arg Asp Arg Gln Pro
        275                 280                 285

Gly Glu Thr Ala Gln Val Leu Arg Arg Phe Val Ala Arg Gly Arg Val
    290                 295                 300

Gly Cys Arg Gly Asp Pro Gly Ala Ala His Arg Ala Asn Tyr Ala Ser
305                 310                 315                 320

Val Arg Ala Ile Gly His
                325
```

<210> SEQ ID NO 3
<211> LENGTH: 3103
<212> TYPE: DNA
<213> ORGANISM: Propionibacterium acidi-propionici

<400> SEQUENCE: 3

```
gttgcaagct actaagtgcg gtcggtggat gccttggcac aagagccga tgaaggacgt      60
tgtaacctgc gataagcccc ggggagttgg ttcacgagct gtgatccggg ggtgtccgaa     120
tggggaaacc ttgaattgcc ggagtcatgt ccggtgaccc tgccctgaat gtataggggt    180
gtgggaggga acgtggggaa gtgaaacatc tcagtacccg caggaagaga aacaatatg     240
tgattccgtg agtagtggcg agcgaaagcg atgaggcca aaccgtgtgt gtgttcaaac     300
cggcaggtgt tgcacgtgcg gggttgtggg gtcttctggg atcgactgcc gtcggtccgt    360
ccagtgataa atggtgtgtt gaagtcgaag cgtctgggaa ggcgtaccgg agtgggtgag    420
agtcccgtag acgtggatgc accactggtg gaggataccc caagtagcgc gggactcgtg    480
gaatttcgcg tgaatctggc gggaccaccc gtcaagcctg aatactcctt ggtgaccgat    540
agtggatagt accgtgaggg aatggtgaaa agtaccccgg gaggggagtg aaagagtacc    600
tgaaaccggc cgcatacaat ccgtcggagc ctgcctgtac gggtgggtga cggcgtgcct    660
attgaagaat gagcctgcga gttagtggca tgtggcgagg ttaacccgtg tggggtagtc    720
gtagcgaaag cgagtccgat aagggcgcca gtcgcgtgtt ctagacccga agcggtgtga    780
tctatccatg gccaggatga agcgacggta agacgtcgtg gaggtccgca cccacttcag    840
ttgaaaatgg aggggatgag ctgtggatag gggtgaaagg ccaatcaaac actgtgatag    900
ctggttctcc ccgaaatgca tttaggtgca gcgtcgcgtg gttcttgctg gaggtagagc    960
actggatgat ctagggggcc tatcagctta ccgaaatcag ccaaactccg aatgccggca   1020
agtggagcgt ggcagtgaga cggcggggga taagcttcgt cgtcgagagg gaaacagccc   1080
agatcatcag ctaaggcccc taagcggtgg ctaagtggaa aaggatgtgg agttgcggtg   1140
acaaccagga ggttggcttg gaagcagcca tccttgaaag agtgcgtaat agctcactgg   1200
tcaagtgatt ccgcgccgac aatgtagcgg ggctcaagcc atccgccgaa gctgtggcaa   1260
tcaggattta ctcctggttg ggtaggggag cgtcgtgttc tcggtgaagc ggtccggtga   1320
cgggtcgtgg aggggatgcg agtgagaatg caggcatgag tagcgaatga cgggtgagaa   1380
acccgtccgc cgaatatcca agggttccag ggtcaagtta atcttccctg ggtgagtcgg   1440
gacctaaggc gaggccgaca ggcgtagtcg atggacgacc agttgatatt ctggtaccgg   1500
tgtagcaccg tccgtgtcga ggtgtgtgat gctaagcatg cgagtccctg ttccgcgggc   1560
ctttggtctg tggggtgggt ggtgagtgtg tgaaccgatc atgtagtagg caagctgcgg   1620
agggacgcag ggaggtagct caaccccagc gatggttgtc tggggctaaa cgtgtggacc   1680
gtccggtagg taaatccgcc gggcatgatg gttgaggcgt gatggcgagc ccactgtgtg   1740
ggtgagtgag tgatcctgta ctgccagaaa aagcttcgtg agcgaggtgt gagccgcccg   1800
taccctaaac cgacactggt ggattggtag agtataccga ggcgatcgag agaatcatgg   1860
tgaaggaact cggcaaaatg accccgtaac ttcgggataa ggggtgcccg aaccgtccgg   1920
ctgtttactg gctgggggcg gtgagggtcg cagagtccag ggggaaacga ctgtttacta   1980
aaaacacagg tccgtgcgaa gttgtaagac gatgtatacg gactgactcc tgcccggtgc   2040
tggaaggtta aggggaactg tcagggcctt cgggttcgaa gcggtgaact taagcccag   2100
taaacggcgg tggtaactat aaccatccta aggtagcgaa attccttgtc gggtaagttc   2160
```

-continued

```
cgacctgcac gaatggagta acgatttccc tactgtctcc accatgaact cggtgaaatt    2220
gcattacgag taaagatgct cgttacgcgc agcaggacgg aaagaccccg ggacctttac    2280
tatagtttgg tattggtgat cggtgcgact tgtgtaggat aggtgggaga cggtgaagcg    2340
gccacgccag tggttgtgga gtcattgttg aaataccact ctggtcgttc tggttacctc    2400
acctcggacc gtgatccggt tcagggacag tgcctgatgg gtagtttgac tggggcggtc    2460
gcctcctaaa aggtaacgga ggcgcccaaa ggttccctca gcctggttgg taatcaggtg    2520
tcgagtgtaa gtgcacaagg gagcttgact gtgagacagg catgtcgagc agggacgaga    2580
gtcgggacta gtgatctgac ggtggcttgt ggaagtgccg tcactcaacg gataaaaggt    2640
accccgggga taacaggctg atcttgcccg agcgctcaca gcgacggcat ggtttggcac    2700
ctcgatgtcg gctcgtcgca tcctgggggct ggagtcggtc ccaagggttg gctgttcgc    2760 ccattaaagc ggcacgcgag ctgggtttag aacgtcgtga gacagttcgg tccctatccg    2820
ctgcgcgcac aggaatcttg agaagagctg tctctagtac gagaggaccg agacggactg    2880
acctctggtg tgccagttgt tccgccagga gcatggctgg ttggctacgt cgggtcgtga    2940
taaccgctga agcatctaa gcgggaagca cgcttcaaga tgagggttcc cacagatgaa    3000
tctggtaagg cccccgagag atgatcgggt tgataggccg gacgtggacg cactgcaagg    3060
tgcggagctg accggtacta ataggccgag ggcttgcccc aca                      3103
```

<210> SEQ ID NO 4
<211> LENGTH: 2335
<212> TYPE: DNA
<213> ORGANISM: Propionibacterium acidi-propionici

<400> SEQUENCE: 4

```
atgaacacgg ccgagtatct ggtcggcgac ggcgagtcgg gatcggtggc ggtggtggac      60
tccgacgggg tgcacagcta tgccgacctc cgcgcgcagg cgtcgaggtg ccgtgccgcc     120
ctcgaggaac tcgggttgcg cgccggcgac cgcgtcgggc tgatcggcgc gaactgcttc     180
ggctgggtgg ccgcctacct ggggggtgctg gccgccggca tggtcgccgt gccgatcgcc     240 catacccctgc gccccgacga gatcgtctcc agaatccggt ggctcggcgt ccaggccgcc     300
ttcctgggcc cgatggagtc gcgccgactc gccggacagg tcccggggggg tcttcctatg     360 gccgccgagg gtccgtcgcc ggcgggcccc ccgctgcgat tcgtcgatcg gcccgccgat     420
ctggacgccg ccctggtgtt cacctcgggc accaccggcc ggccgcacgt cgtgcggctc     480
acccacgcca acctgcaggc caacaccggc tccatcctga gctatctgcc gctggcagat     540
tcggatcgag tccttgtcgt gctgcccttc agctacgtct tcggggcctc cctgctgcac     600
acccacctga gggtgggagc ggccctggtg gtgcagccga acgccgcctt cccccagcag     660
atggtcgagc ggatggccgc cgagcgatgc accggcctcg cgggggtgcc ctccaccttc     720
tcggtgctgc tgcgcaacag caccttcggc tcccgtcggc tgcccgacct gcgcatcatc     780
cagcaggccg gcggcaggct cgcgccgacg atggtcgagc agttgcgcgg ggcccagccc     840
caggcgcagg tgttcgtgat gtacgggcag accgaggcca ccgcgcggct gtcctacctg     900 ccgcccagc agctggatcg ccgtccgggg tcgatcggcc ggggaatacc gggagtggac      960
ctgcgcgtgg tcggcgagga cggctcgcag gtcgccgccg acagatcgg cgagatcgtg     1020 gccgcggggg acaatatctc gcccggctac ctcgacgacc ccgaggagac cgccggcgg     1080 atgcccggag gggtactgcg gaccggcgat ctggcgacgg tcgacgagga cggttacatc     1140
tacgtcgtcg atcgcaggga ggacttcatc aagtcgtggg gggtgaggat ctcgagtcag     1200
```

-continued

```
gacatcgagg cggtggcgct gcagctcacc gatctcgtgt cggtggctgc ggtgggagtg    1260
cccgacgagg ccgccgggga gcgggtcgag ttggtggccg tgccccggga ggggtcgcgg    1320
ctcaccgagg ccagatcat cgaccactgc cgggcccggc tggctaggac catggtgccg    1380
caggccgtgc atcttgtccc gttgatgccc ctcaacggca acggtaaaat ctccaagaca    1440
gcggtccgcg aactctgcgt ggatctggcc agagccgacc agtccccagg aggatcatca    1500
tgaggcggaa accagtcgtc gtcctgatcg caggcgtcct cgcggtggtg gtcgccagcg    1560
gcgcatgggt gctgcagggc aggcccgacc cgctgccctc ctcggtggtg aacacggccg    1620
ccggcgacga cgagctcgcc gatttcagcg gcgaggat cttcttcggt caccagtccg    1680
tcggggcgaa catcatcgat ggtctgaaag ccgcctattc gggccgggag ggctccggcc    1740
tcgacgttgt cgagacgcgc accgatccag gcaggagcgg cggatacctg cccatgccg    1800 cgatgggggt caacggcgac ccgctcggca aactcgccga tttcgagaag gtgctggccg    1860
gctcgatggg cggcgcggtc gacctcgccg tgctcaagct gtgctacatc gacgtcacgg    1920
ccgacaccga cgtcgacgcg ctgttcacgg cgtactcgca gaccatgacc aggctcgagg    1980
ccgcccatcc gggggtcacc ttcatctaca cgacagtccc gctgaccacc gaccggacct    2040
ggaagcagac cgtcaagtcg tggatcgggc gcgacgagca gacggggccg gacgacaacg    2100
ccgcccgcca gcgttacaac cggctcgtgc gcgagcggta cggcgattcc gacaggctct    2160
tcgacatcgc cgcggtccag gccacgatgg acagctcccc gacctcgcgg acccgtgacg    2220
gatccaccta ctacgtcctt cacgaccggc tggcggccga ccccgggccc tcaacgcgct    2280
ggggtcacgg gtgaccgccg cccgcctcgt gcacctggtg gccgcacagc actag          2335
```

<210> SEQ ID NO 5
<211> LENGTH: 779
<212> TYPE: PRT
<213> ORGANISM: Propionibacterium acidi-propionici
<220> FEATURE:
<221> NAME/KEY: MISC_FEATURE
<222> LOCATION: (501)..(501)
<223> OTHER INFORMATION: Xaa at position 501 is unknown
<220> FEATURE:
<221> NAME/KEY: misc_feature
<222> LOCATION: (509)..(509)
<223> OTHER INFORMATION: Xaa can be any naturally occurring amino acid
<220> FEATURE:
<221> NAME/KEY: misc_feature
<222> LOCATION: (537)..(537)
<223> OTHER INFORMATION: Xaa can be any naturally occurring amino acid
<220> FEATURE:
<221> NAME/KEY: misc_feature
<222> LOCATION: (569)..(569)
<223> OTHER INFORMATION: Xaa can be any naturally occurring amino acid
<220> FEATURE:
<221> NAME/KEY: misc_feature
<222> LOCATION: (656)..(656)
<223> OTHER INFORMATION: Xaa can be any naturally occurring amino acid
<220> FEATURE:
<221> NAME/KEY: misc_feature
<222> LOCATION: (675)..(675)
<223> OTHER INFORMATION: Xaa can be any naturally occurring amino acid
<220> FEATURE:
<221> NAME/KEY: misc_feature
<222> LOCATION: (779)..(779)
<223> OTHER INFORMATION: Xaa can be any naturally occurring amino acid

<400> SEQUENCE: 5

```
Met Asn Thr Ala Glu Tyr Leu Val Gly Asp Gly Glu Ser Gly Ser Val
1               5                   10                  15

Ala Val Val Asp Ser Asp Gly Val His Ser Tyr Ala Asp Leu Arg Ala
```

-continued

```
                20                  25                  30
Gln Ala Ser Arg Cys Arg Ala Ala Leu Glu Glu Leu Gly Leu Arg Ala
            35                  40                  45
Gly Asp Arg Val Gly Leu Ile Gly Ala Asn Cys Phe Gly Trp Val Ala
    50                  55                  60
Ala Tyr Leu Gly Val Leu Ala Ala Gly Met Val Ala Val Pro Ile Ala
65                  70                  75                  80
His Thr Leu Arg Pro Asp Glu Ile Val Ser Arg Ile Arg Trp Leu Gly
                85                  90                  95
Val Gln Ala Ala Phe Leu Gly Pro Met Glu Ser Arg Arg Leu Ala Gly
            100                 105                 110
Gln Val Pro Gly Gly Leu Pro Met Ala Ala Glu Gly Pro Ser Pro Ala
        115                 120                 125
Gly Pro Pro Leu Arg Phe Val Asp Arg Pro Ala Asp Leu Asp Ala Ala
    130                 135                 140
Leu Val Phe Thr Ser Gly Thr Thr Gly Arg Pro His Val Val Arg Leu
145                 150                 155                 160
Thr His Ala Asn Leu Gln Ala Asn Thr Gly Ser Ile Leu Ser Tyr Leu
                165                 170                 175
Pro Leu Ala Asp Ser Asp Arg Val Leu Val Leu Pro Phe Ser Tyr
            180                 185                 190
Val Phe Gly Ala Ser Leu Leu His Thr His Leu Arg Val Gly Ala Ala
        195                 200                 205
Leu Val Val Gln Pro Asn Ala Ala Phe Pro Gln Gln Met Val Glu Arg
    210                 215                 220
Met Ala Ala Glu Arg Cys Thr Gly Leu Ala Gly Val Pro Ser Thr Phe
225                 230                 235                 240
Ser Val Leu Leu Arg Asn Ser Thr Phe Gly Ser Arg Arg Leu Pro Asp
                245                 250                 255
Leu Arg Ile Ile Gln Gln Ala Gly Gly Arg Leu Ala Pro Thr Met Val
            260                 265                 270
Glu Glu Leu Arg Gly Ala Gln Pro Gln Ala Gln Val Phe Val Met Tyr
        275                 280                 285
Gly Gln Thr Glu Ala Thr Ala Arg Leu Ser Tyr Leu Pro Pro Gln Glu
    290                 295                 300
Leu Asp Arg Arg Pro Gly Ser Ile Gly Arg Gly Ile Pro Gly Val Asp
305                 310                 315                 320
Leu Arg Val Val Gly Glu Asp Gly Ser Gln Val Ala Ala Gly Gln Ile
                325                 330                 335
Gly Glu Ile Val Ala Gly Gly Asp Asn Ile Ser Pro Gly Tyr Leu Asp
            340                 345                 350
Asp Pro Glu Glu Thr Ala Arg Met Pro Gly Gly Val Leu Arg Thr
        355                 360                 365
Gly Asp Leu Ala Thr Val Asp Glu Asp Gly Tyr Ile Tyr Val Val Asp
    370                 375                 380
Arg Arg Glu Asp Phe Ile Lys Ser Trp Gly Val Arg Ile Ser Ser Gln
385                 390                 395                 400
Asp Ile Glu Ala Val Ala Leu Gln Leu Thr Asp Leu Val Ser Val Ala
                405                 410                 415
Ala Val Gly Val Pro Asp Glu Ala Ala Gly Glu Arg Val Glu Leu Val
            420                 425                 430
Ala Val Pro Arg Glu Gly Ser Arg Leu Thr Glu Gly Gln Ile Ile Asp
        435                 440                 445
```

His Cys Arg Ala Arg Leu Ala Arg Thr Met Val Pro Gln Ala Val His
            450                 455                 460

Leu Val Pro Leu Met Pro Leu Asn Gly Asn Gly Lys Ile Ser Lys Thr
465                 470                 475                 480

Ala Val Arg Glu Leu Cys Val Asp Leu Ala Arg Ala Asp Gln Ser Pro
                485                 490                 495

Gly Gly Ser Ser Xaa Gly Gly Asn Gln Ser Ser Ser Xaa Ser Gln Ala
            500                 505                 510

Ser Ser Arg Trp Trp Ser Pro Ala Ala His Gly Cys Cys Arg Ala Gly
            515                 520                 525

Pro Thr Arg Cys Pro Pro Arg Trp Xaa Thr Arg Pro Pro Ala Thr Thr
            530                 535                 540

Ser Ser Pro Ile Ser Ala Gly Gly Ser Ser Ser Val Thr Ser Pro
545                 550                 555                 560

Ser Gly Arg Thr Ser Ser Met Val Xaa Lys Pro Pro Ile Arg Ala Gly
                565                 570                 575

Arg Ala Pro Ala Ser Thr Leu Ser Arg Arg Ala Pro Ile Gln Ala Gly
            580                 585                 590

Ala Ala Asp Thr Trp Pro Met Pro Arg Trp Gly Ser Thr Ala Thr Arg
            595                 600                 605

Ser Ala Asn Ser Pro Ile Ser Arg Arg Cys Trp Pro Ala Arg Trp Ala
610                 615                 620

Ala Arg Ser Thr Ser Pro Cys Ser Ser Cys Ala Thr Ser Thr Ser Arg
625                 630                 635                 640

Pro Thr Pro Thr Ser Thr Arg Cys Ser Arg Arg Thr Arg Arg Pro Xaa
                645                 650                 655

Pro Gly Ser Arg Pro Pro Ile Arg Gly Ser Pro Ser Thr Arg Gln
            660                 665                 670

Ser Arg Xaa Pro Pro Thr Gly Pro Gly Ser Arg Pro Ser Ser Arg Gly
            675                 680                 685

Ser Gly Ala Thr Ser Arg Arg Gly Arg Thr Thr Thr Pro Pro Ala Ser
690                 695                 700

Val Thr Thr Gly Ser Cys Ala Ser Gly Thr Ala Ile Pro Thr Gly Ser
705                 710                 715                 720

Ser Thr Ser Pro Arg Ser Arg Pro Arg Trp Thr Ala Pro Arg Pro Arg
                725                 730                 735

Gly Pro Val Thr Asp Pro Pro Thr Thr Ser Phe Thr Thr Gly Trp Arg
            740                 745                 750

Pro Thr Pro Gly Pro Gln Arg Ala Gly Val Thr Gly Asp Arg Arg Pro
            755                 760                 765

Pro Arg Ala Pro Gly Gly Arg Thr Ala Leu Xaa
770                 775

<210> SEQ ID NO 6
<211> LENGTH: 3103
<212> TYPE: DNA
<213> ORGANISM: Propionibacterium acidi-propionici

<400> SEQUENCE: 6
gttgcaagct actaagtgcg gtcggtggat gccttggcac caagagccga tgaaggacgt      60
tgtaacctgc gataagcccc ggggagttgg ttcacgagct gtgatccggg ggtgtccgaa     120
tggggaaacc ttgaattgcc ggagtcatgt ccggtgaccc tgccctgaat gtataggggt     180
gtgggaggga acgtggggaa gtgaaacatc tcagtacccg caggaagaga aacaatatg      240

```
tgattccgtg agtagtggcg agcgaaagcg gatgaggcca aaccgtgtgt gtgttcaaac    300
cggcaggtgt tgcacgtgcg gggttgtggg gtcttctggg atcgactgcc gtcggtccgt    360
ccagtgataa atggtgtgtt gaagtcgaag cgtctgggaa ggcgtaccgg agtgggtgag    420
agtcccgtag acgtggatgc accactggtg gaggataccc caagtagcgc gggactcgtg    480
gaatttcgcg tgaatctggc gggaccaccc gtcaagcctg aatactcctt ggtgaccgat    540
agtggatagt accgtgaggg aatggtgaaa agtaccccgg gagggagtg  aaagagtacc    600 tgaaaccggc cgcatacaat ccgtcggagc ctgcctgtac gggtgggtga cggcgtgcct    660
attgaagaat gagcctgcga gttagtggca tgtggcgagg ttaacccgtg tggggtagtc    720
gtagcgaaag cgagtccgat aagggcgcca gtcgcgtgtt ctagacccga agcggtgtga    780
tctatccatg gccaggatga agcgacggta agacgtcgtg gaggtccgca cccacttcag    840
ttgaaaatgg aggggatgag ctgtggatag gggtgaaagg ccaatcaaac actgtgatag    900
ctggttctcc ccgaaatgca tttaggtgca gcgtcgcgtg gttcttgctg gaggtagagc    960
actggatgat ctagggggcc tatcagctta ccgaaatcag ccaaactccg aatgccggca   1020
agtggagcgt ggcagtgaga cggcggggga taagcttcgt cgtcgagagg gaaacagccc   1080
agatcatcag ctaaggcccc taagcggtgg ctaagtggaa aaggatgtgg agttgcggtg   1140
acaaccagga ggttggcttg gaagcagcca tccttgaaag agtgcgtaat agctcactgg   1200
tcaagtgatt ccgcgccgac aatgtagcgg ggctcaagcc atccgccgaa gctgtggcaa   1260
tcaggattta ctcctggttg ggtagggag  cgtcgtgttc tcggtgaagc ggtccggtga   1320
cgggtcgtgg aggggatgcg agtgagaatg caggcatgag tagcgaatga cgggtgagaa   1380
acccgtccgc cgaatatcca agggttccag ggtcaagtta atcttccctg ggtgagtcgg   1440
aacctaaggc gaggccgaca ggcgtagtcg atggacgacc agttgatatt ctggtaccgg   1500
tgtagcaccg tccgtgtcga ggtgtgtgat gctaagcatg cgagtccctg ttccgcgggc   1560
ctttggtctg tggggtgggt ggtgagtgtg tgaaccgatc atgtagtagg caagctgcgg   1620
agggacgcag ggaggtagct caacccccagc gatggttgtc tggggctaaa cgtgtggacc   1680
gtccggtagg taaatccgcc gggcatgatg gttgaggcgt gatggcgagc ccactgtgtg   1740
ggtgagtgag tgatcctgta ctgccgagaa aagcttcgtg agcgaggtgt gagccgcccg   1800
taccctaaac cgacactggt ggattggtag agtataccga ggcgatcgag agaatcatgg   1860
tgaaggaact cggcaaaatg accccgtaac ttcgggataa ggggtgcccg aaccgtccgg   1920
ctgtttactg gctgggggcg gtgagggtcg cagagtccag ggggaaacga ctgtttacta   1980
aaaacacagg tccgtgcgaa gttgtaagac gatgtatacg gactgactcc tgcccggtgc   2040
tggaaggtta aggggaactg tcagggcctt cgggttcgaa gcggtgaact taagcccag    2100 taaacggcgg tggtaactat aaccatccta aggtagcgaa attccttgtc gggtaagttc   2160
cgacctgcac gaatggagta acgatttccc tactgtctcc accatgaact cggtgaaatt   2220
gcattacgag taaagatgct cgttacgcgc agcaggacgg aaagaccccg ggacctttac   2280
tatagtttgg tattggtgat cggtgcgact tgtgtaggat aggtgggaga cggtgaagcg   2340
gccacgccag tggttgtgga gtcattgttg aaataccact ctggtcgttc tggttacctc   2400
acctcggacc gtgatccggt tcagggacag tgcctgatgg gtagtttgac tggggcggtc   2460
gcctcctaaa aggtaacgga ggcgcccaaa ggttccctca gcctggttgg taatcaggtg   2520
tcgagtgtaa gtgcacaagg gagcttgact gtgagacagg catgtcgagc agggacgaga   2580
```

```
gtcgggacta gtgatctgac ggtggcttgt ggaagtgccg tcactcaacg gataaaaggt    2640 accccggga taacaggctg atcttgcccg agcgctcaca gcgacggcat ggtttggcac    2700
ctcgatgtcg gctcgtcgca tcctggggct ggagtcggtc caagggttg gctgttcgc    2760 ccattaaagc ggcacgcgag ctgggtttag aacgtcgtga gacagttcgg tccctatccg    2820
ctgcgcgcac aggaatcttg agaagagctg tctctagtac gagaggaccg agacggactg    2880
acctctggtg tgccagttgt tccgccagga gcatggctgg ttggctacgt cgggtcgtga    2940
taaccgctga aagcatctaa gcgggaagca cgcttcaaga tgagggttcc cacagatgaa    3000
tctggtaagg cccccgagag atgatcgggt tgataggccg gacgtggacg cactgcaagg    3060
tgcggagctg accggtacta ataggccgag ggcttgcccc aca                      3103
```

<210> SEQ ID NO 7
<211> LENGTH: 2336
<212> TYPE: DNA
<213> ORGANISM: Propionibacterium acidi-propionici

<400> SEQUENCE: 7

```
atgaacacgg ccgagtatct ggtcggcgac ggcgagtcgg gatcggtggc ggtggtggac     60
tccgacgggg tgcacagcta tgccgacctc cgcgcgcagg cgtcgaggtg ccgtgccgcc    120
ctcgaggaac tcgggttgcg cgccggcgac cgcgtcgggc tgatcggcgc gaactgcttc    180
ggctgggtgg ccgcctacct gggggtgctg ccgccggca tggtcgccgt gccgatcgcc     240
cataccctgc gccccgacga gatcgtctcc agaatccggt ggctcggcgt ccaggccgcc    300
ttcctgggcc cgatggagtc gcgccgactc gccggacagg tccggggggg tcttcctatg    360
gccgccgagg gtccgtcgcc ggcgggcccc ccgctgcgat tcgtcgatcg gcccgccgat    420
ctggacgccg cctggtgtt cacctcgggc accaccggcc ggccgcacgt cgtgcggctc    480
acccacgcca acctgcaggc caacaccggc tccatcctga gctatctgcc gctggcagat    540
tcggatcgag tccttgtcgt gctgcccttc agctacgtct cggggcctc cctgctgcac     600 acccacctga gggtgggagc ggccctggtg gtgcagccga acgccgcctt ccccccagcag    660 atggtcgagc ggatggccgc cgagcgatgc accggcctcg cggggtgcc ctccaccttc     720 tcggtgctgc tgcgcaacag caccttcggc tcccgtcggc tgcccgacct cgcatcatc     780 cagcaggccg gcggcaggct cgcgccgacg atggtcgagg agttgcgcgg ggcccagccc    840
caggcgcagg tgttcgtgat gtacgggcag accgaggcca ccgcgcggct gtcctacctg     900
ccgccccagg agctggatcg ccgtccgggg tcgatcggcc ggggaatacc gggagtggac    960
ctgcgcgtgg tcggcgagga cggctcgcag gtcgccgccg acagatcgg cgagatcgtg   1020 gccggcgggg acaatatctc gcccggctac ctcgacgacc ccgaggagac cgcccggcgg   1080
atgcccggag gggtactgcg gaccggcgat ctggcgacgg tcgacgagga cggttacatc   1140
tacgtcgtcg atcgcaggga ggacttcatc aagtcgtggg gggtgaggat ctcgagtcag   1200
gacatcgagg cggtggcgct gcagctcacc gatctcgtgt cggtggctgc ggtgggagtg   1260
cccgacgagg ccgccgggga gcgggtcgag ttggtggccg tgccccggga ggggtcgcgg   1320
ctcaccgagg ccagatcat cgaccactgc cgggcccggc tggctaggac catggtgccg   1380
caggccgtgc atcttgtccc gttgatgccc ctcaacggca acggtaaaat ctccaagaca   1440
gcggtccgcg aactctgcgt ggatctggcc agagccgacc agtccccagg aggatcatca   1500
atgaggcgga aaccagtcgt cgtcctgatc gcaggcgtcc tcgcggtggt ggtcgccagc   1560
ggcgcatggg tgctgcaggg caggcccgac ccgctgccct cctcggtggt gaacacggcc   1620
```

```
gccggcgacg acgagctcgc cgatttcagc gggcggagga tcttcttcgg tcaccagtcc   1680 gtcgggcga acatcatcga tggtctgaaa gccgcctatt cgggccggga gggctccggc    1740
ctcgacgttg tcgagacgcg caccgatcca ggcaggagcg gcggatacct ggcccatgcc   1800
gcgatggggg tcaacggcga cccgctcggc aaactcgccg atttcgagaa ggtgctggcc   1860
ggctcgatgg gcggcgcggt cgacctcgcc gtgctcaagc tgtgctacat cgacgtcacg   1920
gccgacaccg acgtcgacgc gctgttcacg gcgtactcgc agaccatgac caggctcgag   1980
gccgcccatc cggggtcac cttcatctac acgacagtcc cgctgaccac cgaccggacc    2040
tggaagcaga ccgtcaagtc gtggatcggg cgcgacgagc agacggggcc ggacgacaac   2100
gccgcccgcc agcgttacaa ccggctcgtg cgcgagcggt acggcgattc cgacaggctc   2160
ttcgacatcg ccgcggtcca ggccacgatg gacagctccc cgacctcgcg gacccgtgac   2220
ggatccacct actacgtcct tcacgaccgg ctggcggccg accccgggcc ctcaacgcgc   2280
tggggtcacg ggtgaccgcc gcccgcctcg tgcacctggt ggccgcacag cactag       2336
```

<210> SEQ ID NO 8
<211> LENGTH: 500
<212> TYPE: PRT
<213> ORGANISM: Propionibacterium acidi-propionici

<400> SEQUENCE: 8

```
Met Asn Thr Ala Glu Tyr Leu Val Gly Asp Gly Glu Ser Gly Ser Val
1               5                   10                  15

Ala Val Val Asp Ser Asp Gly Val His Ser Tyr Ala Asp Leu Arg Ala
            20                  25                  30

Gln Ala Ser Arg Cys Arg Ala Ala Leu Glu Glu Leu Gly Leu Arg Ala
        35                  40                  45

Gly Asp Arg Val Gly Leu Ile Gly Ala Asn Cys Phe Gly Trp Val Ala
    50                  55                  60

Ala Tyr Leu Gly Val Leu Ala Ala Gly Met Val Ala Val Pro Ile Ala
65                  70                  75                  80

His Thr Leu Arg Pro Asp Glu Ile Val Ser Arg Ile Arg Trp Leu Gly
                85                  90                  95

Val Gln Ala Ala Phe Leu Gly Pro Met Glu Ser Arg Arg Leu Ala Gly
            100                 105                 110

Gln Val Pro Gly Gly Leu Pro Met Ala Ala Glu Gly Pro Ser Pro Ala
        115                 120                 125

Gly Pro Pro Leu Arg Phe Val Asp Arg Pro Ala Asp Leu Asp Ala Ala
    130                 135                 140

Leu Val Phe Thr Ser Gly Thr Thr Gly Arg Pro His Val Val Arg Leu
145                 150                 155                 160

Thr His Ala Asn Leu Gln Ala Asn Thr Gly Ser Ile Leu Ser Tyr Leu
                165                 170                 175

Pro Leu Ala Asp Ser Asp Arg Val Leu Val Leu Pro Phe Ser Tyr
            180                 185                 190

Val Phe Gly Ala Ser Leu Leu His Thr His Leu Arg Val Gly Ala Ala
        195                 200                 205

Leu Val Val Gln Pro Asn Ala Ala Phe Pro Gln Gln Met Val Glu Arg
    210                 215                 220

Met Ala Ala Glu Arg Cys Thr Gly Leu Ala Gly Val Pro Ser Thr Phe
225                 230                 235                 240

Ser Val Leu Leu Arg Asn Ser Thr Phe Gly Ser Arg Arg Leu Pro Asp
```

```
            245                 250                 255
Leu Arg Ile Ile Gln Gln Ala Gly Gly Arg Leu Ala Pro Thr Met Val
                260                 265                 270
Glu Glu Leu Arg Gly Ala Gln Pro Gln Ala Gln Val Phe Val Met Tyr
            275                 280                 285
Gly Gln Thr Glu Ala Thr Ala Arg Leu Ser Tyr Leu Pro Pro Gln Glu
        290                 295                 300
Leu Asp Arg Arg Pro Gly Ser Ile Gly Arg Gly Ile Pro Gly Val Asp
305                 310                 315                 320
Leu Arg Val Val Gly Glu Asp Gly Ser Gln Val Ala Ala Gly Gln Ile
                325                 330                 335
Gly Glu Ile Val Ala Gly Gly Asp Asn Ile Ser Pro Gly Tyr Leu Asp
                340                 345                 350
Asp Pro Glu Glu Thr Ala Arg Arg Met Pro Gly Val Leu Arg Thr
            355                 360                 365
Gly Asp Leu Ala Thr Val Asp Glu Asp Gly Tyr Ile Tyr Val Val Asp
        370                 375                 380
Arg Arg Glu Asp Phe Ile Lys Ser Trp Gly Val Arg Ile Ser Ser Gln
385                 390                 395                 400
Asp Ile Glu Ala Val Ala Leu Gln Leu Thr Asp Leu Val Ser Val Ala
                405                 410                 415
Ala Val Gly Val Pro Asp Glu Ala Ala Gly Glu Arg Val Glu Leu Val
            420                 425                 430
Ala Val Pro Arg Glu Gly Ser Arg Leu Thr Glu Gly Gln Ile Ile Asp
        435                 440                 445
His Cys Arg Ala Arg Leu Ala Arg Thr Met Val Pro Gln Ala Val His
    450                 455                 460
Leu Val Pro Leu Met Pro Leu Asn Gly Asn Gly Lys Ile Ser Lys Thr
465                 470                 475                 480
Ala Val Arg Glu Leu Cys Val Asp Leu Ala Arg Ala Asp Gln Ser Pro
                485                 490                 495
Gly Gly Ser Ser
            500

<210> SEQ ID NO 9
<211> LENGTH: 3103
<212> TYPE: RNA
<213> ORGANISM: Propionibacterium acidi-propionici

<400> SEQUENCE: 9
guugcaagcu acuaagugcg gucgguggau gccuuggcac aagagccga ugaaggacgu      60 uguaaccugc gauaagcccc ggggaguugg uucacgagcu ugauccggg ggguguccgaa    120 uggggaaacc uugaauugcc ggagucaugu ccggugaccc ugcccugaau guauaggggu    180
gugggaggga acgugggaa ugaaacauc ucaguacccg caggaagaga aaacaauaug     240
ugauuccgug aguagguggcg agcgaaagcg gaugaggcca aaccgugugu guguucaaac    300
cggcaggugu ugcacgugcg ggguuguggg gucuucuggg aucgacugcc gucggucgu    360 ccagugauaa auggugguguu gaagucgaag cgucugggaa ggcguaccgg aguggguggag    420 agucccguag acguggaugc accacugguug gaggauaccc caaguagcgc gggacucgug    480
gaauuucgcg ugaaucuggc gggaccaccc gucaagccug aauacuccuu ggugaccgau    540
aguggauagu accgugaggg aauggugaaa aguaccccgg gaggggaguG aaagaguacc    600
ugaaaccggc cgcauacaau ccgucggagc cugccuguac ggguggguga cggcguggcu    660
```

-continued

```
auugaagaau gagccugcga guuaguggca uguggcgagg uuaacccgug uggguaguc      720 guagcgaaag cgaguccgau aagggcgcca gucgcguguu cuagacccga agcgguguga    780
ucuauccaug gccaggauga agcgacggua agacgucgug gagguccgca cccacuucag    840
uugaaaaugg agggaugag cuguggauag gggugaaagg ccaaucaaac acugugauag     900
cugguucucc ccgaaaugca uuuaggugca gcgucgcgug guucuugcug gagguagagc   960
acuggaugau cuaggggcc uaucagcuua ccgaaaucag ccaaacuccg aaugccggca   1020
aguggagcgu ggcagugaga cggcggggga uaagcuucgu cgucgagagg gaaacagccc  1080
agaucaucag cuaaggcccc uaagcggugg cuaaguggaa aaggaugugg aguugcggug  1140
acaaccagga gguuggcuug gaagcagcca uccuugaaag agugcguaau agcucacugg  1200
ucaagugauu ccgcgccgac aauguagcgg ggcucaagcc auccgccgaa gcuguggcaa  1260
ucaggauuua cuccugguug gguaggggag cgucuguuc ucggugaagc gguccggcga  1320
cgggucgugg agggaugcg agugagaaug caggcaugaa uagcgaauga cgggugagaa   1380
acccguccgc cgaauauccca aggguuccag ggucaaguua aucuucccug ggugagucgg  1440
gaccuaaggc gaggccgaca ggcguagucg auggacgacc aguugauauu cugguaccgg  1500
uguagcaccg uccgugucga ggugugugau gcuaagcaug cgaguccug uuccgcgggc   1560 cuuggucug ugggguggu ggugagugug ugaaccgauc auguaguagg caagcugcgg    1620
agggacgcag ggagguagcu caaccccagc gauguugguc ugggcuaaa cguguggacc   1680 guccggauagg uaaauccgcc gggcaugaug guugaggcgu gauggcgagc ccacugugug  1740
ggugagugag ugauccugua cugccgagaa aagcuucgug agcgaggugu gagccgcccg   1800
uaccuaaaac cgacacuggu ggauuggag aguauaccga ggcgaucgag agaaucaugg   1860
ugaaggaacu cggcaaaaug accccguaac uucgggauaa ggggugcccg aaccguccgg   1920
cuguuuacug gcuggggcg gugagggucg cagaguccag ggggaaacga cuguuuacua   1980
aaaacacagg uccgugcgaa guuguaagac gauguauacg gacugacucc ugcccggugc   2040
uggaagguua aggggaacug ucaggggccuu cggguucgaa gcggugaacu uaagccccag   2100
uaaacggcgg ugguaacuau aaccauccua agguagcgaa auuccuuguc ggguaaguuc   2160
cgaccugcac gaauggagua acgauuuccc uacugucucc accaugaacu cggugaaauu   2220
gcauuacgag uaaagaugcu cguuacgcgc agcaggacgg aaagaccccg ggaccuuuac   2280
uauaguuugg uauuggugau cggugcgacu uguguaggau aggugggaga cggugaagcg   2340
gccacgccag gguugugga ucauugguug aaauaccacu cuggcgguuc gguuaccuc    2400 accucggacc gugauccggu ucagggacag ugccugaugg guaguugac uggggcgguc   2460 gccuccuaaa agguaacgga ggcgcccaaa gguucccuca gccugguugg uaaucaggug   2520
ucgaguguaa gugcacaagg gagcuugacu gugagacagg caugucgagc agggacgaga   2580
gucgggacua gugaucugac ggguggcuugu ggaagugccg ucacucaacg gauaaaaggu   2640
accccgggga uaacaggcug aucuugcccg agcgcucaca gcgacggcau gguuuggcac   2700
cucgaugucg gcucgucgca uccuggggcu ggagucgguc ccaaggguug gcuguucgc   2760 ccauuaaagc ggcacgcgag cugggguuag aacgucguga gacaguucgg ucccuauccg   2820
cugcgcgcac aggaaucuug agaagagcug ucucaguac gagaggaccg agacggacug   2880
accucuggug ugccaguugu uccgccagga gcauggcugg uuggcuacgu cggguucguga   2940 uaaccgcuga aagcaucuaa gcgggaagca cgcuucaaga ugaggguucc cacagaugaa   3000
```

```
ucugguaagg cccccgagag augaucgggu ugauaggccg gacguggacg cacugcaagg    3060
ugcggagcug accgguacua auaggccgag ggcuugcccc aca                     3103
```

<210> SEQ ID NO 10
<211> LENGTH: 326
<212> TYPE: PRT
<213> ORGANISM: Propionibacterium acidi-propionici

<400> SEQUENCE: 10

```
Ser Asp Val Gln Ile Leu Ile Gly Pro Gly Val Leu Asp Arg Phe Gln
1               5                   10                  15

Val Ala His His Pro Gln Ile Gly Pro Leu Val Glu Glu Phe Val Asp
            20                  25                  30

Glu Val Leu His Asp Val Val Ala Val Leu Asn Gly Pro Leu Thr Gly
        35                  40                  45

Asp Gln His Val Glu Leu Gln Glu Pro Pro Ile Ala Gly Leu Pro Gly
    50                  55                  60

Ala Asp Gly Val Glu Gly Asn Pro Leu Ala Ala Val Leu Val Gln Glu
65                  70                  75                  80

Leu Pro Asp Gly Gly Val Val Gly Leu Arg Gln Gly Asp Val His Gln
                85                  90                  95

Pro Cys Ala Arg Leu Ala Asp Glu Ser Gly Pro Gly Asp Glu Asp Ile
            100                 105                 110

Gln Ala His Arg Glu Gly His Asp Arg Val Gln Ser Leu Pro Ala Gly
        115                 120                 125

Glu Pro His Gln Ala Asp Ser His Asp His Ala Asp Arg Gly Asp Asp
    130                 135                 140

Val Gly Pro Gln Val Pro Thr Val Gly Gln Gln Gly His Arg Ala Thr
145                 150                 155                 160

Thr Pro Ala Val Ala His Glu Asp Arg Gly His Arg Ala Val Asp Asp
                165                 170                 175

Arg Gly Asp Arg Arg Asp His Gln Ala Gln Ser Gln Ile Leu Gln Ala
            180                 185                 190

Leu Gly Val Gln Glu Ala Val Asp Gly Arg Asp Gln Asp Asp Gly Arg
        195                 200                 205

Arg Asp Glu Asp His Asp Ala Leu Asp Arg Arg Gly Glu Val Leu Gly
    210                 215                 220

Leu Arg Val Pro Glu Leu Val Val Leu Val Arg Arg Leu Asp Gly His
225                 230                 235                 240

Leu Glu Gly His Gln Gly Asp Asp Arg Gly His Gln Val His His Arg
                245                 250                 255

Leu Gly Gly Val Arg Glu Gln Ala His Arg Ser Gly Glu Lys Pro Arg
            260                 265                 270

Ser Gly Leu Glu Glu Asp Gly Asp Arg Arg Arg Asp Arg Gln Pro
        275                 280                 285

Gly Glu Thr Ala Gln Val Leu Arg Arg Phe Val Ala Arg Gly Arg Val
    290                 295                 300

Gly Cys Arg Gly Asp Pro Gly Ala Ala His Arg Ala Asn Cys Ala Ser
305                 310                 315                 320

Val Arg Ala Ile Gly His
                325
```

<210> SEQ ID NO 11
<211> LENGTH: 978
<212> TYPE: DNA

<213> ORGANISM: Propionibacterium acidi-propionici

<400> SEQUENCE: 11

```
tcagacgtcc agatcctcgt aggaccgggg gtcctcgatc ggttccaggt ggcccatcac    60
ccgcagatcg ggccacttgt cgaggagttc gtcgatgagg tcctccatga cgtcgtggcc   120
gtgctgaacg gtccactcac cggggaccag catgtggaac tccaggaacc gccgatatcc   180
ggcctcccgg gtgcggatgg cgtggaaggc gacccgctcg ctgctgtgct ggtccaggaa   240
ctcccggatg gcggcattgt cggccttcgg cagggagacg tccatcagcc ctgcgcccga   300
ctggccgatg agtcgggccc cggtgacgag gatgttcagc cccaccgcga aggccacgat   360
cgggtccagt cgctgccagc cggtgagcca caccaggccg actccaacga ccacgccgat   420
cgaggtgacg acgtcggtcc acaggtgccg cccgtcggcc agcagggtca tcgagcgacg   480
acgtcggccg ttgcgcatga ggaccgcggc caccgagccg ttgatgaccg aggcgaccgc   540
cgagaccacc aggcccagtc ccagattctc cagaccctgg gggtgcagga agcggtcgac   600
ggccgagacc aggatgacgg ccgccgcgac gaagatcatg atgccctcga ccgccgcgga   660
gaagtactcg gccttcgagt gcccgaactg gtggttcttg tccggcggct tgatggacac   720
cttgagggcc accagggcga cgatcgcggc caccaggttc accaccgact cggcggcgtc   780
cgagagcagg cccaccgatc cggtgagaag ccacgctccg gtcttgagga ggatggtggc   840
gatcgccgcc gcgatcgaca gccaggcgaa acggctcagg tcctccggag gttcgtggcg   900
cggggccgag ttggctgtcg gggggatccg ggggctgctc accgcgccaa ttgtgccagc   960
gtccgggcga tcggccac                                                  978
```

<210> SEQ ID NO 12
<211> LENGTH: 3103
<212> TYPE: DNA
<213> ORGANISM: Propionibacterium acidi-propionici

<400> SEQUENCE: 12

```
gttgcaagct actaagtgcg gtcggtggat gccttggcac caagagccga tgaaggacgt    60
tgtaacctgc gataagcccc ggggagttgg ttcacgagct gtgatccggg ggtgtccgaa   120
tggggaaacc ttgaattgcc ggagtcatgt ccggtgaccc tgccctgaat gtatagggt    180
gtgggaggga acgtggggaa gtgaaacatc tcagtacccg caggaagaga aacaatatg    240
tgattccgtg agtagtggcg agcgaaagcg gatgaggcca aaccgtgtgt gtgttcaaac   300
cggcaggtgt tgcacgtgcg gggttgtggg gtcttctggg atcgactgcc gtcggtccgt   360
ccagtgataa atggtgtgtt gaagtcgaag cgtctgggaa ggcgtaccgg agtgggtgag   420
agtcccgtag acgtggatgc accactggtg gaggataccc caagtagcgc gggactcgtg   480
gaatttcgcg tgaatctggc gggaccaccc gtcaagcctg aatactcctt ggtgaccgat   540
agtggatagt accgtgaggg aatggtgaaa agtaccccgg gaggggagtg aaagagtacc   600
tgaaaccggc cgcatacaat ccgtcggagc ctgcctgtac gggtgggtga cggcgtgcct   660
attgaagaat gagcctgcga gttagtggca tgtggcgagg ttaacccgtg tggggtagtc   720
gtagcgaaag cgagtccgat aagggcgcca gtcgcgtgtt ctagacccga gcggtgtga   780
tctatccatg gccaggatga agcgacggta agacgtcgtg gaggtccgca cccacttcag   840
ttgaaaatgg aggggatgag ctgtggatag gggtgaaagg ccaatcaaac actgtgatag   900
ctggttctcc ccgaaatgca tttaggtgca gcgtcgcgtg gttcttgctg gaggtagagc   960
actgatgat ctagggggcc tatcagctta ccgaaatcag ccaaactccg aatgccggca  1020
```

```
agtggagcgt ggcagtgaga cggcggggga taagcttcgt cgtcgagagg gaaacagccc      1080
agatcatcag ctaaggcccc taagcggtgg ctaagtggaa aaggatgtgg agttgcggtg      1140
acaaccagga ggttggcttg gaagcagcca tccttgaaag agtgcgtaat agctcactgg      1200
tcaagtgatt ccgcgccgac aatgtagcgg ggctcaagcc atccgccgaa gctgtggcaa      1260
tcaggatttg ttcctggttg ggtaggggag cgtcgtgttc tcggtgaagc ggtccggtga      1320
cgggtcgtgg aggggatgcg agtgagaatg caggcatgag tagcgaatga cgggtgagaa      1380
acccgtccgc cgaatatcca agggttccag ggtcaagtta atctgccctg ggtgagtcgg      1440
gacctaaggc gaggccgaca ggcgtagtcg atggacgacc agttgatatt ctggtaccgg      1500
tgtagcaccg tccgtgtcga ggtgtgtgat gctaagcatg cgagtccctg ttccgcgggc      1560
ctttggtctg tggggtgggt ggtgagtgtg tgaaccgatc atgtagtagg caagctgcgg      1620
agggacgcag ggaggtagct caaccccagc gatggttgtc tggggctaaa cgtgtggacc      1680
gtccggtagg taaatccgcc gggcatgatg gttgaggcgt gatggcgagc ccactgtgtg      1740
ggtgagtgag tgatcctgta ctgccgagaa aagcttcgtg agcgaggtgt gagccgcccg      1800
taccctaaac cgacactggt ggattggtag agtataccga ggcgatcgag agaatcatgg      1860
tgaaggaact cggcaaaatg accccgtaac ttcgggataa ggggtgcccg aaccgtccgg      1920
ctgtttactg gctgggggcg gtgagggtcg cagagtccag ggggaaacga ctgtttacta      1980
aaaacacagg tccgtgcgaa gttgtaagac gatgtatacg gactgactcc tgcccggtgc      2040
tggaaggtta aggggaactg tcagggcctt cgggttcgaa gcggtgaact taagccccag      2100
taaacggcgg tggtaactat aaccatccta aggtagcgaa attccttgtc gggtaagttc      2160
cgacctgcac gaatggagta acgatttccc tactgtctcc accatgaact cggtgaaatt      2220
gcattacgag taaagatgct cgttacgcgc agcaggacgg aaagacccccg ggacctttac      2280 tatagtttgg tattggtgat cggtgcgact tgtgtaggat aggtgggaga cggtgaagcg      2340
gccacgccag tggttgtgga gtcattgttg aaataccact ctggtcgttc tggttacctc      2400
acctcggacc gtgatccggt tcagggacag tgcctgatgg gtagtttgac tggggcggtc      2460
gcctcctaaa aggtaacgga ggcgcccaaa ggttccctca gcctggttgg taatcaggtg      2520
tcgagtgtaa gtgcacaagg gagcttgact gtgagacagg catgtcgagc agggacgaga      2580
gtcgggacta gtgatctgac ggtggcttgt ggaagtgccg tcactcaacg gataaaaggt      2640
accccgggga taacaggctg atcttgcccg agcgctcaca gcgacggcat ggtttggcac      2700
ctcgatgtcg gctcgtcgca tcctgggggct ggagtcggtc ccaagggttg ggctgttcgc      2760
ccattaaagc ggcacgcgag ctgggtttag aacgtcgtga gacagttcgg tccctatccg      2820
ctgcgcgcac aggaatcttg agaagagctg tctctagtac gagaggaccg agacggactg      2880
acctctggtg tgccagttgt tccgccagga gcatggctgg ttggctacgt cgggtcgtga      2940
taaccgctga aagcatctaa gcgggaagca cgcttcaaga tgagggttcc cacagatgaa      3000
tctggtaagg cccccgagag atgatcgggt tgataggccg gacgtggacg cactgcaagg      3060
tgcggagctg accggtacta ataggccgag ggcttgcccc aca                       3103
```

<210> SEQ ID NO 13
<211> LENGTH: 978
<212> TYPE: DNA
<213> ORGANISM: Propionibacterium acidi-propionici

<400> SEQUENCE: 13

```
tcagacgtcc agatcctcat aggaccgggg gtcctcgatc ggttccaggt ggcccatcac      60
ccgcagatcg ggccacttgt cgaggagttc gtcgatgagg tcctccatga cgtcgtggcc     120
gtgctgaacg tccactcac cggggaccag catgtggaac tccaggaacc gccgatagcc     180
ggcctcccgg gtgcggatgg cgtggaaggc aacccgctcg ctgctgtgct ggtccaggaa     240
ctcccggatg gcggcgttgt cggccttcgg cagggagacg tccatcagcc ctgcgcccga     300
ctggccgatg agtcgggccc cggtgacgag gatattcagg cccaccgcga aggccacgat     360
cgggtccagt cgctgccagc cggtgagcca caccaggccg actcccacga ccacgccgat     420
cgaggtgacg acgtcggtcc acaggtgccg accgtcggcc agcagggtca tcgagcgacg     480
acgccggccg ttgcgcatga ggaccgcggc caccgagccg ttgatgaccg aggcgaccgc     540
cgagaccacc aggcccagtc ccagattctc caggccctgg gggtgcagga agcggtcgac     600
ggccgagacc aggatgacgg ccgccgcgac gaagatcatg atgccctcga ccgccgcgga     660
gaagtactcg gccttcgagt gcccgaactg gtggttcttg tccggcggct tgatggacac     720
cttgagggcc accagggcga cgatcgcggc caccaggttc accaccgact cggcggcgtc     780
cgagagcagg cccaccgatc cggtgagaag ccacgctccg gtcttgagga ggatggtggc     840
gatcgccgcc gcgatcgaca gccaggcgaa acggctcagg cctccggag gttcgtggcg     900
cggggccgag ttggctgtcg gggggatccg ggggctgctc accgcgccaa ttatgccagc     960
gtccgggcga tcggccac                                                  978
```

<210> SEQ ID NO 14
<211> LENGTH: 326
<212> TYPE: PRT
<213> ORGANISM: Propionibacterium acidi-propionici

<400> SEQUENCE: 14

```
Ser Asp Val Gln Ile Leu Ile Gly Pro Gly Val Leu Asp Arg Phe Gln
  1               5                  10                  15

Val Ala His His Pro Gln Ile Gly Pro Leu Val Glu Glu Phe Val Asp
                 20                  25                  30

Glu Val Leu His Asp Val Val Ala Val Leu Asn Gly Pro Leu Thr Gly
             35                  40                  45

Asp Gln His Val Glu Leu Gln Glu Pro Pro Ile Ala Gly Leu Pro Gly
         50                  55                  60

Ala Asp Gly Val Glu Gly Asn Pro Leu Ala Ala Val Leu Val Gln Glu
 65                  70                  75                  80

Leu Pro Asp Gly Gly Val Val Gly Leu Arg Gln Gly Asp Val His Gln
                 85                  90                  95

Pro Cys Ala Arg Leu Ala Asp Glu Ser Gly Pro Gly Asp Glu Asp Ile
                100                 105                 110

Gln Ala His Arg Glu Gly His Asp Arg Val Gln Ser Leu Pro Ala Gly
            115                 120                 125

Glu Pro His Gln Ala Asp Ser His Asp His Ala Asp Arg Gly Asp Asp
        130                 135                 140

Val Gly Pro Gln Val Pro Thr Val Gly Gln Gln Gly His Arg Ala Thr
145                 150                 155                 160

Thr Pro Ala Val Ala His Glu Asp Arg Gly His Arg Ala Val Asp Asp
                165                 170                 175

Arg Gly Asp Arg Arg Asp His Gln Ala Gln Ser Gln Ile Leu Gln Ala
            180                 185                 190

Leu Gly Val Gln Glu Ala Val Asp Gly Arg Asp Gln Asp Asp Gly Arg
```

```
              195                 200                 205
Arg Asp Glu Asp His Asp Ala Leu Asp Arg Arg Gly Glu Val Leu Gly
        210                 215                 220
Leu Arg Val Pro Glu Leu Val Leu Val Arg Leu Asp Gly His
225                 230                 235                 240
Leu Glu Gly His Gln Gly Asp Asp Arg Gly His Gln Val His His Arg
                245                 250                 255
Leu Gly Gly Val Arg Glu Gln Ala His Arg Ser Gly Glu Lys Pro Arg
            260                 265                 270
Ser Gly Leu Glu Glu Asp Gly Gly Asp Arg Arg Arg Asp Arg Gln Pro
        275                 280                 285
Gly Glu Thr Ala Gln Val Leu Arg Arg Phe Val Ala Arg Gly Arg Val
        290                 295                 300
Gly Cys Arg Gly Asp Pro Gly Ala Ala His Arg Ala Asn Tyr Ala Ser
305                 310                 315                 320
Val Arg Ala Ile Gly His
                325

<210> SEQ ID NO 15
<211> LENGTH: 3103
<212> TYPE: DNA
<213> ORGANISM: Propionibacterium acidi-propionici

<400> SEQUENCE: 15
gttgcaagct actaagtgcg gtcggtggat gccttggcac caagagccga tgaaggacgt    60
tgtaacctgc gataagcccc ggggagttgg ttcacgagct gtgatccggg ggtgtccgaa   120
tggggaaacc ttgaattgcc ggagtcatgt ccggtgaccc tgccctgaat gtatagggt    180
gtgggaggga acgtggggaa gtgaaacatc tcagtacccg caggaagaga aacaatatg    240
tgattccgtg agtagtggcg agcgaaagcg gatgaggcca aaccgtgtgt gtgttcaaac   300
cggcaggtgt tgcacgtgcg gggttgtggg gtcttctggg atcgactgcc gtcggtccgt   360
ccagtgataa atggtgtgtt gaagtcgaag cgtctgggaa ggcgtaccgg agtgggtgag   420
agtcccgtag acgtggatgc accactggtg gaggataccc aagtagcgc gggactcgtg    480
gaatttcgcg tgaatctggc gggaccaccc gtcaagcctg aatactcctt ggtgaccgat   540
agtggatagt accgtgaggg aatggtgaaa agtaccccgg gaggggagtg aaagagtacc   600
tgaaaccggc cgcatacaat ccgtcggagc ctgcctgtac gggtgggtga cggcgtgcct   660
attgaagaat gagcctgcga gttagtggca tgtggcgagg ttaacccgtg tggggtagtc   720
gtagcgaaag cgagtccgat aagggcgcca gtcgcgtgtt ctagacccga gcggtgtga    780
tctatccatg gccaggatga agcgacggta agacgtcgtg gaggtccgca cccacttcag   840
ttgaaaatgg agggggatgag ctgtggatag gggtgaaagg ccaatcaaac actgtgatag   900
ctggttctcc ccgaaatgca tttaggtgca gcgtcgcgtg gttcttgctg gaggtagagc   960
actgatgat ctaggggggcc tatcagctta ccgaaatcag ccaaactccg aatgccggca  1020
agtggagcgt ggcagtgaga cggcggggga taagcttcgt cgtcgagagg gaaacagccc  1080
agatcatcag ctaaggcccc taagcggtgg ctaagtggaa aaggatgtgg agttgcggtg  1140
acaaccagga ggttggcttg gaagcagcca tccttgaaag agtgcgtaat agctcactgg  1200
tcaagtgatt ccgcgccgac aatgtagcgg ggctcaagcc atccgccgaa gctgtggcaa  1260
tcaggattta ctcctggttg ggtaggggag cgtcgtgttc tcggtgaagc ggtccggtga  1320
cgggtcgtgg aggggatgcg agtgagaatg caggcatgag tagcgaatga cggggtgagaa  1380
```

```
acccgtccgc cgaatatcca agggttccag ggtcaagtta atcttccctg ggtgagtcgg    1440
gacctaaggc gaggccgaca ggcgtagtcg atggacgacc agttgatatt ctggtaccgg    1500
tgtagcaccg tccgtgtcga ggtgtgtgat gctaagcatg cgagtccctg ttccgcgggc    1560
ctttggtctg tggggtgggt ggtgagtgtg tgaaccgatc atgtagtagg caagctgcgg    1620
agggacgcag ggaggtagct caaccccagc gatggttgtc tggggctaaa cgtgtggacc    1680
gtccggtagg taaatccgcc gggcatgatg gttgaggcgt gatggcgagc ccactgtgtg    1740
ggtgagtgag tgatcctgta ctgccgagaa aagcttcgtg agcgaggtgt gagccgcccg    1800
taccctaaac cgacactggt ggattggtag agtataccga ggcgatcgag agaatcatgg    1860
tgaaggaact cggcaaaatg accccgtaac ttcgggataa ggggtgcccg aaccgtccgg    1920
ctgtttactg gctgggggcg gtgagggtcg cagagtccag ggggaaacga ctgtttacta    1980
aaaacacagg tccgtgcgaa gttgtaagac gatgtatacg gactgactcc tgcccggtgc    2040
tggaaggtta aggggaactg tcagggcctt cgggttcgaa gcggtgaact taagccccag    2100
taaacggcgg tggtaactat aaccatccta aggtagcgaa attccttgtc gggtaagttc    2160
cgacctgcac gaatggagta acgatttccc tactgtctcc accatgaact cggtgaaatt    2220
gcattacgag taaagatgct cgttacgcgc agcaggacgg aaagaccccg ggacctttac    2280
tatagtttgg tattggtgat cggtgcgact tgtgtaggat aggtgggaga cggtgaagcg    2340
gccacgccag tggttgtgga gtcattgttg aaataccact ctggtcgttc tggttacctc    2400
acctcggacc gtgatccggt tcagggacag tgcctgatgg gtagtttgac tggggcggtc    2460
gcctcctaaa aggtaacgga ggcgcccaaa ggttccctca gcctggttgg taatcaggtg    2520
tcgagtgtaa gtgcacaagg gagcttgact gtgagacagg catgtcgagc agggacgaga    2580
gtcgggacta gtgatctgac ggtggcttgt ggaagtgccg tcactcaacg gataaaaggt    2640
accccgggga taacaggctg atcttgcccg agcgctcaca gcgacggcat ggtttggcac    2700
ctcgatgtcg gctcgtcgca tcctgggggct ggagtcggtc ccaagggttg ggctgttcgc    2760
ccattaaagc ggcacgcgag ctgggtttag aacgtcgtga gacagttcgg tccctatccg    2820
ctgcgcgcac aggaatcttg agaagagctg tctctagtac gagaggaccg agacggactg    2880
acctctggtg tgccagttgt tccgccagga gcatggctgg ttggctacgt cgggtcgtga    2940
taaccgctga aagcatctaa gcgggaagca cgcttcaaga tgagggttcc cacagatgaa    3000
tctggtaagg cccccgagag atgatcgggt tgataggccg gacgtggacg cactgcaagg    3060
tgcggagctg accggtacta ataggccgag ggcttgcccc aca                       3103
```

<210> SEQ ID NO 16
<211> LENGTH: 2335
<212> TYPE: DNA
<213> ORGANISM: Propionibacterium acidi-propionici
<220> FEATURE:
<221> NAME/KEY: CDS
<222> LOCATION: (1)..(1500)

<400> SEQUENCE: 16

```
atg aac acg gcc gag tat ctg gtc ggc gac ggc gag tcg gga tcg gtg         48
Met Asn Thr Ala Glu Tyr Leu Val Gly Asp Gly Glu Ser Gly Ser Val
1               5                   10                  15 gcg gtg gtg gac tcc gac ggg gtg cac agc tat gcc gac ctc cgc gcg         96
Ala Val Val Asp Ser Asp Gly Val His Ser Tyr Ala Asp Leu Arg Ala
            20                  25                  30 cag gcg tcg agg tgc cgt gcc gcc ctc gag gaa ctc ggg ttg cgc gcc        144
```

```
            Gln Ala Ser Arg Cys Arg Ala Ala Leu Glu Glu Leu Gly Leu Arg Ala
                     35                  40                  45 ggc gac cgc gtc ggg ctg atc ggc gcg aac tgc ttc ggc tgg gtg gcc        192
Gly Asp Arg Val Gly Leu Ile Gly Ala Asn Cys Phe Gly Trp Val Ala
 50                  55                  60 gcc tac ctg ggg gtg ctg gcc gcc ggc atg gtc gcc gtg ccg atc gcc        240
Ala Tyr Leu Gly Val Leu Ala Ala Gly Met Val Ala Val Pro Ile Ala
 65                  70                  75                  80 cat acc ctg cgc ccc gac gag atc gtc tcc aga atc cgg tgg ctc ggc        288
His Thr Leu Arg Pro Asp Glu Ile Val Ser Arg Ile Arg Trp Leu Gly
                     85                  90                  95 gtc cag gcc gcc ttc ctg ggc ccg atg gag tcg cgc cga ctc gcc gga        336
Val Gln Ala Ala Phe Leu Gly Pro Met Glu Ser Arg Arg Leu Ala Gly
                100                 105                 110 cag gtc ccg ggg ggt ctt cct atg gcc gcc gag ggt ccg tcg ccg gcg        384
Gln Val Pro Gly Gly Leu Pro Met Ala Ala Glu Gly Pro Ser Pro Ala
            115                 120                 125 ggc ccc ccg ctg cga ttc gtc gat cgg ccc gcc gat ctg gac gcc gcc        432
Gly Pro Pro Leu Arg Phe Val Asp Arg Pro Ala Asp Leu Asp Ala Ala
130                 135                 140 ctg gtg ttc acc tcg ggc acc acc ggc cgg ccg cac gtc gtg cgg ctc        480
Leu Val Phe Thr Ser Gly Thr Thr Gly Arg Pro His Val Val Arg Leu
145                 150                 155                 160 acc cac gcc aac ctg cag gcc aac acc ggc tcc atc ctg agc tat ctg        528
Thr His Ala Asn Leu Gln Ala Asn Thr Gly Ser Ile Leu Ser Tyr Leu
                165                 170                 175 ccg ctg gca gat tcg gat cga gtc ctt gtc gtg ctg ccc ttc agc tac        576
Pro Leu Ala Asp Ser Asp Arg Val Leu Val Val Leu Pro Phe Ser Tyr
            180                 185                 190 gtc ttc ggg gcc tcc ctg ctg cac acc cac ctg agg gtg gga gcg gcc        624
Val Phe Gly Ala Ser Leu Leu His Thr His Leu Arg Val Gly Ala Ala
        195                 200                 205 ctg gtg gtg cag ccg aac gcc gcc ttc ccc cag cag atg gtc gag cgg        672
Leu Val Val Gln Pro Asn Ala Ala Phe Pro Gln Gln Met Val Glu Arg
210                 215                 220 atg gcc gcc gag cga tgc acc ggc ctc gcg ggg gtg ccc tcc acc ttc        720
Met Ala Ala Glu Arg Cys Thr Gly Leu Ala Gly Val Pro Ser Thr Phe
225                 230                 235                 240 tcg gtg ctg ctg cgc aac agc acc ttc ggc tcc cgt cgg ctg ccc gac        768
Ser Val Leu Leu Arg Asn Ser Thr Phe Gly Ser Arg Arg Leu Pro Asp
                245                 250                 255 ctg cgc atc atc cag cag gcc ggc ggc agg ctc gcg ccg acg atg gtc        816
Leu Arg Ile Ile Gln Gln Ala Gly Gly Arg Leu Ala Pro Thr Met Val
            260                 265                 270 gag gag ttg cgc ggg gcc cag ccc cag gcg cag gtg ttc gtg atg tac        864
Glu Glu Leu Arg Gly Ala Gln Pro Gln Ala Gln Val Phe Val Met Tyr
        275                 280                 285 ggg cag acc gag gcc acc gcg cgg ctg tcc tac ctg ccg ccc cag gag        912
Gly Gln Thr Glu Ala Thr Ala Arg Leu Ser Tyr Leu Pro Pro Gln Glu
290                 295                 300 ctg gat cgc cgt ccg ggg tcg atc ggc cgg gga ata ccg gga gtg gac        960
Leu Asp Arg Arg Pro Gly Ser Ile Gly Arg Gly Ile Pro Gly Val Asp
305                 310                 315                 320 ctg cgc gtg gtc ggc gag gac ggc tcg cag gtc gcc gcc gga cag atc       1008
Leu Arg Val Val Gly Glu Asp Gly Ser Gln Val Ala Ala Gly Gln Ile
                325                 330                 335 ggc gag atc gtg gcc ggc ggg gac aat atc tcg ccc ggc tac ctc gac       1056
Gly Glu Ile Val Ala Gly Gly Asp Asn Ile Ser Pro Gly Tyr Leu Asp
            340                 345                 350
```

```
gac ccc gag gag acc gcc cgg cgg atg ccc gga ggg gta ctg cgg acc      1104
Asp Pro Glu Glu Thr Ala Arg Arg Met Pro Gly Gly Val Leu Arg Thr
        355                 360                 365 ggc gat ctg gcg acg gtc gac gag gac ggt tac atc tac gtc gtc gat      1152
Gly Asp Leu Ala Thr Val Asp Glu Asp Gly Tyr Ile Tyr Val Val Asp
370                 375                 380 cgc agg gag gac ttc atc aag tcg tgg ggg gtg agg atc tcg agt cag      1200
Arg Arg Glu Asp Phe Ile Lys Ser Trp Gly Val Arg Ile Ser Ser Gln
385                 390                 395                 400 gac atc gag gcg gtg gcg ctg cag ctc acc gat ctc gtg tcg gtg gct      1248
Asp Ile Glu Ala Val Ala Leu Gln Leu Thr Asp Leu Val Ser Val Ala
                405                 410                 415 gcg gtg gga gtg ccc gac gag gcc gcc ggg gag cgg gtc gag ttg gtg      1296
Ala Val Gly Val Pro Asp Glu Ala Ala Gly Glu Arg Val Glu Leu Val
            420                 425                 430 gcc gtg ccc cgg gag ggg tcg cgg ctc acc gag ggc cag atc atc gac      1344
Ala Val Pro Arg Glu Gly Ser Arg Leu Thr Glu Gly Gln Ile Ile Asp
        435                 440                 445 cac tgc cgg gcc cgg ctg gct agg acc atg gtg ccg cag gcc gtg cat      1392
His Cys Arg Ala Arg Leu Ala Arg Thr Met Val Pro Gln Ala Val His
    450                 455                 460 ctt gtc ccg ttg atg ccc ctc aac ggc aac ggt aaa atc tcc aag aca      1440
Leu Val Pro Leu Met Pro Leu Asn Gly Asn Gly Lys Ile Ser Lys Thr
465                 470                 475                 480 gcg gtc cgc gaa ctc tgc gtg gat ctg gcc aga gcc gac cag tcc cca      1488
Ala Val Arg Glu Leu Cys Val Asp Leu Ala Arg Ala Asp Gln Ser Pro
                485                 490                 495 gga gga tca tca tgaggcggaa accagtcgtc gtcctgatcg caggcgtcct          1540
Gly Gly Ser Ser
            500 cgcggtggtg gtcgccagcg gcgcatgggt gctgcagggc aggcccgacc cgctgccctc    1600 ctcggtggtg aacacggccg ccggcgacga cgagctcgcc gatttcagcg gcggaggat     1660 cttcttcggt caccagtccg tcgggcgaa catcatcgat ggtctgaaag ccgcctattc     1720 gggccgggag ggctccggcc tcgacgttgt cgagacgcgc accgatccag caggagcgg     1780 cggatacctg gccatgccg cgatgggggt caacggcgac ccgctcggca aactcgccga     1840 tttcgagaag gtgctggccg gctcgatggg cggcgcggtc gacctcgccg tgctcaagct    1900 gtgctacatc gacgtcacgg ccgacaccga cgtcgacgcg ctgttcacgg cgtactcgca    1960 gaccatgacc aggctcgagg ccgcccatcc gggggtcacc ttcatctaca cgacagtccc    2020 gctgaccacc gaccggacct ggaagcagac cgtcaagtcg tggatcgggc gcgacgagca    2080 gacggggccg gacgacaacg ccgcccgcca gcgttacaac cggctcgtgc gcgagcggta    2140 cggcgattcc gacaggctct tcgacatcgc cgcggtccag gccacgatgg acagctcccc    2200 gacctcgcgg acccgtgacg gatccaccta ctacgtcctt cacgaccggc tggcggccga    2260 ccccgggccc tcaacgcgct ggggtcacgg gtgaccgccg cccgcctcgt gcacctggtg    2320 gccgcacagc actag                                                    2335

<210> SEQ ID NO 17
<211> LENGTH: 500
<212> TYPE: PRT
<213> ORGANISM: Propionibacterium acidi-propionici

<400> SEQUENCE: 17

Met Asn Thr Ala Glu Tyr Leu Val Gly Asp Gly Glu Ser Gly Ser Val
1               5                   10                  15
```

-continued

```
Ala Val Val Asp Ser Asp Gly Val His Ser Tyr Ala Asp Leu Arg Ala
             20                  25                  30
Gln Ala Ser Arg Cys Arg Ala Ala Leu Glu Glu Leu Gly Leu Arg Ala
         35                  40                  45
Gly Asp Arg Val Gly Leu Ile Gly Ala Asn Cys Phe Gly Trp Val Ala
     50                  55                  60
Ala Tyr Leu Gly Val Leu Ala Ala Gly Met Val Ala Val Pro Ile Ala
 65                  70                  75                  80
His Thr Leu Arg Pro Asp Glu Ile Val Ser Arg Ile Arg Trp Leu Gly
                 85                  90                  95
Val Gln Ala Ala Phe Leu Gly Pro Met Glu Ser Arg Arg Leu Ala Gly
            100                 105                 110
Gln Val Pro Gly Gly Leu Pro Met Ala Ala Glu Gly Pro Ser Pro Ala
        115                 120                 125
Gly Pro Pro Leu Arg Phe Val Asp Arg Pro Ala Asp Leu Asp Ala Ala
    130                 135                 140
Leu Val Phe Thr Ser Gly Thr Thr Gly Arg Pro His Val Val Arg Leu
145                 150                 155                 160
Thr His Ala Asn Leu Gln Ala Asn Thr Gly Ser Ile Leu Ser Tyr Leu
                165                 170                 175
Pro Leu Ala Asp Ser Asp Arg Val Leu Val Val Leu Pro Phe Ser Tyr
            180                 185                 190
Val Phe Gly Ala Ser Leu Leu His Thr His Leu Arg Val Gly Ala Ala
        195                 200                 205
Leu Val Val Gln Pro Asn Ala Ala Phe Pro Gln Gln Met Val Glu Arg
    210                 215                 220
Met Ala Ala Glu Arg Cys Thr Gly Leu Ala Gly Val Pro Ser Thr Phe
225                 230                 235                 240
Ser Val Leu Leu Arg Asn Ser Thr Phe Gly Ser Arg Arg Leu Pro Asp
                245                 250                 255
Leu Arg Ile Ile Gln Gln Ala Gly Gly Arg Leu Ala Pro Thr Met Val
            260                 265                 270
Glu Glu Leu Arg Gly Ala Gln Pro Gln Ala Gln Val Phe Val Met Tyr
        275                 280                 285
Gly Gln Thr Glu Ala Thr Ala Arg Leu Ser Tyr Leu Pro Pro Gln Glu
    290                 295                 300
Leu Asp Arg Arg Pro Gly Ser Ile Gly Arg Gly Ile Pro Gly Val Asp
305                 310                 315                 320
Leu Arg Val Val Gly Glu Asp Gly Ser Gln Val Ala Ala Gly Gln Ile
                325                 330                 335
Gly Glu Ile Val Ala Gly Gly Asp Asn Ile Ser Pro Gly Tyr Leu Asp
            340                 345                 350
Asp Pro Glu Glu Thr Ala Arg Arg Met Pro Gly Val Leu Arg Thr
        355                 360                 365
Gly Asp Leu Ala Thr Val Asp Glu Asp Gly Tyr Ile Tyr Val Val Asp
    370                 375                 380
Arg Arg Glu Asp Phe Ile Lys Ser Trp Gly Val Arg Ile Ser Ser Gln
385                 390                 395                 400
Asp Ile Glu Ala Val Ala Leu Gln Leu Thr Asp Leu Val Ser Val Ala
                405                 410                 415
Ala Val Gly Val Pro Asp Glu Ala Ala Gly Glu Arg Val Glu Leu Val
            420                 425                 430
Ala Val Pro Arg Glu Gly Ser Arg Leu Thr Glu Gly Gln Ile Ile Asp
```

```
        435                 440                 445
His Cys Arg Ala Arg Leu Ala Arg Thr Met Val Pro Gln Ala Val His
    450                 455                 460

Leu Val Pro Leu Met Pro Leu Asn Gly Asn Gly Lys Ile Ser Lys Thr
465                 470                 475                 480

Ala Val Arg Glu Leu Cys Val Asp Leu Ala Arg Ala Asp Gln Ser Pro
                485                 490                 495

Gly Gly Ser Ser
            500

<210> SEQ ID NO 18
<211> LENGTH: 5205
<212> TYPE: DNA
<213> ORGANISM: Propionibacterium acidi-propionici

<400> SEQUENCE: 18
ttttcattgg agagtttgat cctggctcag gacgaacgct ggcggcgtgc ttaacacatg      60
caagtcgaac ggtaaggccc tttcgggggt acacgagtgg cgaacgggtg agtaacacgt     120
gagtaacctg cccacttctt cgggataacg ctaggaaact ggtgctaata ccggatatga     180
gctcctgccg catggtgggg gttggaaagt gtttgtggtg gtggatggac tcgcggccta     240
tcagcttgtt ggtgaggtag tggctcacca aggcggtgac gggtagccgg cctgagaggg     300
tgaccggcca cattgggact gagatacggc ccagactcct acgggaggca gcagtgggga     360
atattgcaca atgggcggaa gcctgatgca gcaacgccgc gtgcgggatg acggccttcg     420
ggttgtaaac cgctttcacc aggggcgaag gcatcctttt ggggtgttga cggtacctgg     480
agaagaagca ccggctaact acgtgccagc agccgcggtg atacgtaggg tgcgagcgtt     540
gtccggattt attgggcgta aagggctcgt aggcggttga tcgcgtcgga agtgaaaact     600
tggggcttaa ccctgagcgt gctttcgata cgggttgact tgaggaaggt aggggagaat     660
ggaattcctg gtgagcggt ggaatgcgca gatatcagga ggaacaccag tggcgaaggc     720
ggttctctgg acctttcctg acgctgagga gcgaaagcgt ggggagcaaa caggcttaga     780
taccctggta gtccacgctg taaacggtgg gtactaggtg tggggtccat tccacggatt     840
ccgtgccgta gctaacgcat taagtacccc gcctggggag tacggccgca aggctaaaac     900
tcaaaggaat tgacggggcc ccgcacaagc ggcggagcat gcggattaat tcgatgcaac     960
gcgaagaacc ttacctgggt ttgacatgga ttggtaacgg tcagagatgg ccgccccct    1020 tgtgggccgg ttcacaggtg gtgcatggct gtcgtcagct cgtgtcgtga tgttgggt     1080 taagtcccgc aacgagcgca accctcgtcc actgttgcca gcatttggtt ggggactcag    1140
tggagaccgc cggggtcaac tcggaggaag gtggggatga cgtcaagtca tcatgcccct    1200
tatgtccagg gcttcacgca tgctacaatg gccggtacaa agagtggcga catcgtgagg    1260
tggagcgaat ctcagaaagc cggtctcagt tcggattggg gtctgcaact cgacccatg    1320 aagtcggagt cgctagtaat cgcagatcag caacgctgcg gtgaatacgt tcccggggct    1380
tgtacacacc gcccgtcaag tcatgaaagt cggtaacacc gaagccggt ggcccaacac    1440 gttctgcgtg gggagtcgt cgaaggtggg actggtaatt aggactaagt cgtaacaagg    1500
tagccgtacc ggaaggtgcg gctggatcac ctcctttcta aggagctttc tggaagccgg    1560
tcgtcgcccg agtgtggtga tggttcggtt caggctgtcg ggtccttgcg ggtccggtgg    1620
tgcttctgag tggaatgttg gctatggacg cttctggtct tcgggtcggg ggtgggatgc    1680
actgttgggg ttctggggta tcacctgcac aggtggtggc ctggtgtggc ggacatcgct    1740
```

```
gccggctggc ctggttgtcg ggttggtgtg gtgggtgtct cgtgtggtgg ttgagaactg    1800
tacagtggat atgagcatct ttgtagattt tttgtaatgt gttgtgttgc aagctactaa    1860
gtgcggtcgg tggatgcctt ggcaccaaga gccgatgaag gacgttgtaa cctgcgataa    1920
gccccgggga gttggttcac gagctgtgat ccggggtgt ccgaatgggg aaaccttgaa    1980
ttgccggagt catgtccggt gaccctgccc tgaatgtata ggggtgtggg agggaacgtg    2040
gggaagtgaa acatctcagt acccgcagga agagaaaaca atatgtgatt ccgtgagtag    2100
tggcgagcga aagcggatga ggccaaaccg tgtgtgtgtt caaaccggca ggtgttgcac    2160
gtgcggggtt gtgggtgtctt ctgggatcga ctgccgtcgg tccgtccagt gataaatggt    2220
gtgttgaagt cgaagcgtct gggaaggcgt accggagtgg gtgagagtcc cgtagacgtg    2280
gatgcaccac tggtggagga tacccccaagt agcgcgggac tcgtggaatt cgcgtgaat    2340 ctggcgggac cacccgtcaa gcctgaatac tccttggtga ccgatagtgg atagtaccgt    2400
gagggaatgg tgaaaagtac cccgggaggg gagtgaaaga gtacctgaaa ccggccgcat    2460
acaatccgtc ggagcctgcc tgtacgggtg ggtgacggcg tgcctattga agaatgagcc    2520
tgcgagttag tggcatgtgg cgaggttaac ccgtgtgggg tagtcgtagc gaaagcgagt    2580
ccgataaggg cgccagtcgc gtgttctaga cccgaagcgg tgtgatctat ccatggccag    2640
gatgaagcga cggtaagacg tcgtggaggt ccgcacccac ttcagttgaa aatggagggg    2700
atgagctgtg gataggggtg aaaggccaat caaacactgt gatagctggt tctccccgaa    2760
atgcatttag gtgcagcgtc gcgtggttct tgctggaggt agagcactgg atgatctagg    2820
gggcctatca gcttaccgaa atcagccaaa ctccgaatgc cggcaagtgg agcgtggcag    2880
tgagacggcg ggggataagc ttcgtcgtcg agagggaaac agcccagatc atcagctaag    2940 gccccctaagc ggtggctaag tggaaaagga tgtggagttg cggtgacaac caggaggttg    3000
gcttggaagc agccatcctt gaaagagtgc gtaatagctc actggtcaag tgattccgcg    3060
ccgacaatgt agcggggctc aagccatccg ccgaagctgt ggcaatcagg atttactcct    3120
ggttgggtag gggagcgtcg tgttctcggt gaagcggtcc ggtgacgggt cgtggagggg    3180
atgcgagtga gaatgcaggc atgagtagcg aatgacgggg gagaaacccg tccgccgaat    3240
atccaagggt tccagggtca agttaatctt ccctggtga gtcgggacct aaggcgaggc    3300
cgacaggcgt agtcgatgga cgaccagttg atattctggt accggtgtag caccgtccgt    3360
gtcgaggtgt gtgatgctaa gcatgcgagt ccctgttccg cgggccttg gtctgtgggg    3420 tgggtggtga gtgtgtgaac cgatcatgta gtaggcaagc tgcggaggga cgcagggagg    3480
tagctcaacc ccagcgatgg ttgtctgggg ctaaacgtgt ggaccgtccg gtaggtaaat    3540
ccgccgggca tgatggttga ggcgtgatgg cgagcccact gtgtgggtga gtgagtgatc    3600
ctgtactgcc gagaaaagct tcgtgagcga ggtgtgagcc gcccgtaccc taaaccgaca    3660
ctggtggatt ggtagagtat accgaggcga tcgagagaat catggtgaag gaactcggca    3720
aaatgacccc gtaacttcgg gataagggt gcccgaaccg tccggctgtt tactggctgg    3780
gggcggtgag ggtcgcagag tccagggga aacgactgtt tactaaaaac acaggtccgt    3840
gcgaagttgt aagacgatgt atacggactg actcctgccc ggtgctggaa ggttaagggg    3900
aactgtcagg gccttcgggt tcgaagcggt gaacttaagc cccagtaaac ggcggtggta    3960
actataacca tcctaaggta gcgaaattcc ttgtcgggta agttccgacc tgcacgaatg    4020
gagtaacgat ttccctactg tctccaccat gaactcggtg aaattgcatt acgagtaaag    4080
```

-continued

```
atgctcgtta cgcgcagcag gacggaaaga ccccgggacc tttactatag tttggtattg    4140
gtgatcggtg cgacttgtgt aggataggtg ggagacggtg aagcggccac gccagtggtt    4200
gtggagtcat tgttgaaata ccactctggt cgttctggtt acctcacctc ggaccgtgat    4260
ccggttcagg gacagtgcct gatgggtagt ttgactgggg cggtcgcctc ctaaaaggta    4320
acggaggcgc ccaaaggttc cctcagcctg gttggtaatc aggtgtcgag tgtaagtgca    4380
caagggagct tgactgtgag acaggcatgt cgagcaggga cgagagtcgg gactagtgat    4440
ctgacggtgg cttgtggaag tgccgtcact caacggataa aaggtacccc ggggataaca    4500
ggctgatctt gcccgagcgc tcacagcgac ggcatggttt ggcacctcga tgtcggctcg    4560
tcgcatcctg gggctggagt cggtcccaag ggttgggctg ttcgcccatt aaagcggcac    4620
gcgagctggg tttagaacgt cgtgagacag ttcggtccct atccgctgcg cgcacaggaa    4680
tcttgagaag agctgtctct agtacgagag gaccgagacg gactgacctc tggtgtgcca    4740
gttgttccgc caggagcatg gctggttggc tacgtcgggt cgtgataacc gctgaaagca    4800
tctaagcggg aagcacgctt caagatgagg gttcccacag atgaatctgg taaggccccc    4860
gagagatgat cgggttgata ggccggacgt ggacgcactg caaggtgcgg agctgaccgg    4920
tactaatagg ccgagggctt gccccacaca ccatcatcga caattacgcg catatccact    4980
gtacggctcc cggccaccac accccccac acggggctg gtgcgccaca catgtgagtc    5040
acaacacaat acgagttccg tctggaacac cccaagattc tggtgttccg gtggccatgg    5100
ctggagggaa acaccggtc ccattccgaa cccggaagtt aagcctccac acgctgatgg    5160
tactgcccac gccagtgggt gggagagtaa gacgccgccg gaaca                   5205
```

<210> SEQ ID NO 19
<211> LENGTH: 471
<212> TYPE: DNA
<213> ORGANISM: Propionibacterium acidi-propionici
<220> FEATURE:
<221> NAME/KEY: CDS
<222> LOCATION: (1)..(471)

<400> SEQUENCE: 19

```
gtg tcc tcg ggc cac gtc tcc tcc cag tcg gag ctc ggc gcc tcc ctg    48
Val Ser Ser Gly His Val Ser Ser Gln Ser Glu Leu Gly Ala Ser Leu
1               5                   10                  15 gcg gcc gaa gga atg gcg gtg tcc cag ggg acc ctg tca cgg gac ctg    96
Ala Ala Glu Gly Met Ala Val Ser Gln Gly Thr Leu Ser Arg Asp Leu
            20                  25                  30 gtg gag atc ggc gcg gtg cgc gga cgg gac aag aac ggg aac ccc tgc   144
Val Glu Ile Gly Ala Val Arg Gly Arg Asp Lys Asn Gly Asn Pro Cys
        35                  40                  45 tac acc atc cct gag ggg gag cat ccg tcc gac gtg acg acc gga tca   192
Tyr Thr Ile Pro Glu Gly Glu His Pro Ser Asp Val Thr Thr Gly Ser
    50                  55                  60 ccg gca tgg agc aga ctg gcc cgc ctc acc cgc gaa ctg tgc acc ggc   240
Pro Ala Trp Ser Arg Leu Ala Arg Leu Thr Arg Glu Leu Cys Thr Gly
65                  70                  75                  80 gtc cag cac aat gac acc ctc gtc gtc ctg aag acc ccg ccg ggg gcc   288
Val Gln His Asn Asp Thr Leu Val Val Leu Lys Thr Pro Pro Gly Ala
                85                  90                  95 gcg cag tac ttc ggt tcg gcg atc gac cgt tcc gga tcg agg gcg atc   336
Ala Gln Tyr Phe Gly Ser Ala Ile Asp Arg Ser Gly Ser Arg Ala Ile
            100                 105                 110 ctg gga acg ata gcc ggg gac gac acg atc gcc ctc atc tgc gcc gcg   384
Leu Gly Thr Ile Ala Gly Asp Asp Thr Ile Ala Leu Ile Cys Ala Ala
```

```
                    115                 120                 125
gag gtg agc gcg gac gcg ctg gcc gac gcg ttc agg cag atg gcc gag      432
Glu Val Ser Ala Asp Ala Leu Ala Asp Ala Phe Arg Gln Met Ala Glu
        130                 135                 140 acc ggc ttc ccg gcg cca ctg ctg tcc gag ggg agc tga                  471
Thr Gly Phe Pro Ala Pro Leu Leu Ser Glu Gly Ser
145                 150                 155

<210> SEQ ID NO 20
<211> LENGTH: 156
<212> TYPE: PRT
<213> ORGANISM: Propionibacterium acidi-propionici

<400> SEQUENCE: 20

Val Ser Ser Gly His Val Ser Ser Gln Ser Glu Leu Gly Ala Ser Leu
1               5                   10                  15

Ala Ala Glu Gly Met Ala Val Ser Gln Gly Thr Leu Ser Arg Asp Leu
                20                  25                  30

Val Glu Ile Gly Ala Val Arg Gly Arg Asp Lys Asn Gly Asn Pro Cys
            35                  40                  45

Tyr Thr Ile Pro Glu Gly Glu His Pro Ser Asp Val Thr Thr Gly Ser
        50                  55                  60

Pro Ala Trp Ser Arg Leu Ala Arg Leu Thr Arg Glu Leu Cys Thr Gly
65                  70                  75                  80

Val Gln His Asn Asp Thr Leu Val Val Leu Lys Thr Pro Pro Gly Ala
                85                  90                  95

Ala Gln Tyr Phe Gly Ser Ala Ile Asp Arg Ser Gly Ser Arg Ala Ile
                100                 105                 110

Leu Gly Thr Ile Ala Gly Asp Asp Thr Ile Ala Leu Ile Cys Ala Ala
            115                 120                 125

Glu Val Ser Ala Asp Ala Leu Ala Asp Ala Phe Arg Gln Met Ala Glu
        130                 135                 140

Thr Gly Phe Pro Ala Pro Leu Leu Ser Glu Gly Ser
145                 150                 155

<210> SEQ ID NO 21
<211> LENGTH: 469
<212> TYPE: DNA
<213> ORGANISM: Propionibacterium acidi-propionici
<220> FEATURE:
<221> NAME/KEY: CDS
<222> LOCATION: (1)..(153)

<400> SEQUENCE: 21 gtg tcc tcg ggc cac gtc tcc tcc cag tcg gag ctc ggc ctc cct ggc      48
Val Ser Ser Gly His Val Ser Ser Gln Ser Glu Leu Gly Leu Pro Gly
1               5                   10                  15 ggc cga agg aat ggc ggt gtc cca ggg gac cct gtc acg gga cct ggt      96
Gly Arg Arg Asn Gly Gly Val Pro Gly Asp Pro Val Thr Gly Pro Gly
                20                  25                  30 gga gat cgg cgc ggt gcg cgg acg gga caa gaa cgg gaa ccc ctg cta     144
Gly Asp Arg Arg Gly Ala Arg Thr Gly Gln Glu Arg Glu Pro Leu Leu
            35                  40                  45 cac cat ccc tgagggggag catccgtccg acgtgacgac cggatcaccg              193
His His Pro
        50 gcatggagca gactggcccg cctcacccgc gaactgtgca ccggcgtcca gcacaatgac    253 accctcgtcg tcctgaagac cccgccgggg gccgcgcagt acttcggttc ggcgatcgac    313
```

```
cgttccggat cgagggcgat cctgggaacg atagccgggg acgacacgat cgccctcatc      373
tgcgccgcgg aggtgagcgc ggacgcgctg gccgacgcgt tcaggcagat ggccgagacc      433
ggcttcccgg cgccactgct gtccgagggg agctga                                469

<210> SEQ ID NO 22
<211> LENGTH: 51
<212> TYPE: PRT
<213> ORGANISM: Propionibacterium acidi-propionici

<400> SEQUENCE: 22

Val Ser Ser Gly His Val Ser Ser Gln Ser Glu Leu Gly Leu Pro Gly
1               5                   10                  15

Gly Arg Arg Asn Gly Gly Val Pro Gly Asp Pro Val Thr Gly Pro Gly
            20                  25                  30

Gly Asp Arg Arg Gly Ala Arg Thr Gly Gln Glu Arg Glu Pro Leu Leu
        35                  40                  45

His His Pro
    50
```